(12) United States Patent
Caruthers et al.

(10) Patent No.: US 11,479,772 B2
(45) Date of Patent: Oct. 25, 2022

(54) THIOMORPHOLINO OLIGONUCLEOTIDES FOR THE TREATMENT OF MUSCULAR DYSTROPHY

(71) Applicants: The Regents of the University of Colorado, Denver, CO (US); Murdoch University, Murdoch (AU)

(72) Inventors: Marvin Caruthers, Boulder, CO (US); Sibasish Paul, Boulder, CO (US); Rakesh N. Veedu, Bull Creek (AU); Katarzyna Jastrzebska, Boulder, CO (US); Heera Krishna, Boulder, CO (US)

(73) Assignee: THE REGENTS OF THE UNIVERSITY OF COLORADO, Denver, CO (US)

( * ) Notice: Subject to any disclaimer, the term of this patent is extended or adjusted under 35 U.S.C. 154(b) by 0 days.

(21) Appl. No.: 16/825,918

(22) Filed: Mar. 20, 2020

(65) Prior Publication Data

US 2020/0308586 A1    Oct. 1, 2020

Related U.S. Application Data

(63) Continuation-in-part of application No. PCT/US2018/051907, filed on Sep. 20, 2018.

(60) Provisional application No. 62/562,162, filed on Sep. 22, 2017.

(51) Int. Cl.
*C12N 15/113* (2010.01)
*A61P 21/00* (2006.01)

(52) U.S. Cl.
CPC ............ *C12N 15/113* (2013.01); *A61P 21/00* (2018.01); *C12N 2310/111* (2013.01); *C12N 2310/314* (2013.01); *C12N 2310/315* (2013.01); *C12N 2310/321* (2013.01); *C12N 2310/3233* (2013.01); *C12N 2310/346* (2013.01); *C12N 2310/3513* (2013.01); *C12N 2310/3517* (2013.01); *C12N 2320/33* (2013.01)

(58) Field of Classification Search
None
See application file for complete search history.

(56) References Cited

U.S. PATENT DOCUMENTS

| 7,468,418 B2 | 12/2008 | Iversen et al. | |
| 2009/0318676 A1* | 12/2009 | Manoharan | C07H 21/02 536/23.1 |
| 2014/0080896 A1 | 3/2014 | Nelson et al. | |
| 2014/0329762 A1* | 11/2014 | Kaye | A61K 31/7125 514/20.9 |
| 2016/0312227 A1* | 10/2016 | Ramiya | C12N 15/1137 |
| 2021/0277047 A1* | 9/2021 | Alawneh | C07H 21/04 |

FOREIGN PATENT DOCUMENTS

| WO | 2012150960 A1 | 11/2012 |
| WO | 2015190922 A1 | 12/2015 |
| WO | 2018057430 A1 | 3/2018 |

OTHER PUBLICATIONS

Paul Sibasish et al: "Thiophosphoramidate morpholino: A new class of antisense oligonucleotides", Abstracts of Papers American Chemical Society, vol. 254, Aug. 20, 2017 (Aug. 20, 2017), p. 33, XP009527415, ISSN: 0065-7727.
Corinne A. Betts et al: "Cell Penetrating Peptide Delivery of Splice Directing Oligonucleotides as a Treatment for Duchenne Muscular Dystrophy", Current Pharmaceutical Design, vol. 19, No. 16, Mar. 1, 2013 (Mar. 1, 2013), pp. 2948-2962, XP055714142, NL ISSN: 1381-6128, DOI: 10.2174/13816128113191600 09.
Langner Heera K. et al: Synthesis and Characterization of Thiophosphoramidate Morpholino Oligonucleotides and Chimeras11, Journal of the American Chemical Society, vol. 142, No. 38, Sep. 23, 2020 (Sep. 23, 2020), pp. 16240-16253, XP055802911, us ISSN: 0002-7863, DOI: 10.1021/jacs.0c04335 Retrieved from the Internet: URL:https://pubs.acs.org/doi/pdf/10.1021/jacs.0c04335>.
European Search Report dated May 11, 2021, 8 pages.
Chen et al., "Synthesis of a Morpholino Nucleic Acid (MNA)-Uridine Phosphoramidte, and Exon Skipping Using MINA/2[-O-Methyl Mixmer Antisense Oligonucleotide", Nov. 22, 2016, vol. 21, No. 11, 9 Pages: E1582 1-9.
International Search Report dated Apr. 12, 2019 in Application No. PCT/US2018/051907, 5 pages.
Written Opinion of the ISA dated Apr. 12, 2019 in Application No. PCT/US2018/051907, 6 pages.

* cited by examiner

*Primary Examiner* — Brian Whiteman
(74) *Attorney, Agent, or Firm* — Berg Hill Greenleaf Ruscitti LLP

(57) ABSTRACT

Improved compositions and methods for treating a disease or disorder through target exon skipping, and preferably muscular dystrophy by administering antisense thiomorpholino molecules capable of binding to a selected target site in the human dystrophin gene to induce exon skipping to produce a functional Dystrophin protein.

16 Claims, 62 Drawing Sheets
Specification includes a Sequence Listing.

Sequence Design of SEQ ID NO. 2
| ODN Number | | |
|---|---|---|
| 1147 | 5'- | G*G*C*C*A*A*a*c*t*c*g*c*T*T*A*C*C*u₂'-OMe |
| 1148 | 5'- | G*G*C*C*A*A*C*C*T*C*G*G*C*T*T*A*C*C*u₂'-OMe |
| 1153 | 5'- | G*g*C*c*A*a*a*C*c*T*c*g*G*c*t*T*a*C*c*u₂'-OMe |
| 1154 | 5'- | g*G*c*C*a*A*c*C*t*C*g*G*c*T*t*A*c*C*t*a*C*c*u₂'-OMe |
| 2'-OMe PS control | 5'- | g*c*c*a*a*c*c*u*c*g*g*c*u*u*a*c*c*u ₂'-OMe |
| PMO control | 5'- | G*G*C*C*A*A*C*C*T*C*G*G*C*T*T*A*C*C*u₂'-OMe |
FIG. 1C
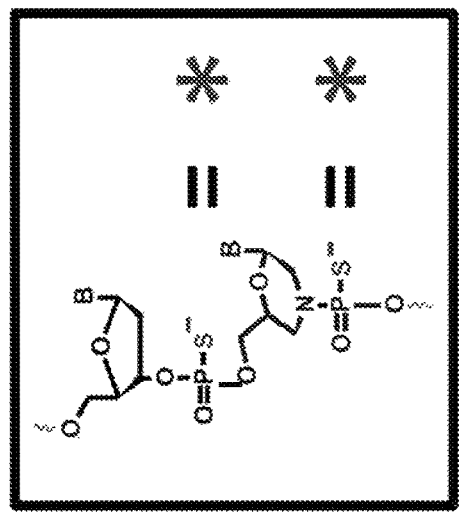
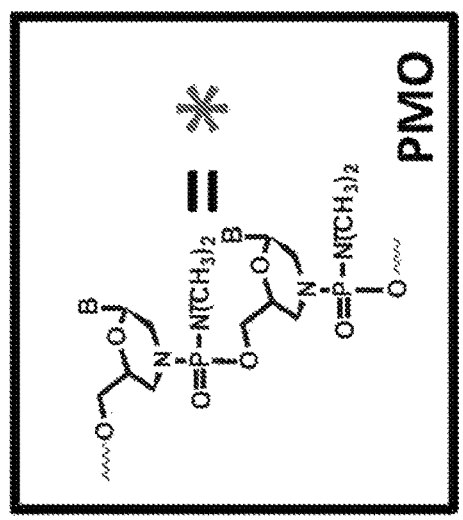
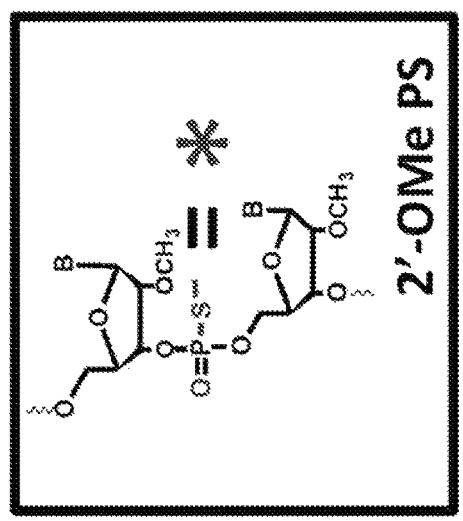
FIG. 1D

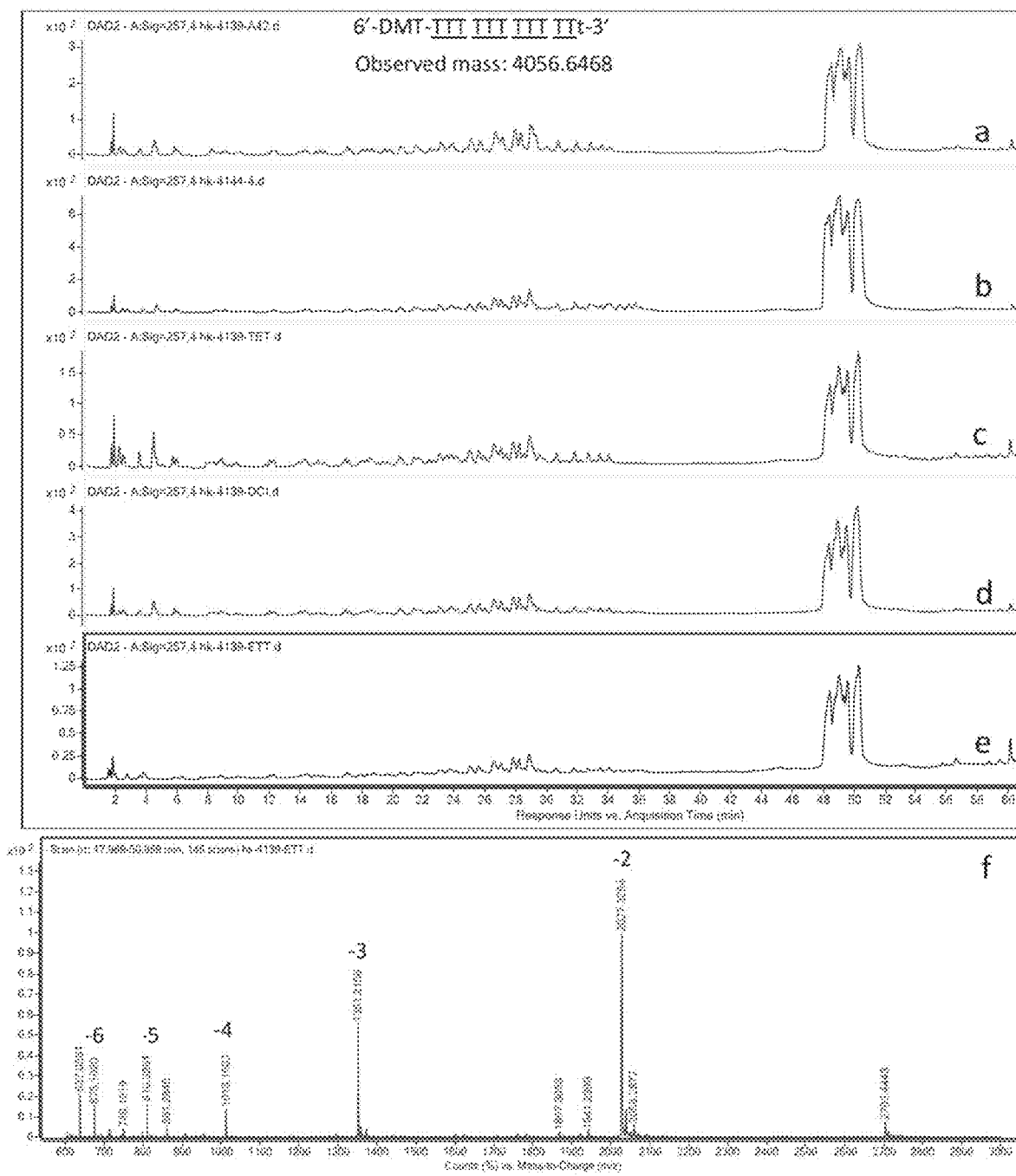
FIGS. 13A-F

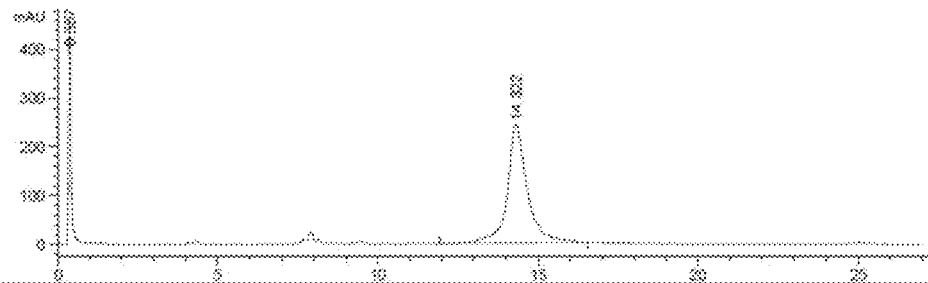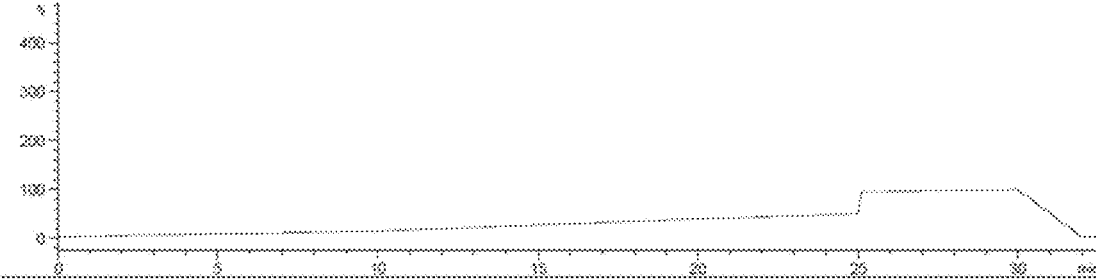
FIG. 33

THIOMORPHOLINO OLIGONUCLEOTIDES FOR THE TREATMENT OF MUSCULAR DYSTROPHY

CROSS REFERENCE TO RELATED APPLICATION

This U.S. Nonprovisional Application is a bypass continuation-in-part which claims the benefit of and priority to International Application No. PCT/US2018/051907, filed Sep. 20, 2018, which claims the benefit of and priority to U.S. Provisional Patent Application Ser. No. 62/562,162, filed Sep. 22, 2017, which is incorporated herein by reference.

SEQUENCE LISTING

The instant application contains a Sequence Listing which has been submitted electronically in ASCII format and is hereby incorporated by reference in its entirety. Said ASCII copy, created on Jul. 9, 2021, is named 90245.00282-2-Supplemental, and is 2 Kbytes in size.

TECHNICAL FIELD

This invention relates generally to the field of improved methods for treating muscular dystrophy in a patient. It also provides compositions suitable for facilitating exon skipping in a target gene, and preferably a human dystrophin gene.

BACKGROUND

Antisense compounds are being developed to correct or compensate for abnormal or disease-associated genes in a variety of indications. Antisense molecules inhibit gene expression with specificity, and because of this, many research efforts concerning oligonucleotides as modulators of gene expression have focused on inhibiting the expression of targeted genes or the function of cis-acting elements. But such techniques are not useful where the object is to up-regulate production of the native protein or compensate for mutations that induce premature termination of translation, such as nonsense or frame-shift mutations. In these cases, degradation or steric inhibition of the defective gene transcript will not compensate for the targeted mutation.

The exon splicing process is directed by complex multi-component machinery that brings adjacent exon-intron junctions in pre-mRNA into close proximity and performs cleavage of phosphodiester bonds at the ends of the introns with their subsequent reformation between exons that are to be spliced together. This complex and highly precise process is mediated by sequence motifs in the pre-mRNA that are relatively short, semi-conserved RNA segments to which various nuclear splicing factors that are then involved in the splicing reactions bind. By changing how the splicing machinery reads or recognizes the motifs involved in pre-mRNA processing, it is possible to create differentially spliced mRNA molecules. In this way, the effects of mutations on the eventual expression of a gene can be modulated through a process of targeted exon skipping during the splicing process.

The process of targeted exon skipping is likely to be particularly useful in long genes where there are many exons and introns, where there is redundancy in the genetic constitution of the exons or where a protein is able to function without one or more particular exons. Efforts to redirect gene processing for the treatment of genetic diseases associated with truncations caused by mutations in various genes have focused on the use of antisense oligonucleotides that either: (1) fully or partially overlap with the elements involved in the splicing process; or (2) bind to the pre-mRNA at a position sufficiently close to the element to disrupt the binding and function of the splicing factors that would normally mediate a particular splicing reaction which occurs at that element.

Duchenne muscular dystrophy (DMD) is caused by a defect in the expression of the protein dystrophin. The gene encoding the protein contains 79 exons spread out over more than 2 million nucleotides of DNA. Any exonic mutation that changes the reading frame of the exon, or introduces a stop codon, or is characterized by removal of an entire out of frame exon or exons, or duplications of one or more exons, has the potential to disrupt production of functional dystrophin, resulting in DMD. DMD, is a serious muscle wasting and invariably fatal genetic disease, mainly affecting boys, that leads to death in early adulthood. Individuals with DMD lack the protein dystrophin, which is required to strengthen and protect muscles. Lack of Dystrophin is, due to nonsense or frame shifting mutations that arise in one or more exons of the dystrophin (DMD) gene and ablating functional dystrophin expression. Two therapeutic AOs, such as Drisapersen (from Biomarin Inc) with 2'-O-Methyl phosphorothioate (2'-OMePS) chemistry and Eteplirsen (EXONDYS 51™ from Sarepta Therapeutics) with phosphorodiamidate mopholino (PMO) chemistry, which are designed to target exon-51 in DMD, have entered into Phase-III clinical trials. Drisapersen was rejected by the US FDA based on poor efficacy and toxicity issues, whereas Eteplirsen received an accelerated conditional approval for clinical use in September 2016.

Although one conventional PMO-based AO is currently in clinical use, there are some significant limitations associated with this chemistry. For example, current PMOs are incompatible with standard phosphoramidite chemistry to synthesize mixmer AOs with other well-established nucleotides analogs. In addition, the current PMO AOs are rapidly excreted through urine after the administration in vivo thereby requiring a high dose (30 mg/kg/week; 1.2 g/week for a 40 kg patient) that ultimately makes this drug exorbitantly expensive. Another significant limitation with current PMO AOs is their inability to complex with currently available transfection reagents for rapid cellular studies in vitro because of their neutral charge.

Thus, there remains a need for improved compositions and methods for treating muscular dystrophy in patients.

SUMMARY OF THE INVENTION

The inventors have developed a novel morpholino chemistry to overcome the limitations associated with current PMO AOs.

The present disclosure provides antisense oligonucleotides (ODNs) comprising thiomorpholino nucleotides effective to treat or prevent the progression of muscular dystrophy in a mammal in need of such treatment. These thiomorpholino-containing nucleotides (TMOs) may cause exon skipping in exons (including human exon 51) of the transcripts of the dystrophin gene during RNA processing, similar to the antisense oligonucleotide Eteplirsen, but with longer serum half-life, with substantially less complicated production methods, and ultimately with less expensive therapeutic compositions and administration regimens.

Particularly useful TMOs of this disclosure include the antisense ODNs 1147, 1148, 1153, and 1154 (base sequences and internucleotide linkages shown in FIGS. 1C and 1D) that are effective in exon 23 skipping in the H2K dmd mdx mouse.

Accordingly, this disclosure also provides methods of treating muscular dystrophy, and Duchenne muscular dystrophy (DMD) in particular, in patients by administering an effective amount of a TMO composition of this disclosure that is complementary to a target region in an exon of the human dystrophin gene to specifically hybridize to the target region, induce exon skipping, and thereby treat the muscular dystrophy. The administration of such TMOs will be sufficient to increase the number of dystrophin-positive fibers in a subject to stabilize, maintain, or improve walking distance in the patient relative to a healthy subject who does not suffer from a muscular dystrophy.

In these methods, the TMOs of this disclosure may be administered in a dose and for a time period to thereby increase the number of dystrophin-positive fibers in a subject to at least 20%, about 30%, about 40%, about 50%, about 60%, about 70%, about 80%, about 90%, or about 95% of dystrophin-positive fibers present in a healthy subject who does not suffer from a muscular dystrophy.

In these methods, the TMOs of this disclosure may be administered by systemic administration, such as once weekly or bimonthly, by infusion.

These methods may comprise methods of treating muscular dystrophy in a patient by administering a composition comprising an antisense TMO of this disclosure of between 20 to 50 nucleotides in length comprising at least 10 consecutive nucleotides complementary to a target region in an exon of the human dystrophin gene, wherein the antisense oligonucleotide specifically hybridizes to the target region inducing exon skipping, thereby treating the muscular dystrophy in the subject.

In these methods, the antisense TMO may be complementary to a target region in an exon of the human dystrophin gene selected from the group consisting of exon 23, exon 51, exon 50, exon 53, exon 45, exon 46, exon 44, exon 52, exon 55 and exon 8.

In these methods, the antisense oligonucleotide is 8 to 20, 20 to 50, 30 to 50, or 20 to 30 nucleotides in length.

In these methods, the antisense TMOs may be chemically linked to one or more moieties or conjugates that enhance the activity, cellular distribution, or cellular uptake of the antisense oligonucleotide, such as an arginine-rich peptide.

Thus, this disclosure also provides unique antisense oligonucleotides containing at least one thiomorpholino nucleotide, as well as pharmaceutical compositions comprising such TMOs and one or more pharmaceutical excipients.

In one embodiment, the invention includes a method of treating muscular dystrophy in a human subject comprising administering a composition comprising an antisense oligonucleotide of 8 to 50 nucleotides in length, comprising at least 1 thiomorpholino nucleotide, and comprising at least 8 to 10 consecutive nucleotides complementary to a target region in an exon of the human dystrophin gene, wherein the antisense oligonucleotide specifically hybridizes to the target region inducing exon skipping, thereby treating muscular dystrophy in the subject. wherein the antisense oligonucleotide is:

5'-$T_oC_oA_oA_oG_oG_oA_oA_oG_oA_oT_oG_oG_oC_oA_oT_oT_oT_oC_o$t-3' (SEQ ID NO. 4)

5'-$A_oG_oG_oA_oA_oG_oA_oT_oG_oG_oC_oA_oT_oT_oT_o$c-3' (SEQ ID NO. 5)

(o) indicates optional thiomorpholino internucleotide linkage; where upper case letters represent thiomorpholino nucleotides and lower case letters represent a 2'-deoxynucleoside. The terminal 3' nucleoside can be a 2'-deoxynucleoside, a ribonucleoside, a morpholino nucleoside, or a 2'-modified ribonucleoside, and wherein said antisense oligonucleotide facilitates exon skipping on the transcripts of the human dystrophin gene during RNA processing in a human subject in need thereof.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become more readily apparent from the Description of Embodiments, particularly when taken together with the drawings.

BRIEF DESCRIPTION OF FIGURES

FIG. 1C shows the design of the thiomorpholino ODNs (TMOs) used to study exon 23 skipping with H2K mdx cells in a mouse model. The design depicts thiomorpholino and thiomorpholino/DNA chimeras for induction of exon-23 skipping in the Dmd transcript of H-$2K^b$-tsA58 mdx mouse myotubes. In the exemplary ODN sequences presented, thiomorpholino and thiophosphate internucleotide linkages are indicated by asterisk (*); morpholino and 2' deoxyribonucleosides are indicated by upper-case and lower-case letters, respectively; 2'O-methyl uridine nucleotides are indicated by "u-2'-OMe." Each of the ODNs has the same sequences of bases [ggccaaacctcggcttaccn; SEQ ID NO:2, wherein the terminal 'n' is modified base 2'-O-methyluridine (um)], with the exception of the 2'-Ome PS control, which has the same base sequences but replaces the thymine bases with uridine bases [ggccaaaccucggcuuaccn; SEQ ID NO:3, wherein the terminal 'n' is modified base 2'-O-methyluridine (um)]. For the PMO control, the asterisk represents the N,N-dimethylphosphordiamidate as shown in FIG. 1D.

FIG. 1D shows the chemical structures of the internucleotide linkages formed in the ODNs depicted in 1C. In the left panel, the chemical structure of the internucleotide linkages existing in ODNs 1147, 1148, 1153, and 1154 are depicted: in the middle panel, the internucleotide linkage existing in the PMO control compound is depicted. In the right panel, the internucleotide linkage existing in the 2'-Ome PS control compound is depicted.

```
Drisapersen:
5'-UCA AGG AAG AUG GCA UUU CU-3'

ODN-R1:
5'-TCA AGG AAG ATG GCA TTT CU-3'

16-mer control:
5'-AGG AAG AUG GCA UUU C-3';

ODN-R2:
5'-AGG AAG ATG GCA TTT C-3'

+ve (Exondys 51 2'-OMePS):
5'-CUC CAA CAU CAA GGA AGA UGG
   CAU UUC UAG-3'  (400 nM)

(*BOLD 2'-OMe monomer)
(**Italic TMO monomer)
```

Figure 9A:
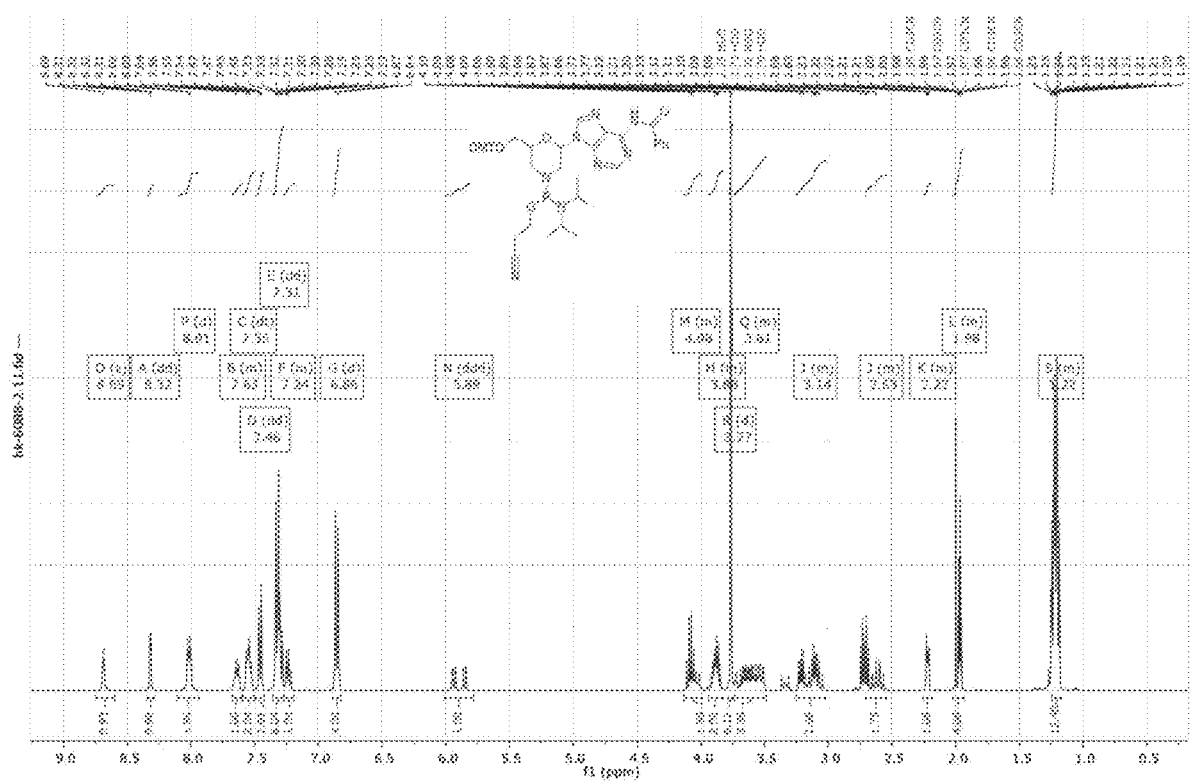
Figure 9B:
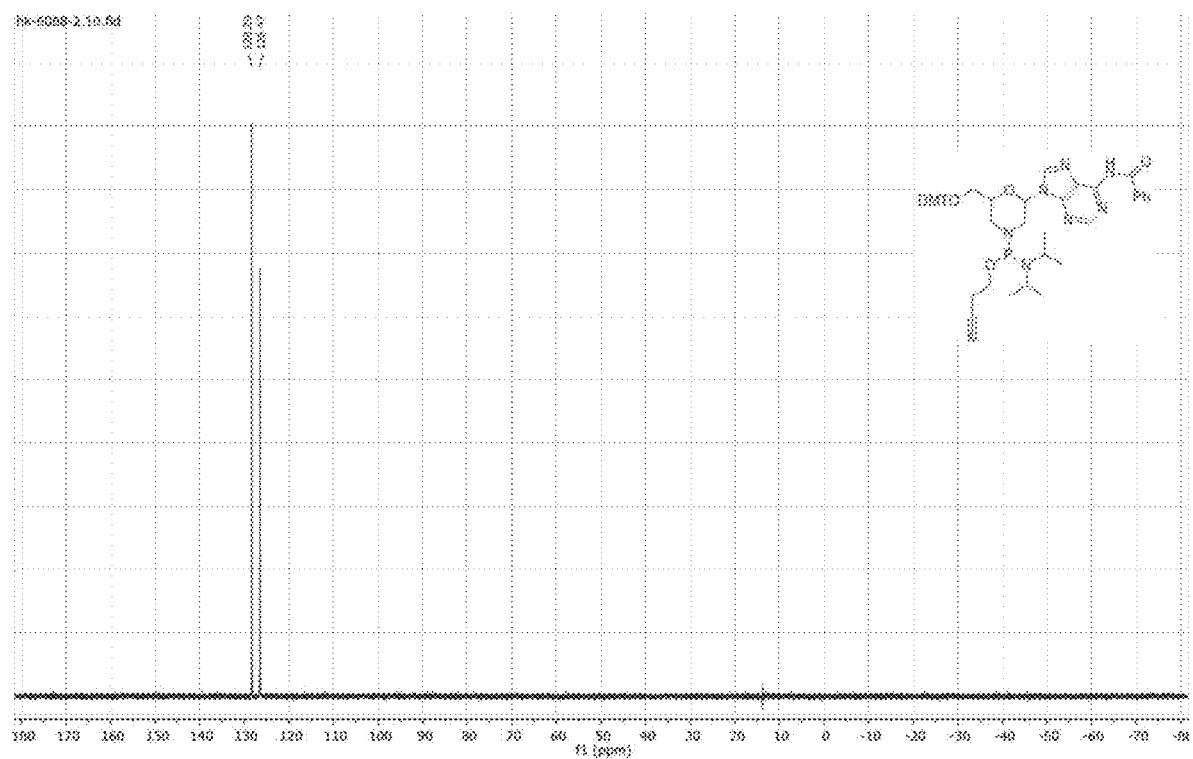
Figure 9C:
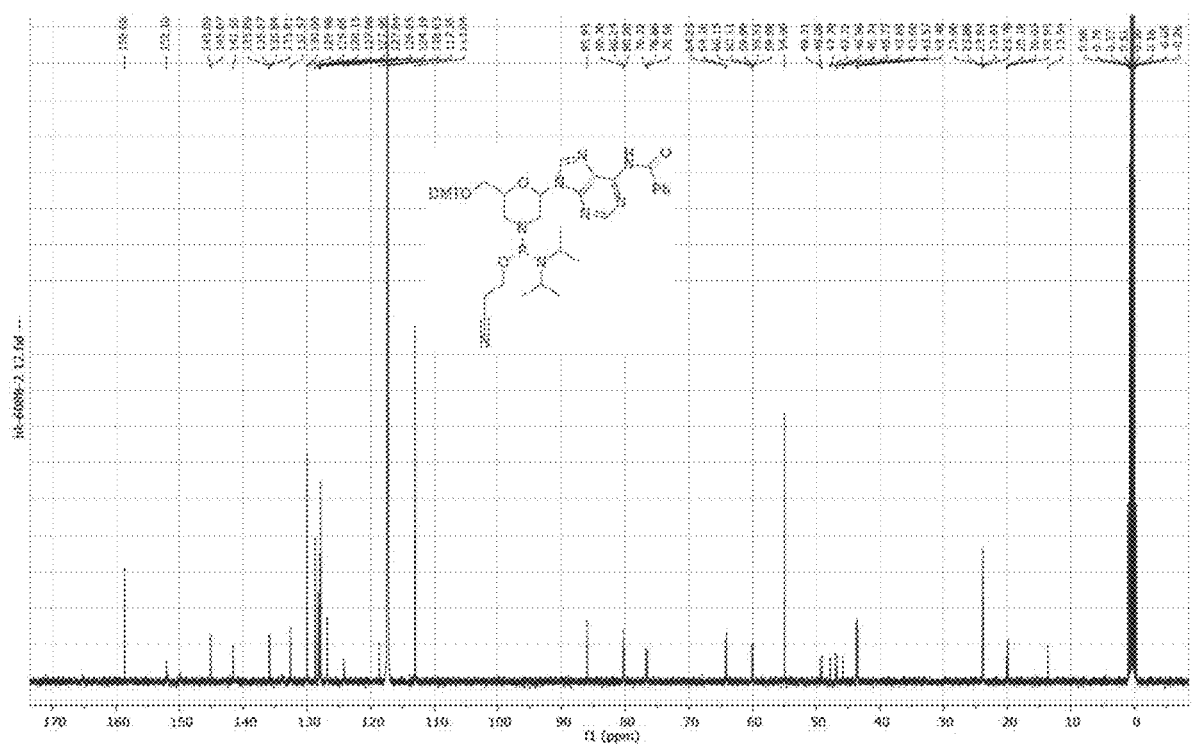

FIGS. 9A-C shows (A) $^1$H NMR, (B) $^{13}$C NMR, and (C) $^{31}$P NMR data demonstrating the synthesis of compound 4a: 5'-O-(4,4'-Dimethoxytrityl)-3'-O-cyanoethyl-2'-deoxyadenosine morpholino phosphorodiamidate.

Figure 10A:
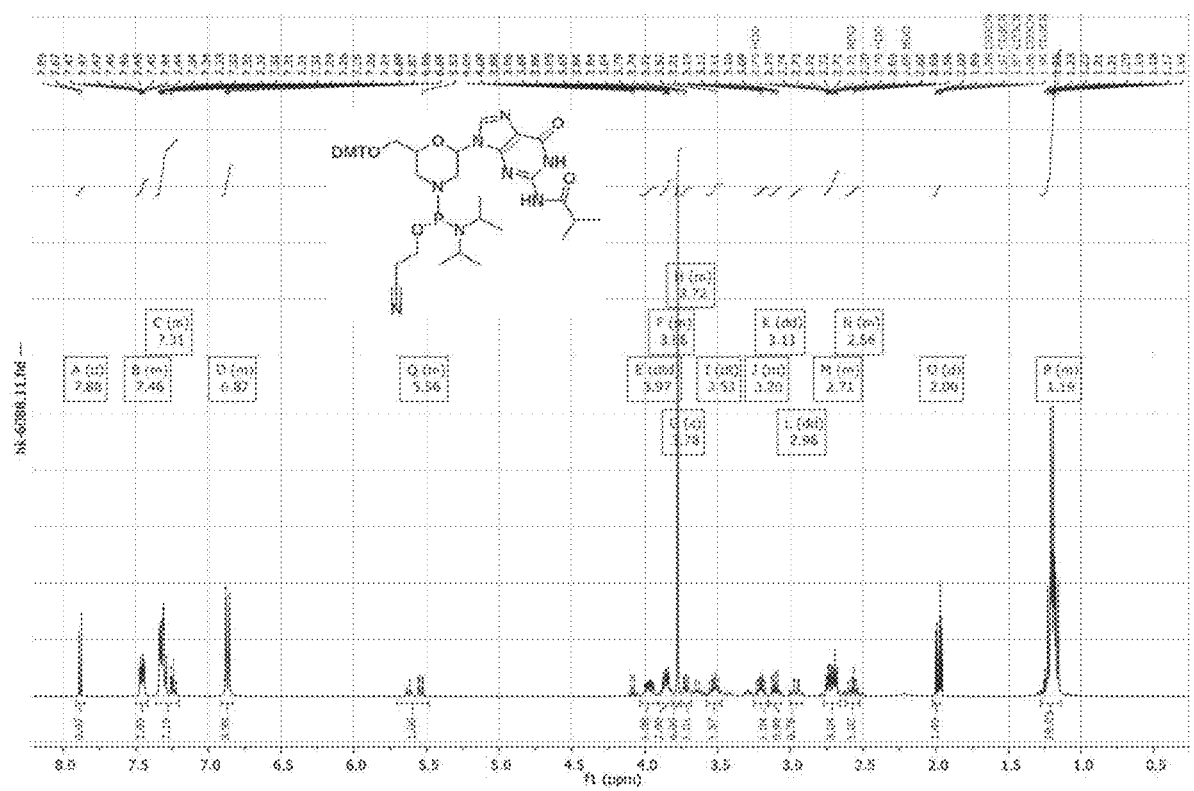
Figure 10B:
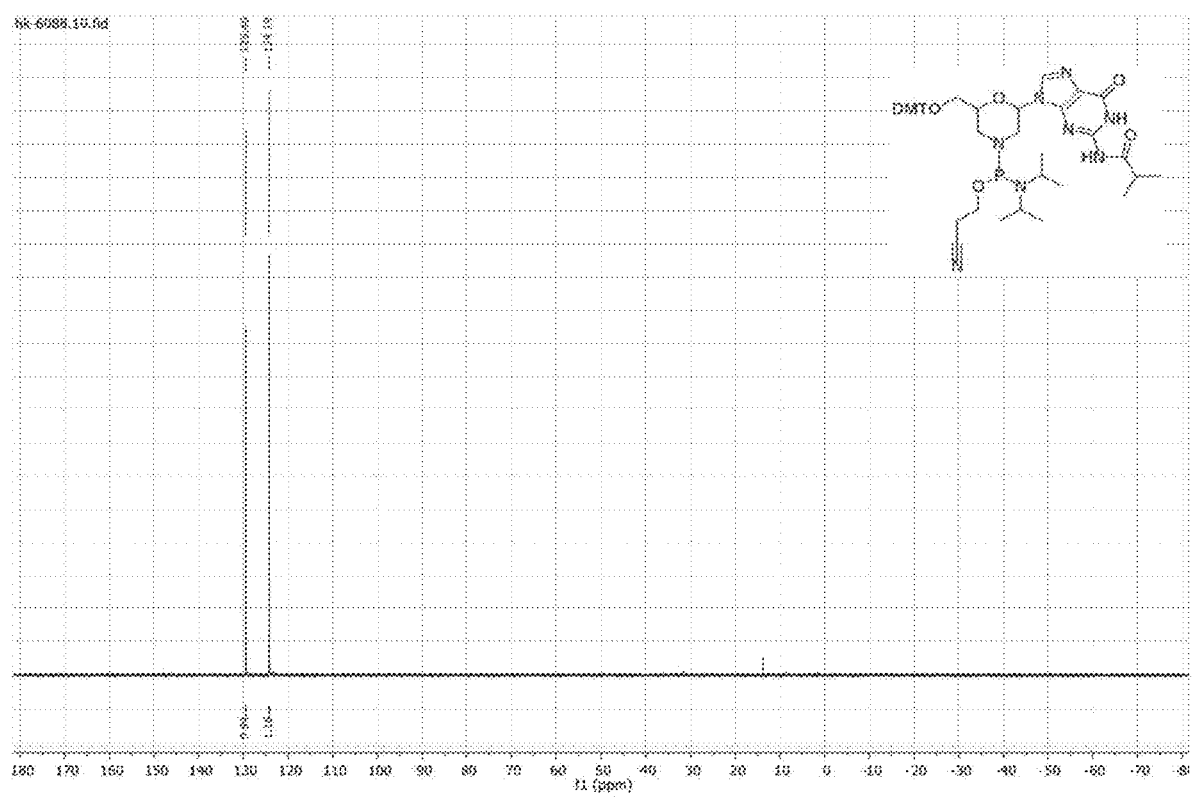
Figure 10C:
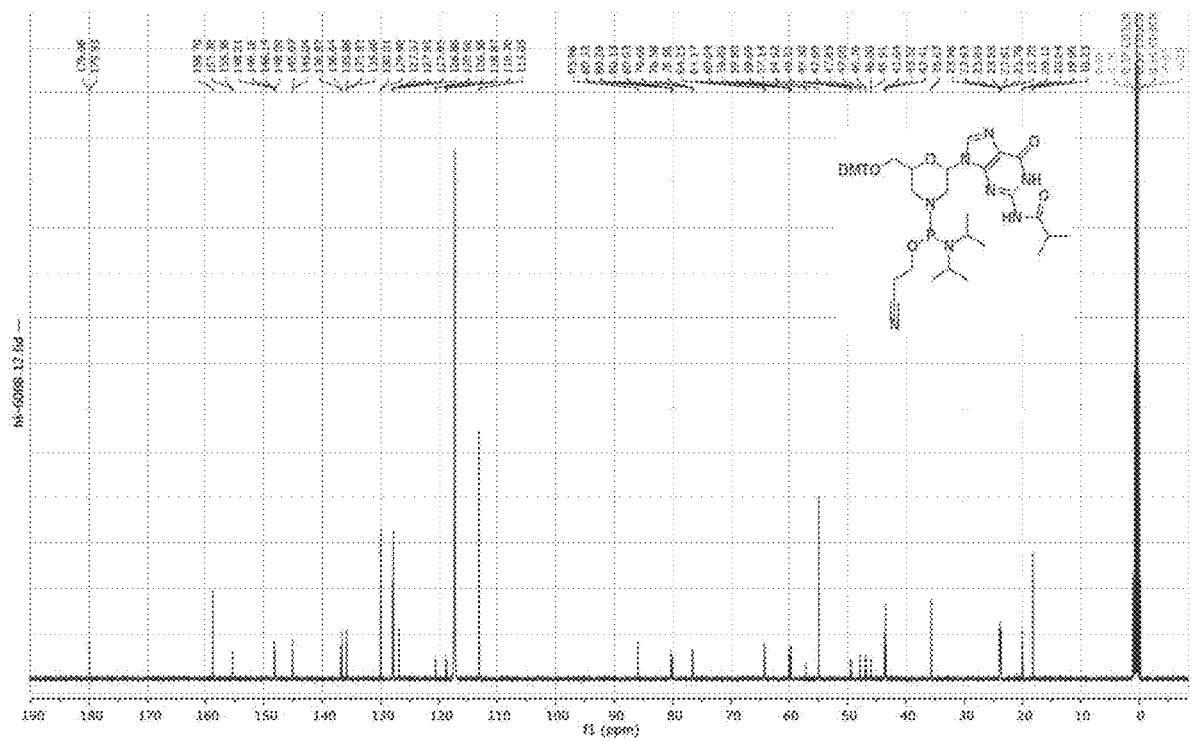

FIGS. 10A-C shows (A) $^1$H NMR, (B) $^{13}$C NMR, and (C) $^{31}$P NMR data demonstrating the synthesis of compound 4b: 5'-O-(4,4'-Dimethoxytrityl)-3'-O-cyanoethyl-2'-deoxyguanosine morpholino phosphorodiamidate.

Figure 11A:
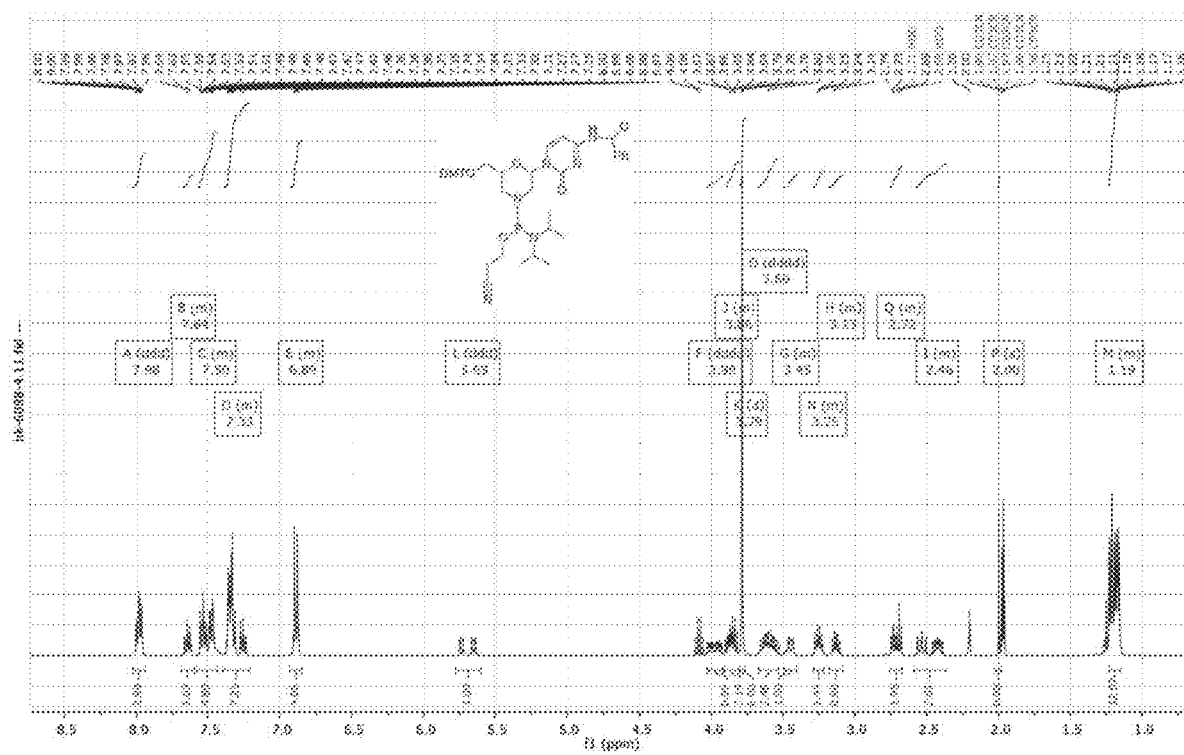
Figure 11B:
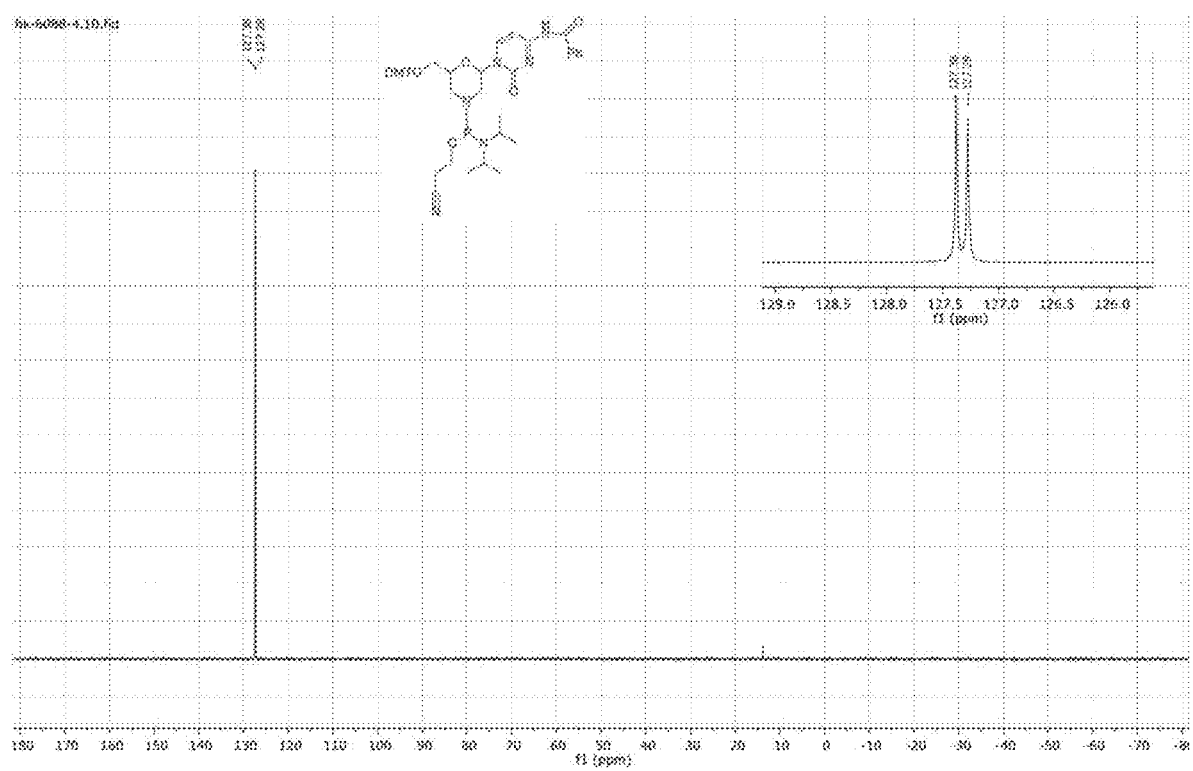
Figure 11C:
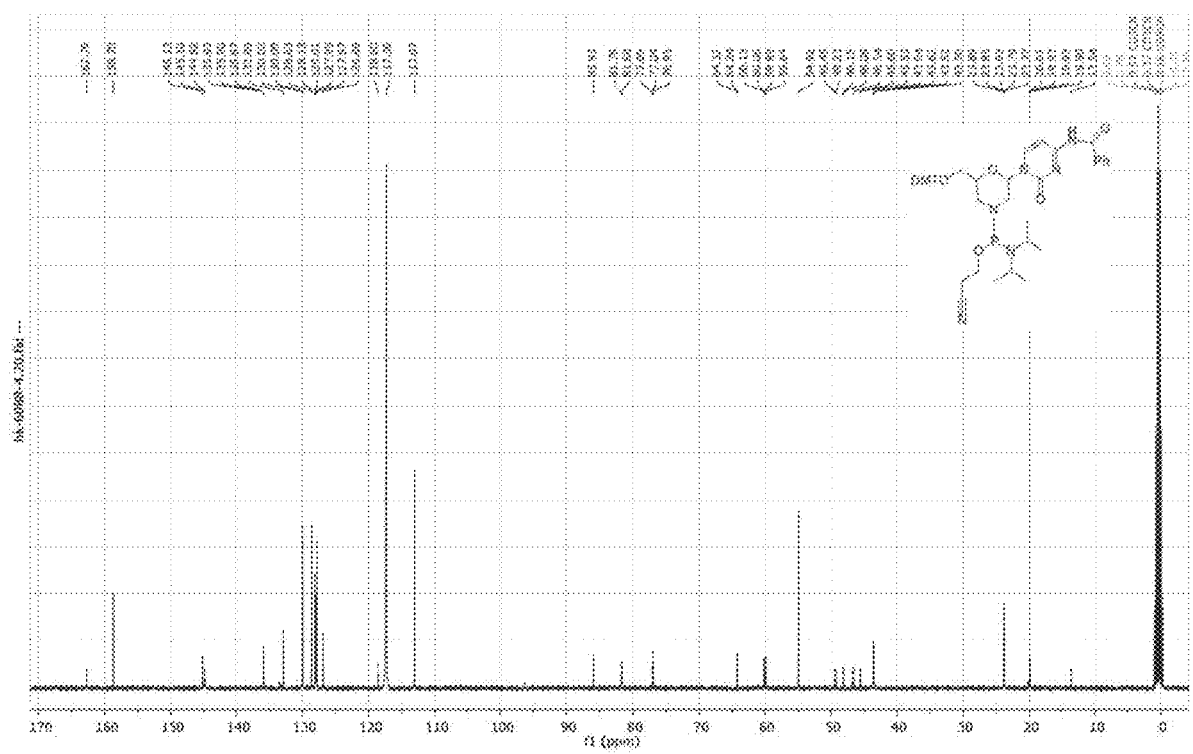

FIGS. 11A-C shows (A) $^1$H NMR, (B) $^{13}$C NMR, and (C) $^{31}$P NMR data demonstrating the synthesis of compound 4c: 5'-O-(4,4'-Dimethoxytrityl)-3'-O-cyanoethyl-2'-deoxycytidine morpholino phosphorodiamidate.

Figure 12A:
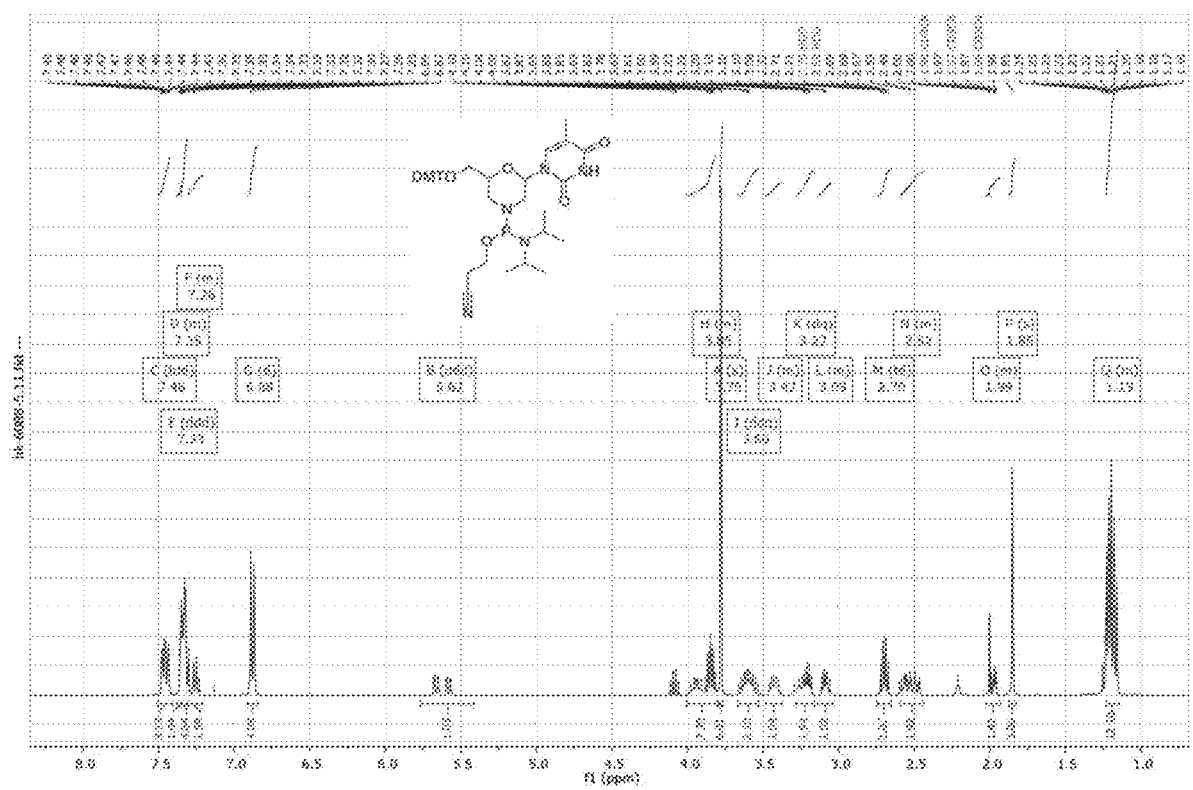
Figure 12B:
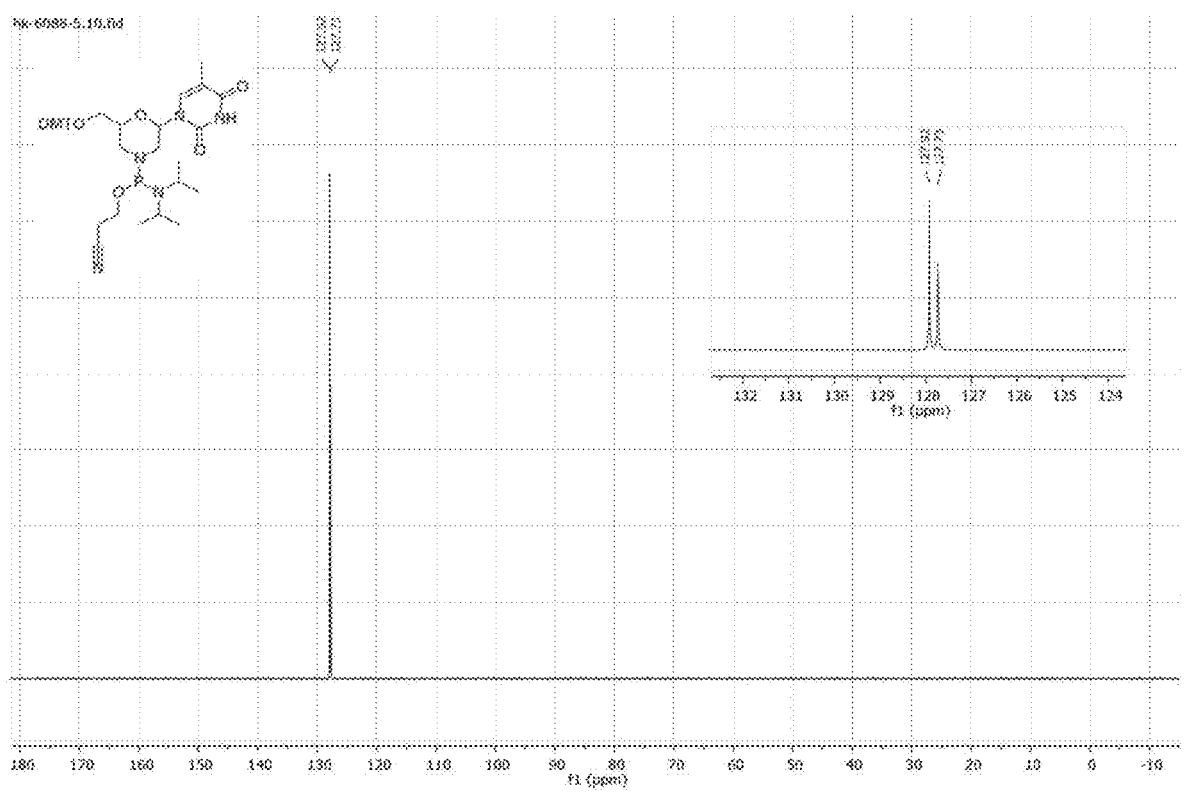
Figure 12C:
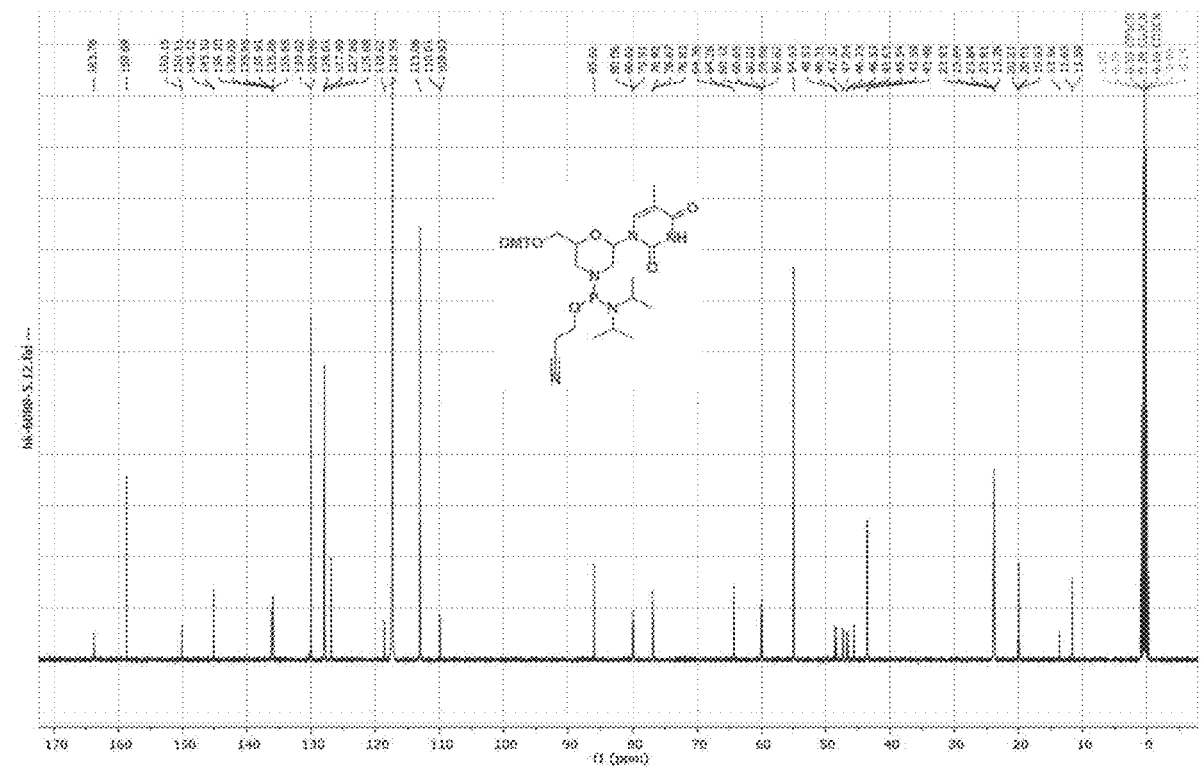

FIGS. 12A-C shows (A) $^1$H NMR, (B) $^{13}$C NMR, and (C) $^{31}$P NMR data demonstrating the synthesis of compound 4d: 5'-O-(4,4'-Dimethoxytrityl)-3'-O-cyanoethyl-2'-deoxythymidine morpholino phosphorodiamidate.

FIGS. 13A-F shows a comparison of LCMS (TIC) profiles of crude 12-mer ODN1 (Table 1) synthesized using various activators. Solid-phase synthesis using (a) 0.12 M Activator 42® (b) 0.12 M ETT buffered with 0.01 M DMAP (c) 0.20 M Tetrazole (d) 0.12 M 4,5-Dicyanoimidazole (e) 0.12 M 5-Ethylthio-1H-Tetrazole (f) Mass spectrum (600-3000 m/z) of crude reaction mixture (peak at retention times: 47.9-50.9 min, 145 scans) from synthesis (e).

Figure 14:
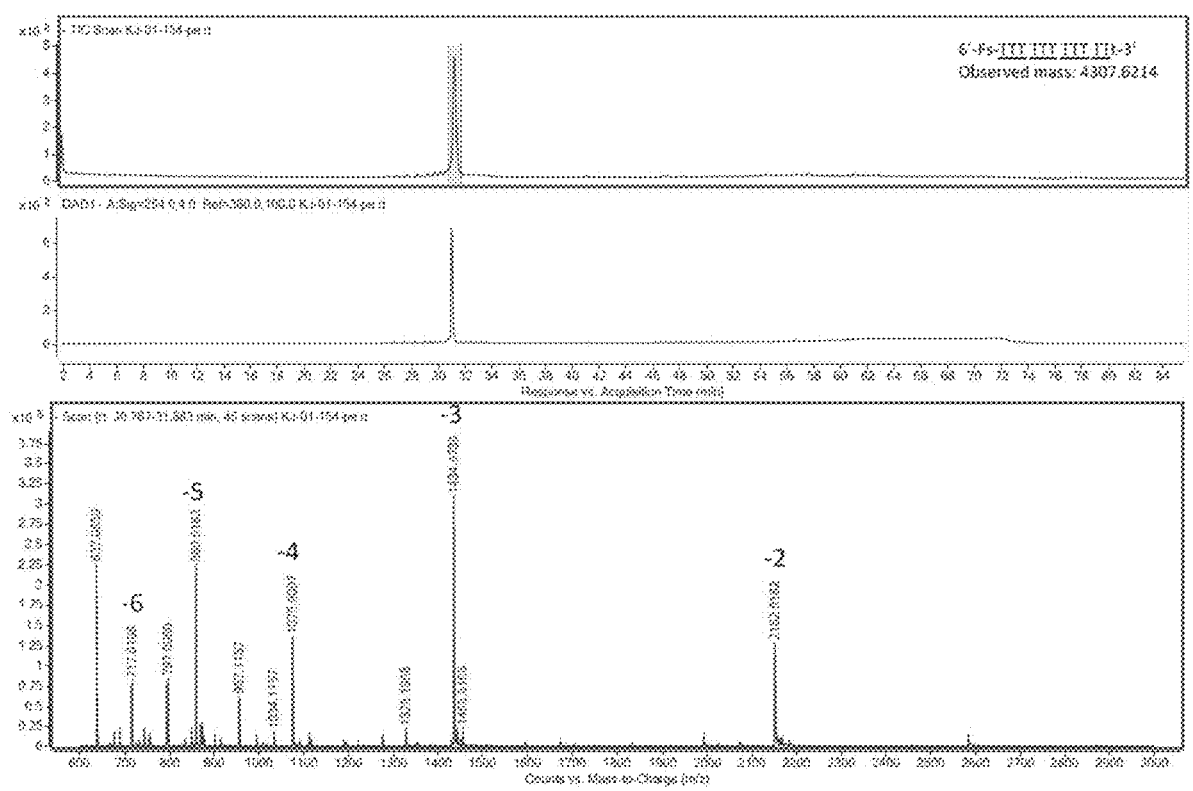
Figure 15:
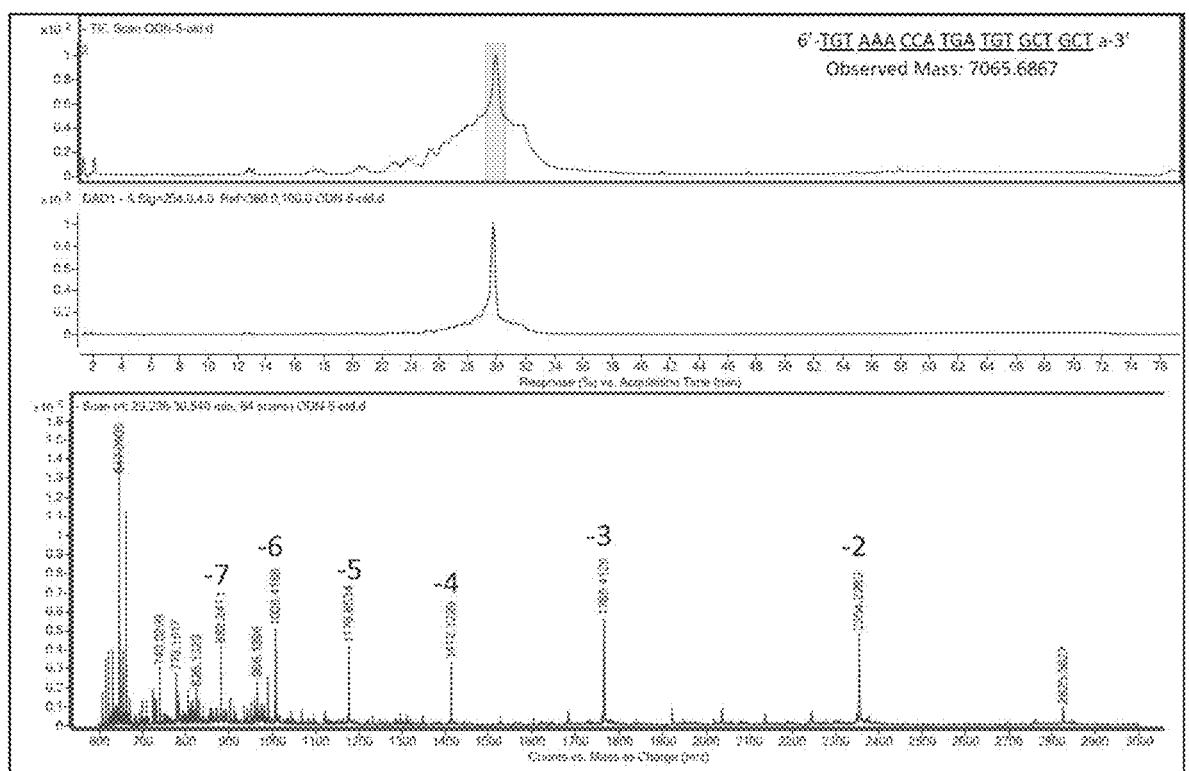
Figure 16:
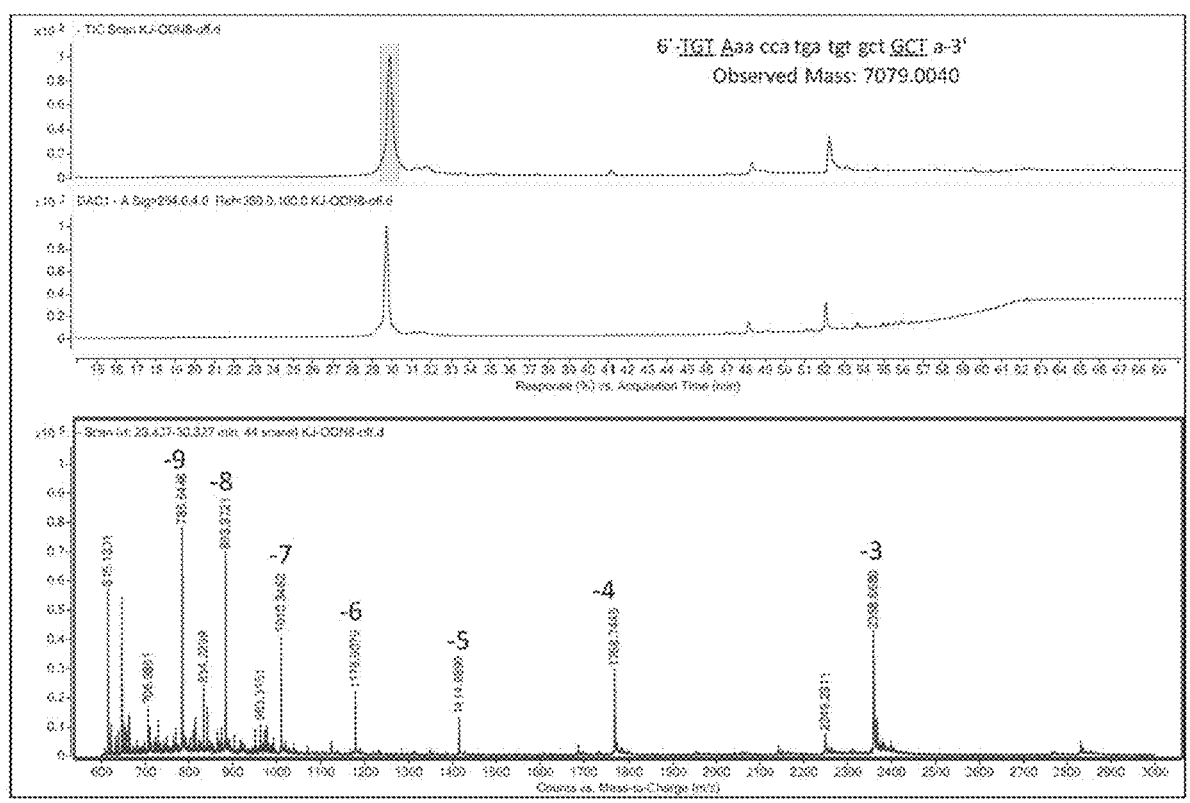
Figure 17:
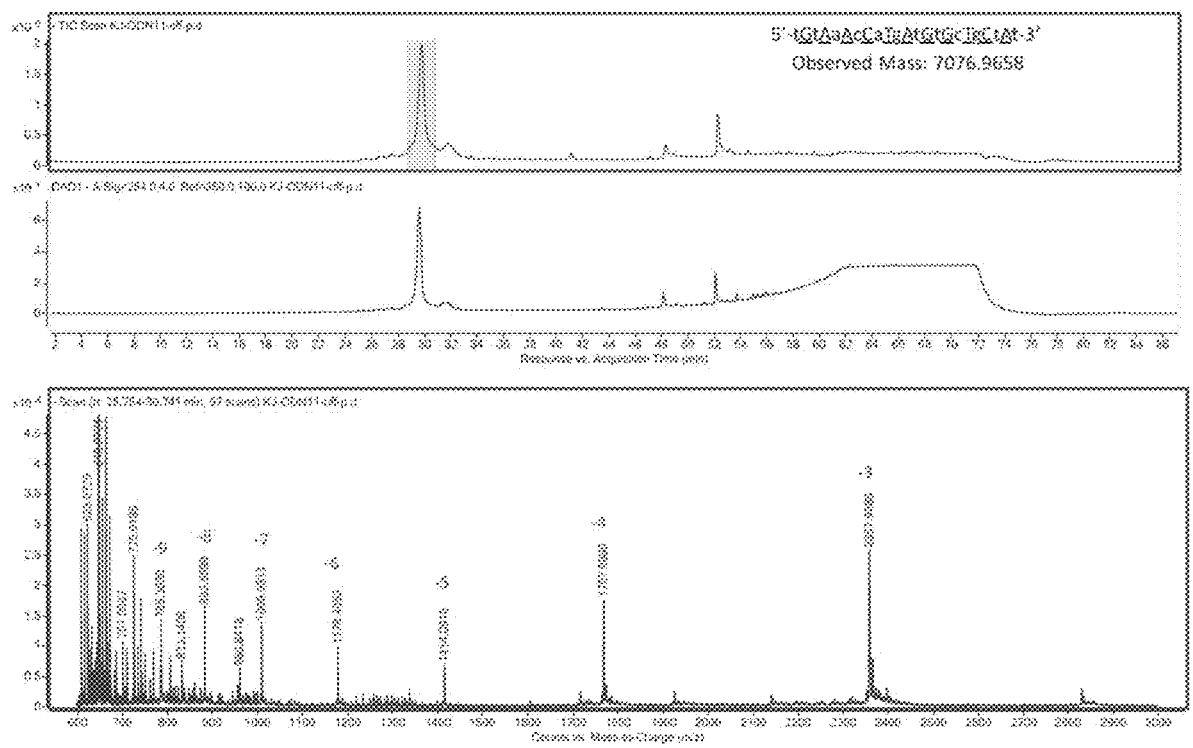
Figure 18:
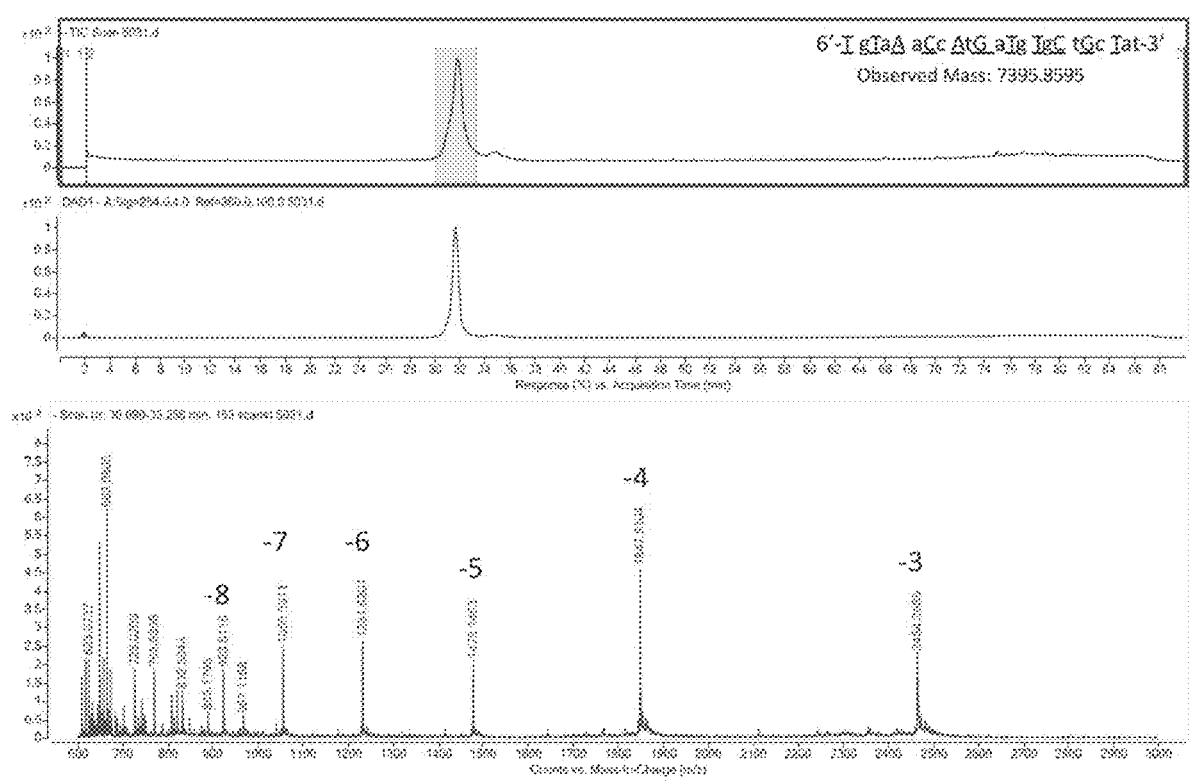
Figure 19:
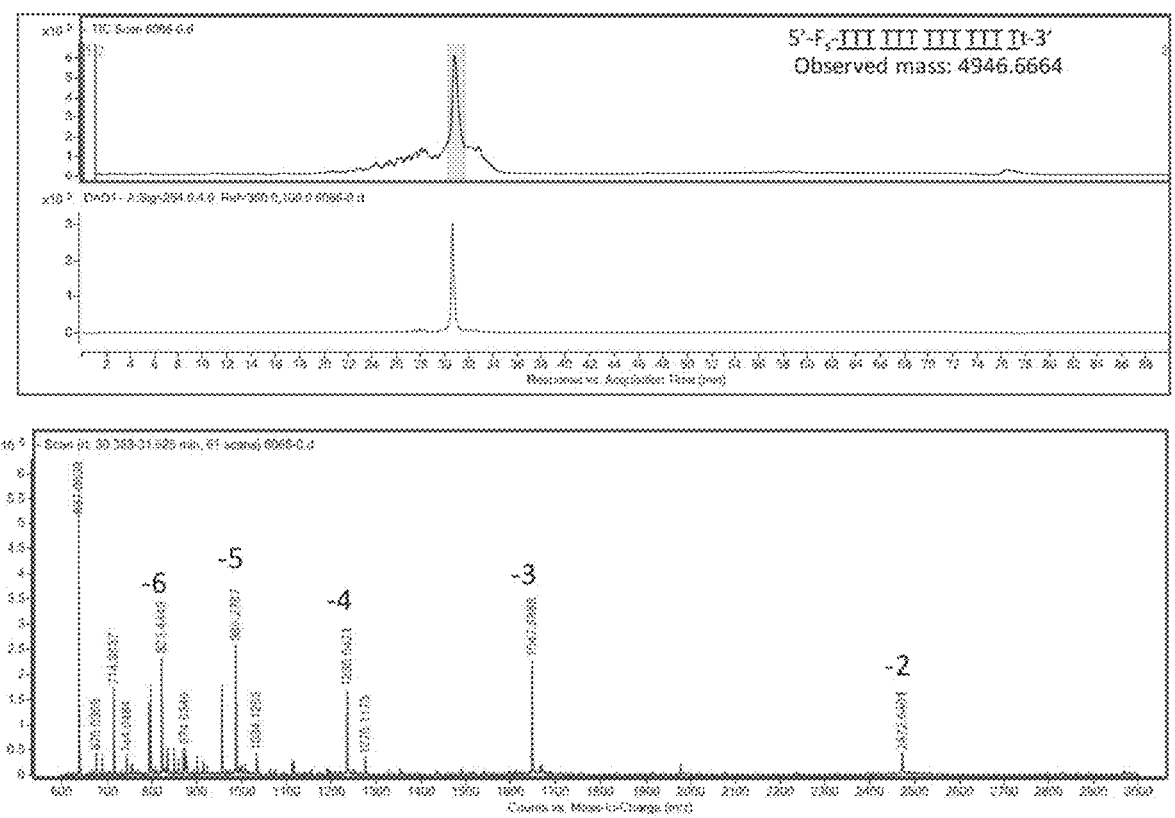
Figure 20:
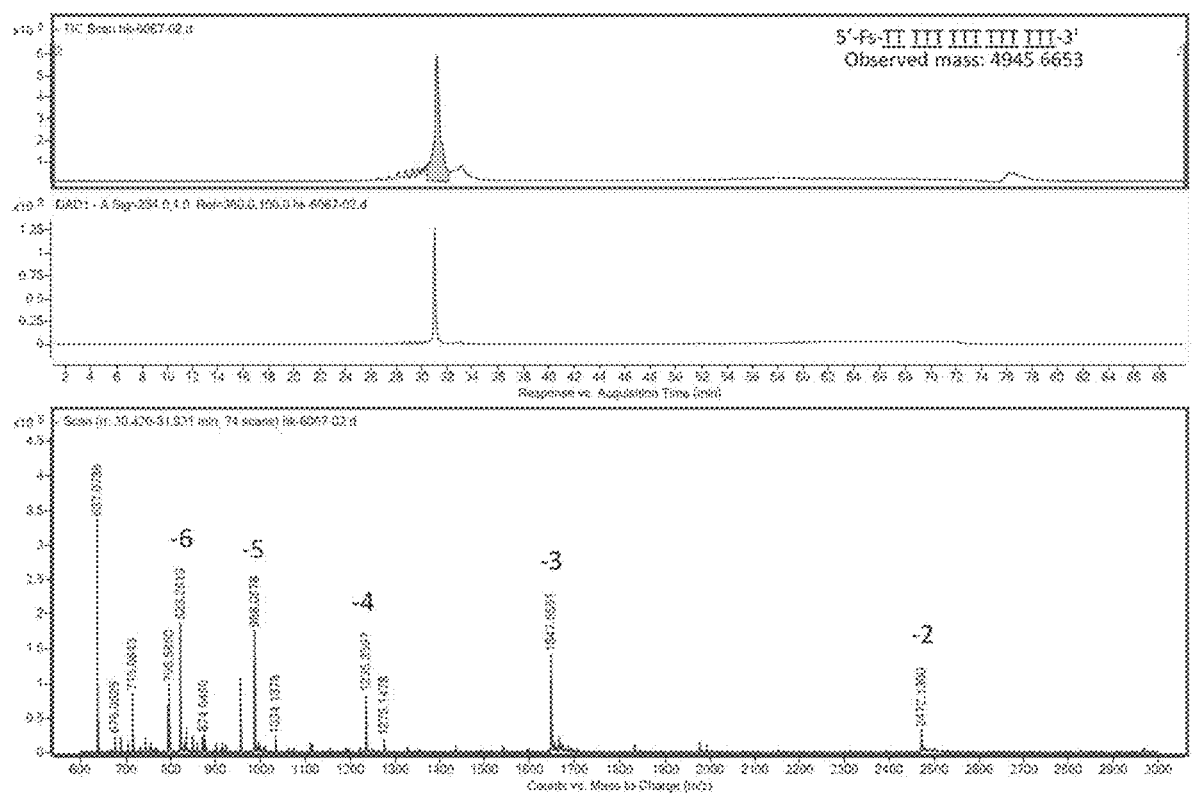
Figure 21:
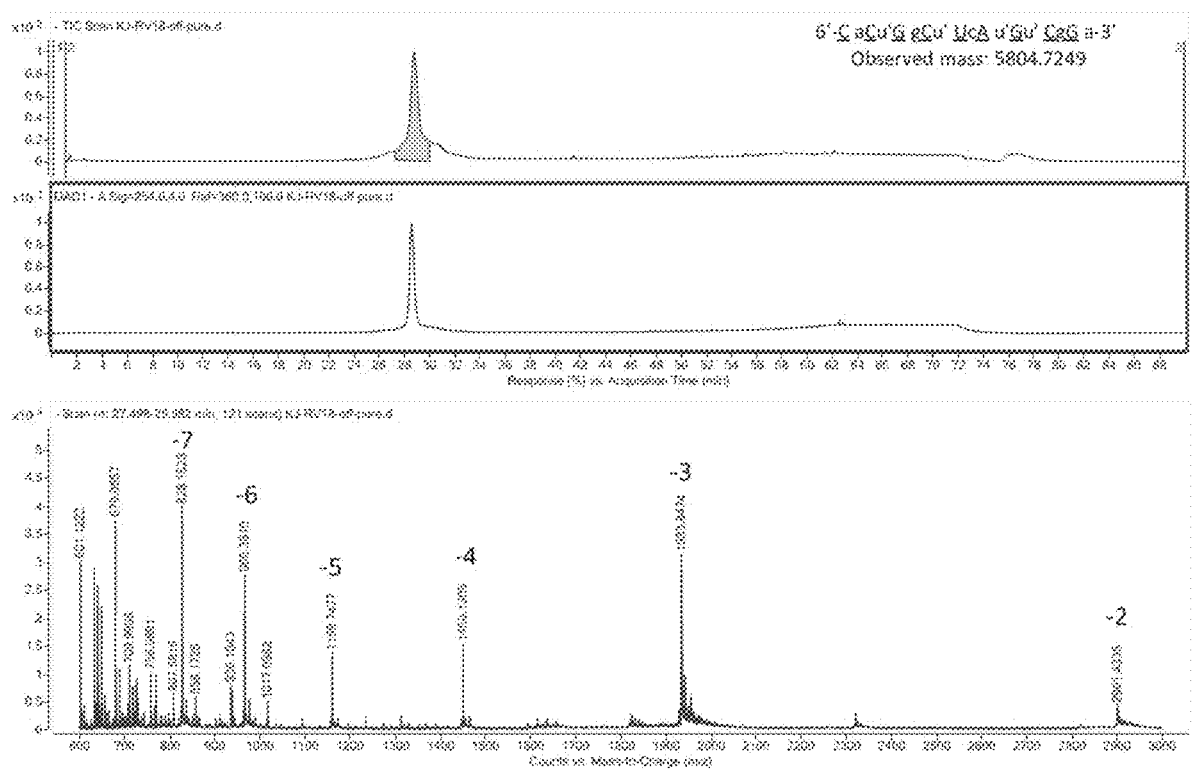
Figure 22:
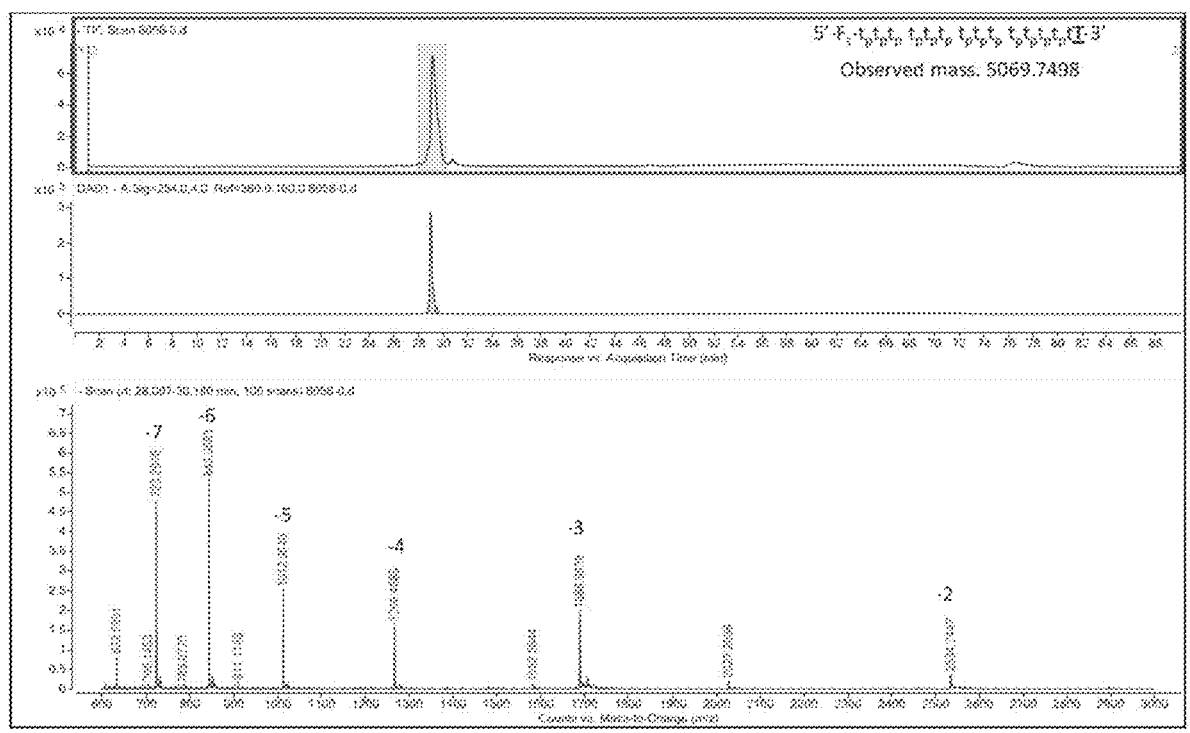
Figure 23:
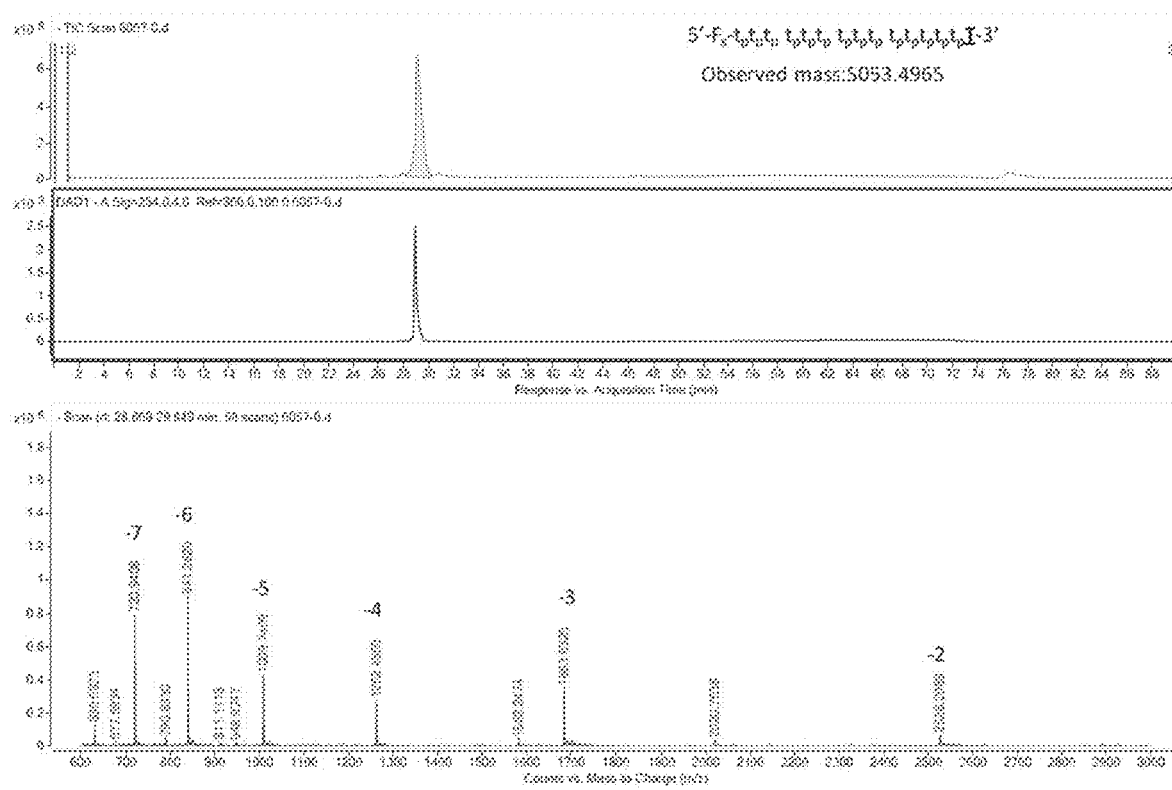
Figure 24:
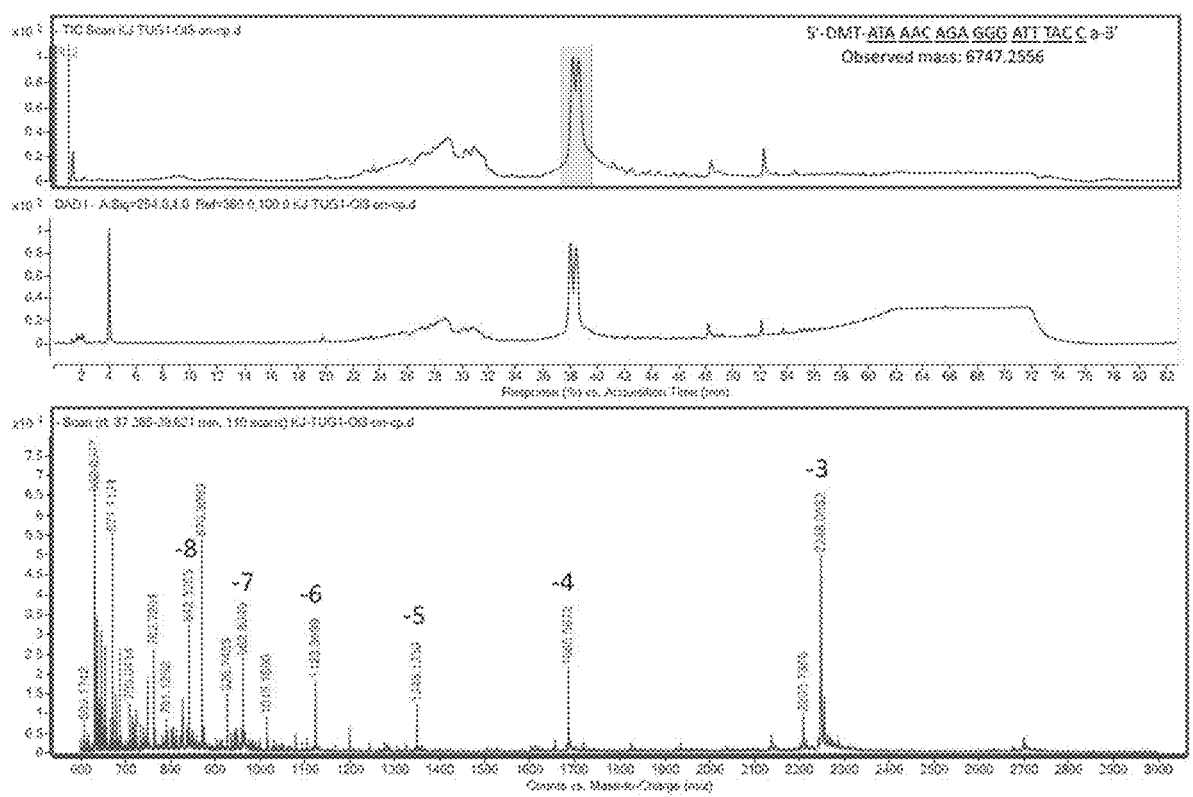
Figure 25:
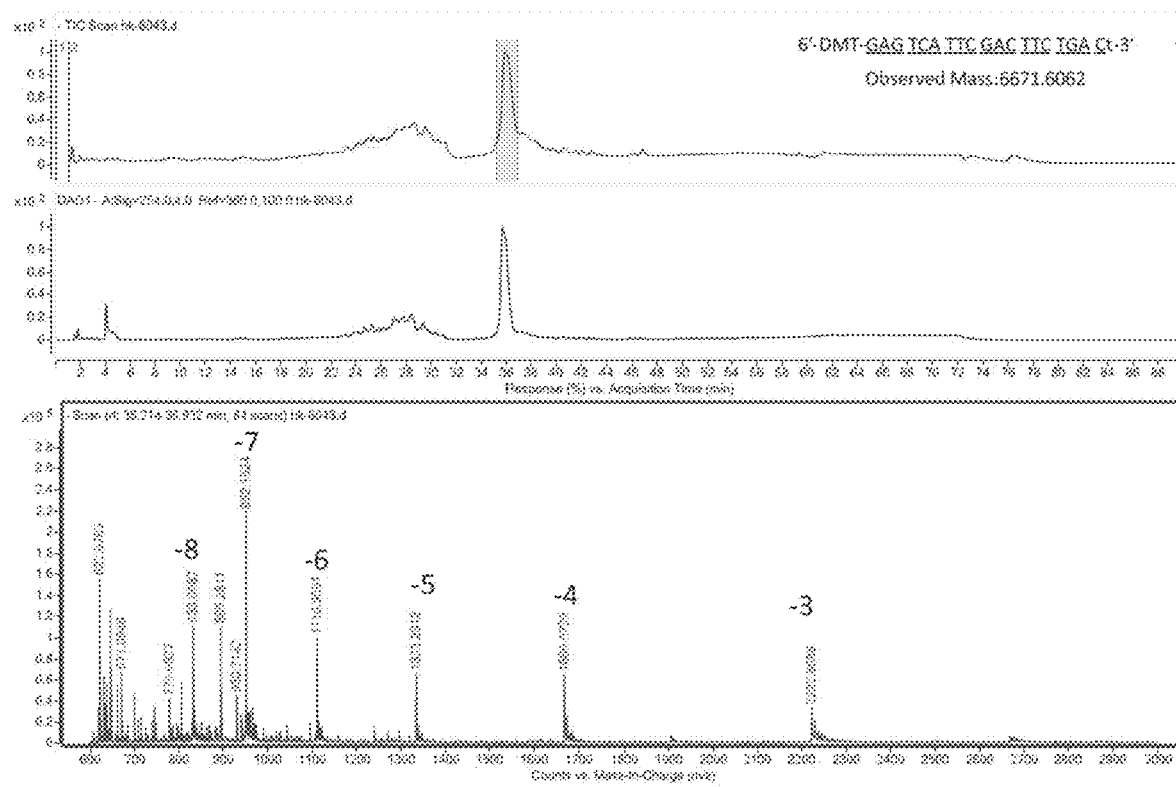
Figure 26:
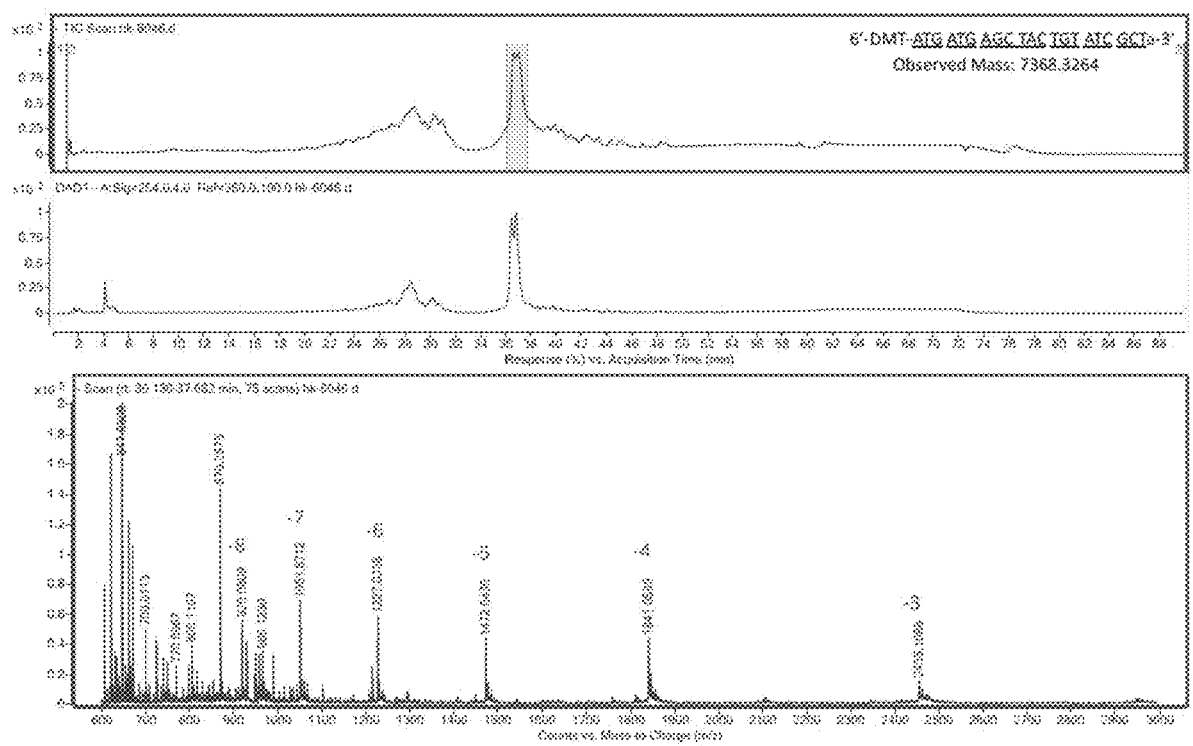
Figure 27:
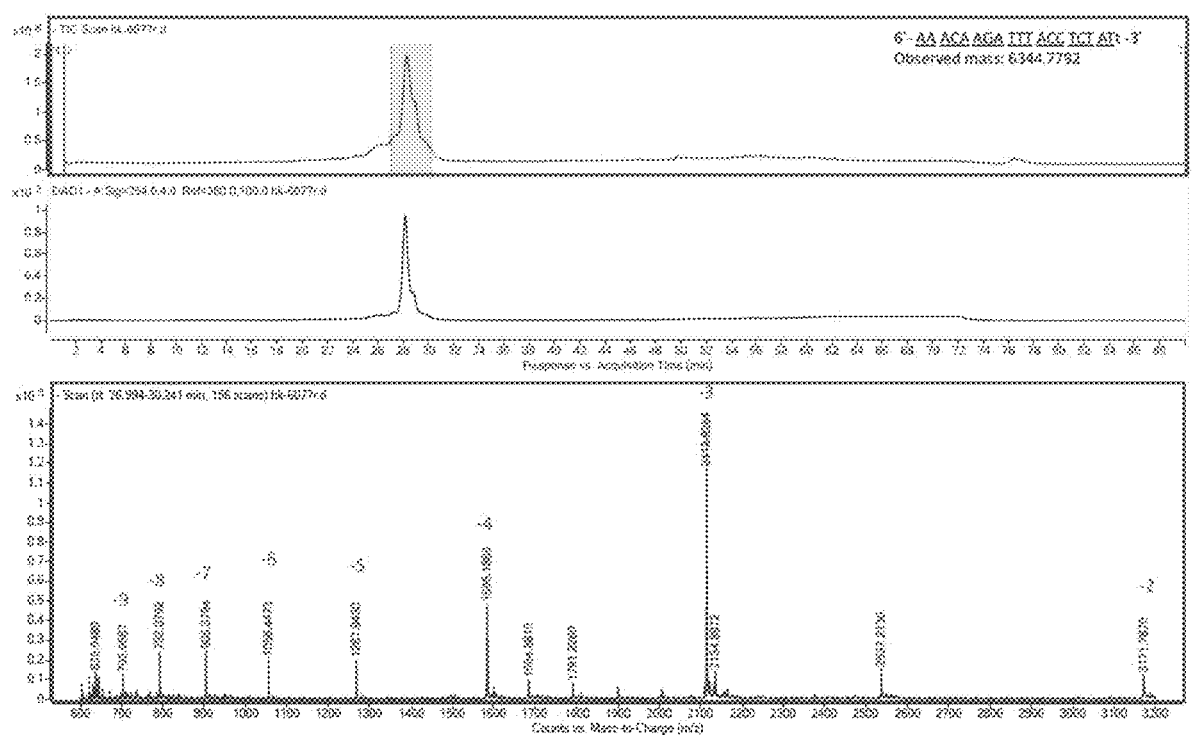

FIG. 14 shows LCMS analysis of HPLC purified ODN 2.
FIG. 15 shows LCMS analysis of HPLC purified ODN 3.
FIG. 16 shows LCMS analysis of HPLC purified ODN 4.
FIG. 17 shows LCMS analysis of HPLC purified ODN 5.
FIG. 18 shows LCMS analysis of HPLC purified ODN 6.
FIG. 19 shows LCMS analysis of HPLC purified ODN 7.
FIG. 20 shows LCMS analysis of HPLC purified ODN 8.
FIG. 21 shows LCMS analysis of HPLC purified ODN 9.
FIG. 22 shows LCMS analysis of HPLC purified ODN 10.
FIG. 23 shows LCMS analysis of HPLC purified ODN 11.
FIG. 24 shows LCMS analysis of crude sample of ODN 14 prior to HPLC purification FIG. 25 shows LCMS analysis of crude sample of ODN 15 prior to HPLC purification
FIG. 26 shows LCMS analysis of crude sample of ODN 16 prior to HPLC purification
FIG. 27 shows LCMS analysis of HPLC purified ODN 17

Figure 28:
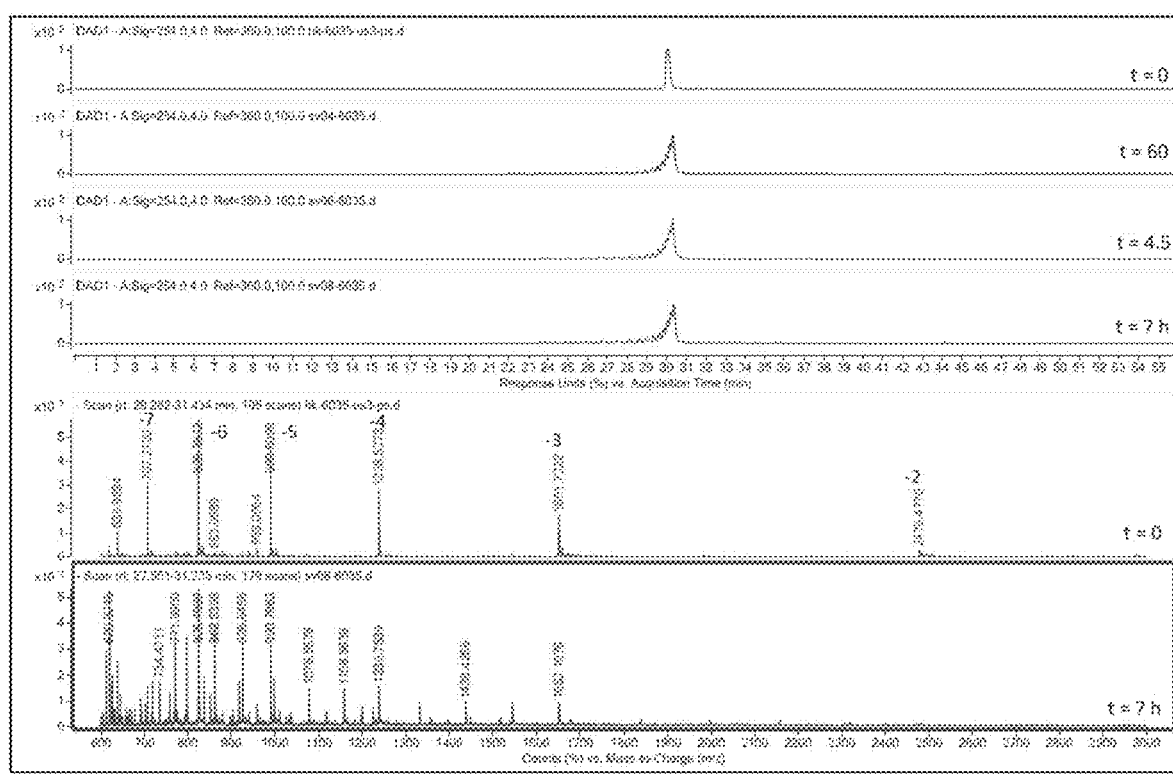

FIG. 28 shows time-dependent enzymatic hydrolysis of pS-DNA control (ODN 12, Table 1) in presence of svPDE enzyme (100 mM Tris pH 9, 14 mM MgCl$_2$, 72 mM NaCl, 13.3 µM ODN, 1×10$^{-1}$ U/mL svPDE enzyme). (a) UV profile over time as observed during LCMS of higher Rt peak at each time point is shown. (b) TIC of ODN 12 (105 scans from Rt=29.3-31.4 min of UV profile, m/z=600-3000 range) before enzymatic degradation and after svPDE treatment for t=7 h (179 scans from Rt=27.5-31.2 min of UV profile, m/z=600-3000 range).

Figure 29:
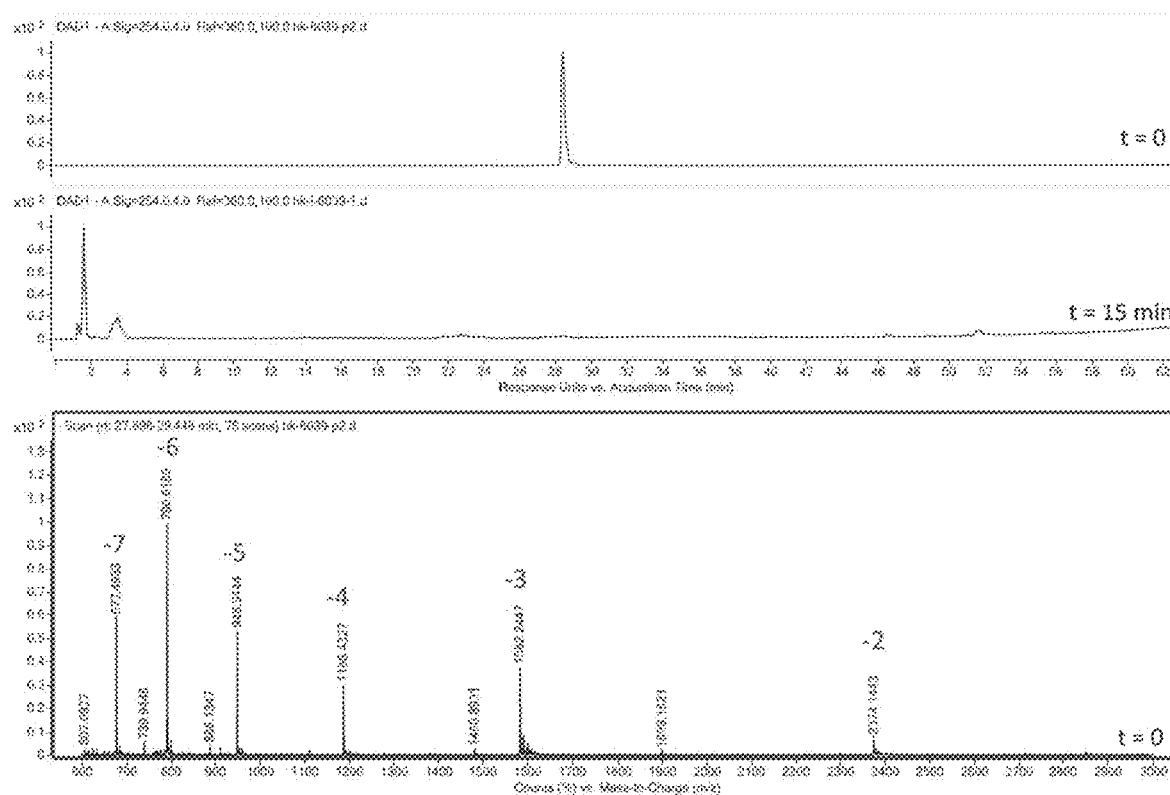

FIG. 29 shows time-dependent enzymatic hydrolysis of DNA control ODN13 (Table 1) in the presence of svPDE enzyme (100 mM Tris pH 9, 14 mM MgCl2, 72 mM NaCl, 13.3 □M ODN, 1×10-1 U/mL svPDE enzyme). ODN 12 was completely degraded within 15 minutes under these conditions.

Figure 30:
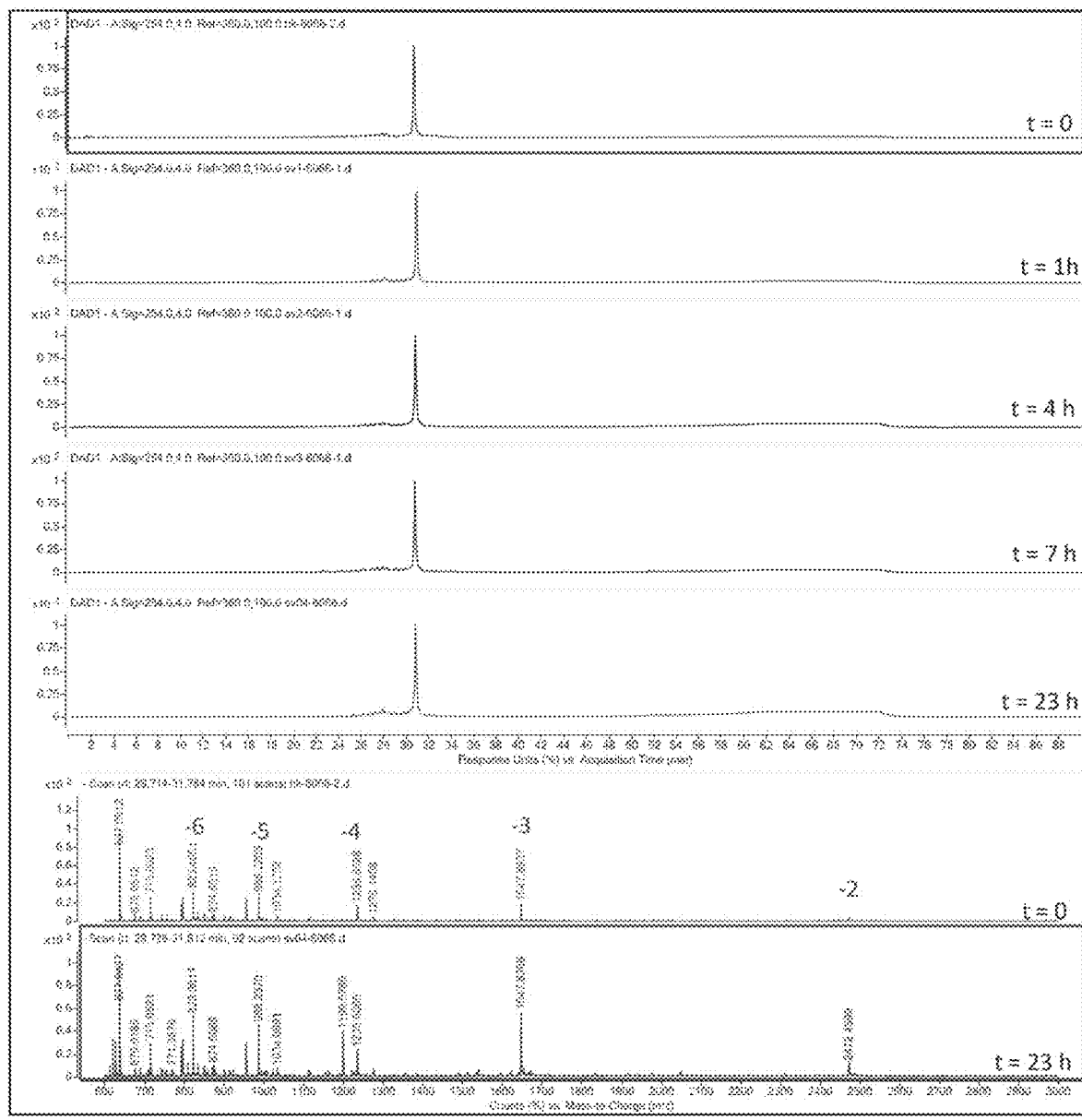

FIG. 30 shows time-dependent enzymatic hydrolysis of TMO ODN7 (Table 1) in the presence of svPDE enzyme (100 mM Tris pH 9, 14 mM MgCl2, 72 mM NaCl, 13.3 □M ODN, 2×10-1 U/mL svPDE enzyme). (a) UV profile over time as observed during LCMS of higher Rt peak at each time point is shown. (b) TIC of ODN 7 (101 scans from Rt=29.7-31.8 min of UV profile, m/z=600-3000 range) before enzymatic degradation (92 scans from Rt=29.7-31.6 min of UV profile, m/z=600-3000 range) and after svPDE treatment for t=23 h.

Figure 31:
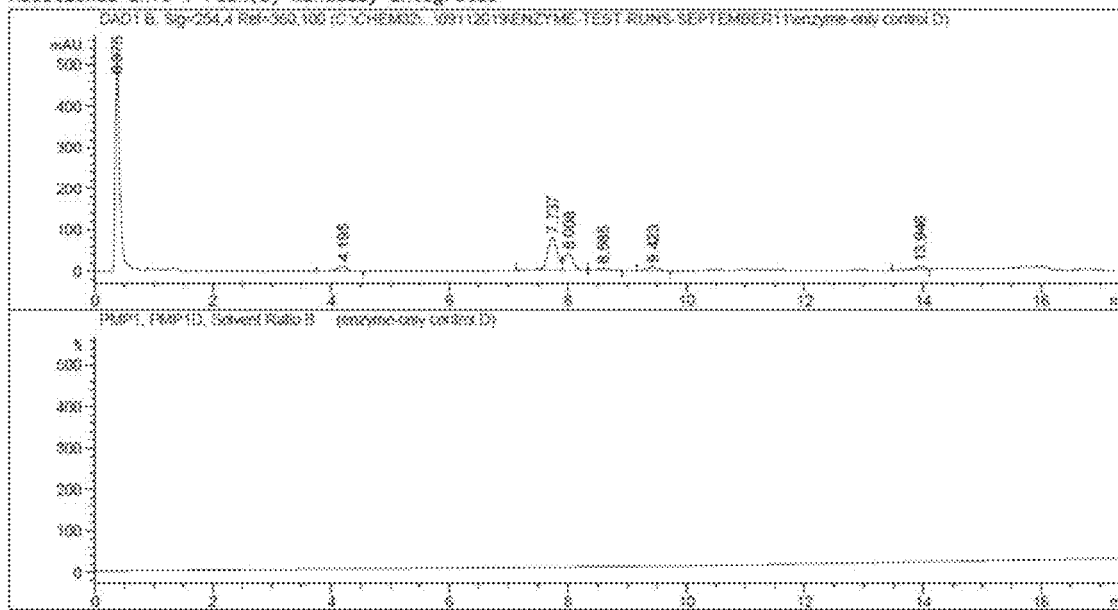

FIG. 31 Analytical RP-HPLC profile of svPDE reaction mixture prior to the addition of ODN 8.

Figure 32:
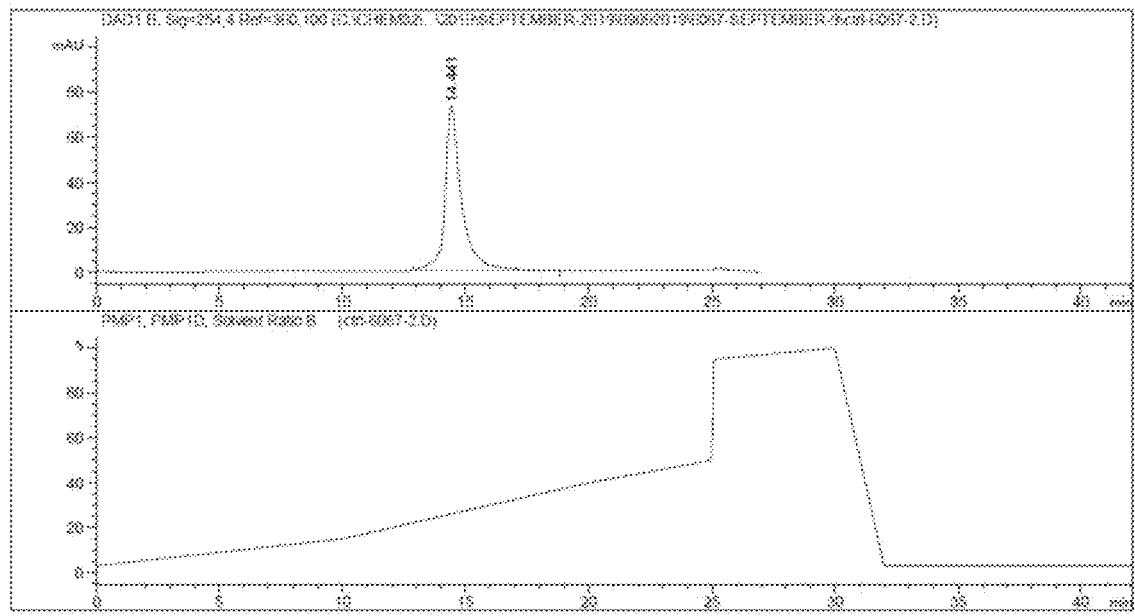

FIG. 32 Analytical RP-HPLC profile of ODN 8 (Table 1) that was used to perform svPDE assay.

FIG. 33 shows analytical RP-HPLC profile obtained during svPDE reaction of ODN 8 at t=5 minutes.

Figure 34:
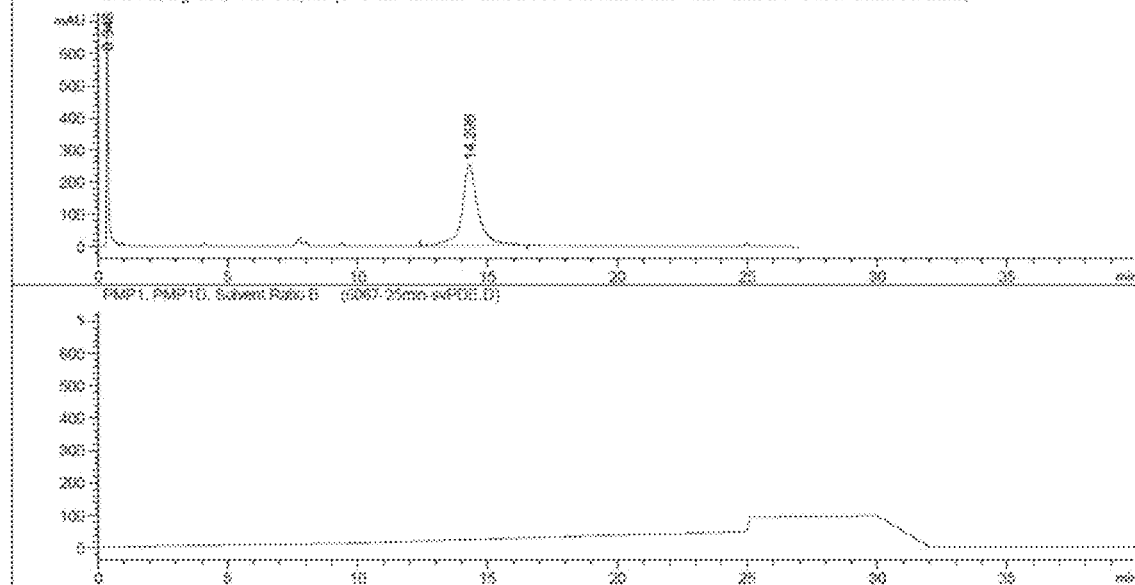

FIG. 34 shows analytical RP-HPLC profile obtained during svPDE reaction of ODN 8 at t=25 minutes.

Figure 35:
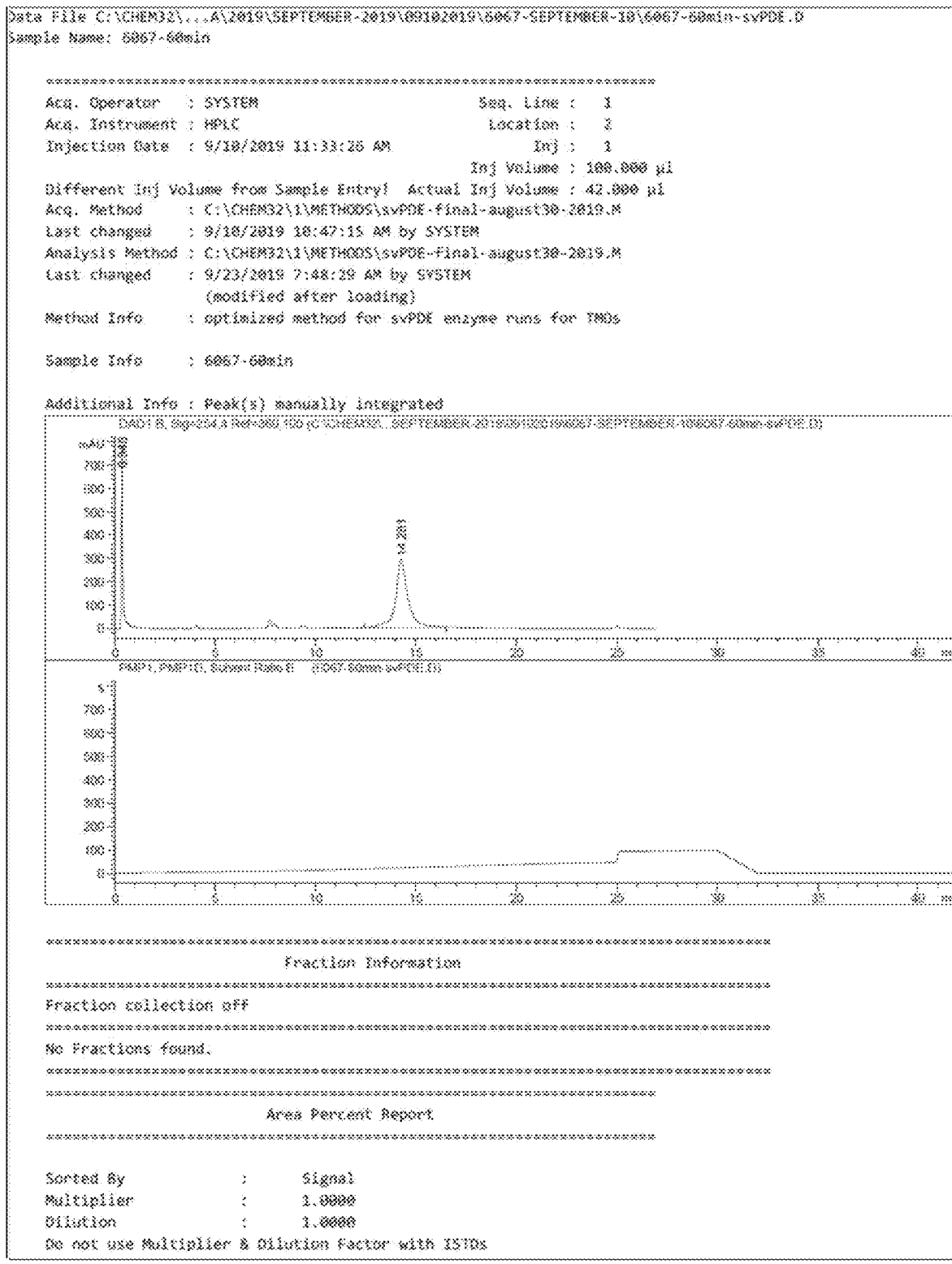

FIG. 35 shows analytical RP-HPLC profile obtained during svPDE reaction of ODN 8 at t=60 minutes.

Figure 36:
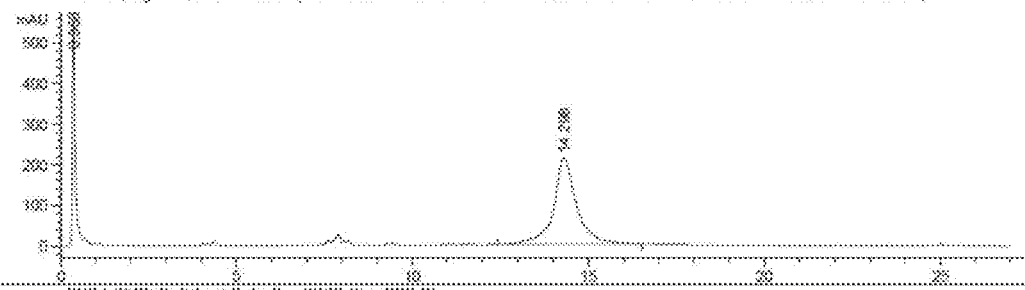

FIG. 36 shows analytical RP-HPLC profile obtained during svPDE reaction of ODN 8 at t=4 h.

Figure 37:
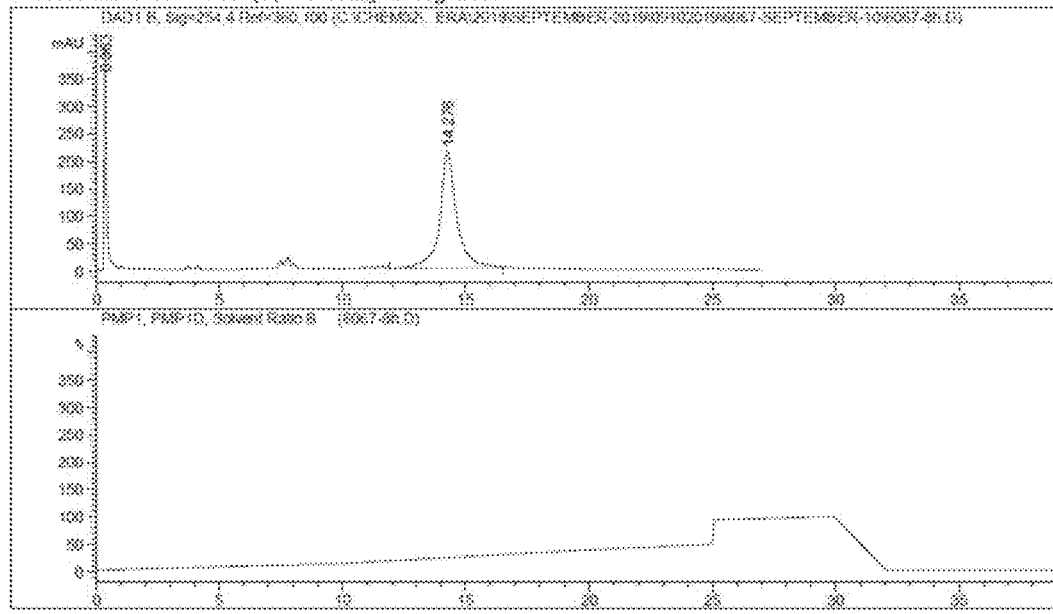

FIG. 37 shows analytical RP-HPLC profile obtained during svPDE reaction of ODN 8 at t=8 h.

Figure 38:
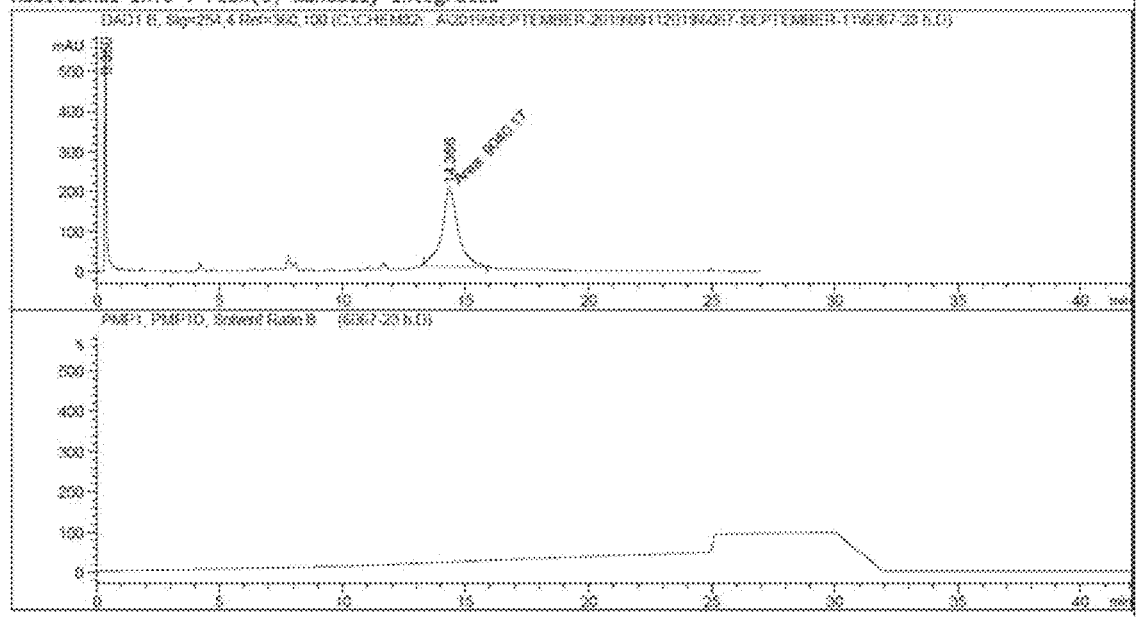

FIG. 38 shows analytical RP-HPLC profile obtained during svPDE reaction of ODN 8 at t=23 h.

Figure 39:
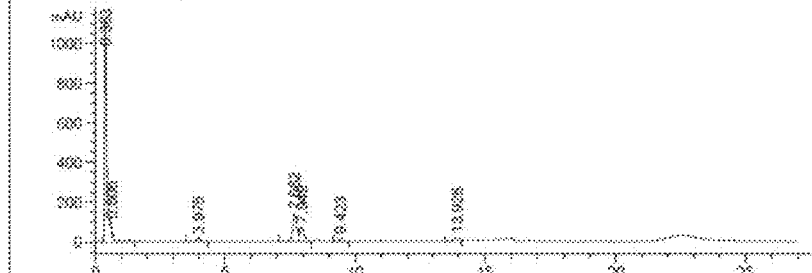

FIG. 39 shows analytical RP-HPLC profile of svPDE enzyme prior to the addition of pS DNA ODN 12 (Table 1).

Figure 40:
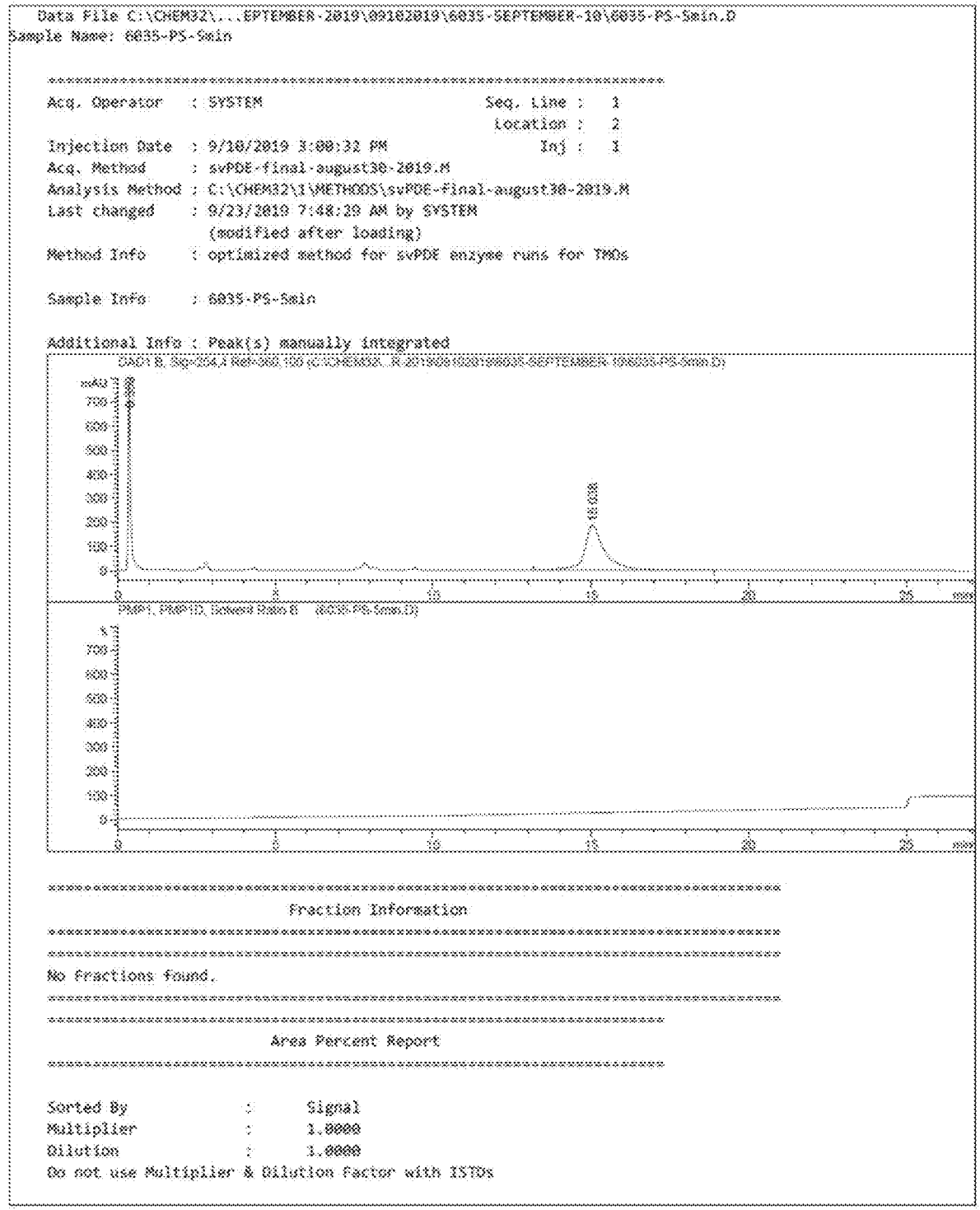

FIG. 40 shows analytical RP-HPLC profile obtained during svPDE reaction of ODN 12 at t=5 minutes.

Figure 41:
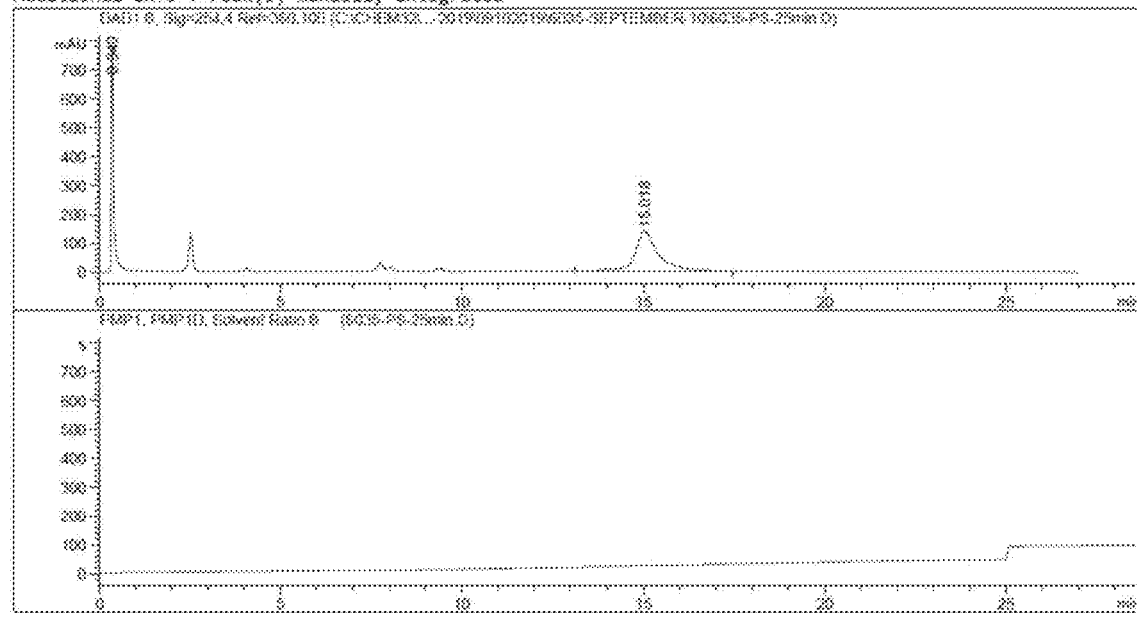

FIG. 41 shows analytical RP-HPLC profile obtained during svPDE reaction of ODN 12 at t=25 minutes.

Figure 42:
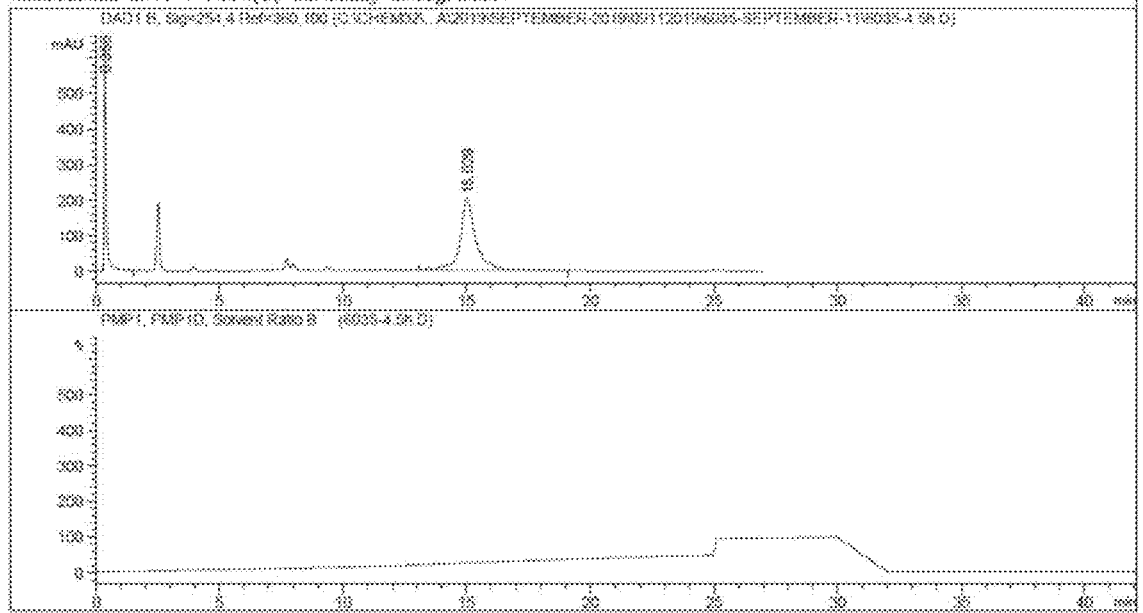

FIG. 42 shows analytical RP-HPLC profile obtained during svPDE reaction of ODN 12 at t=4.5 h.

Figure 43:
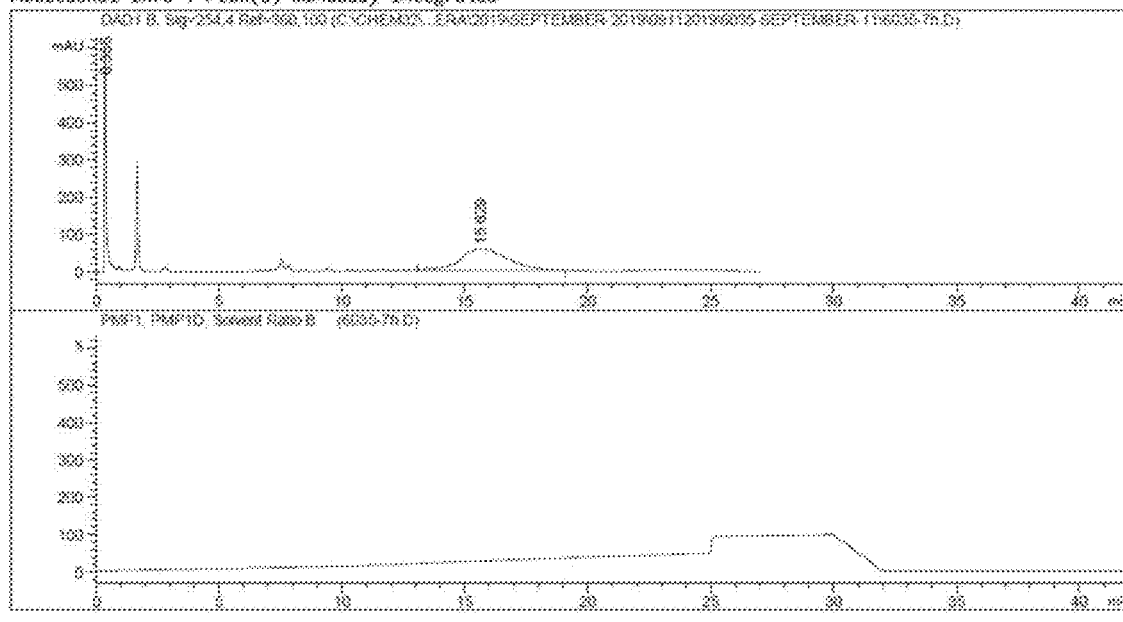
Figure 44A:
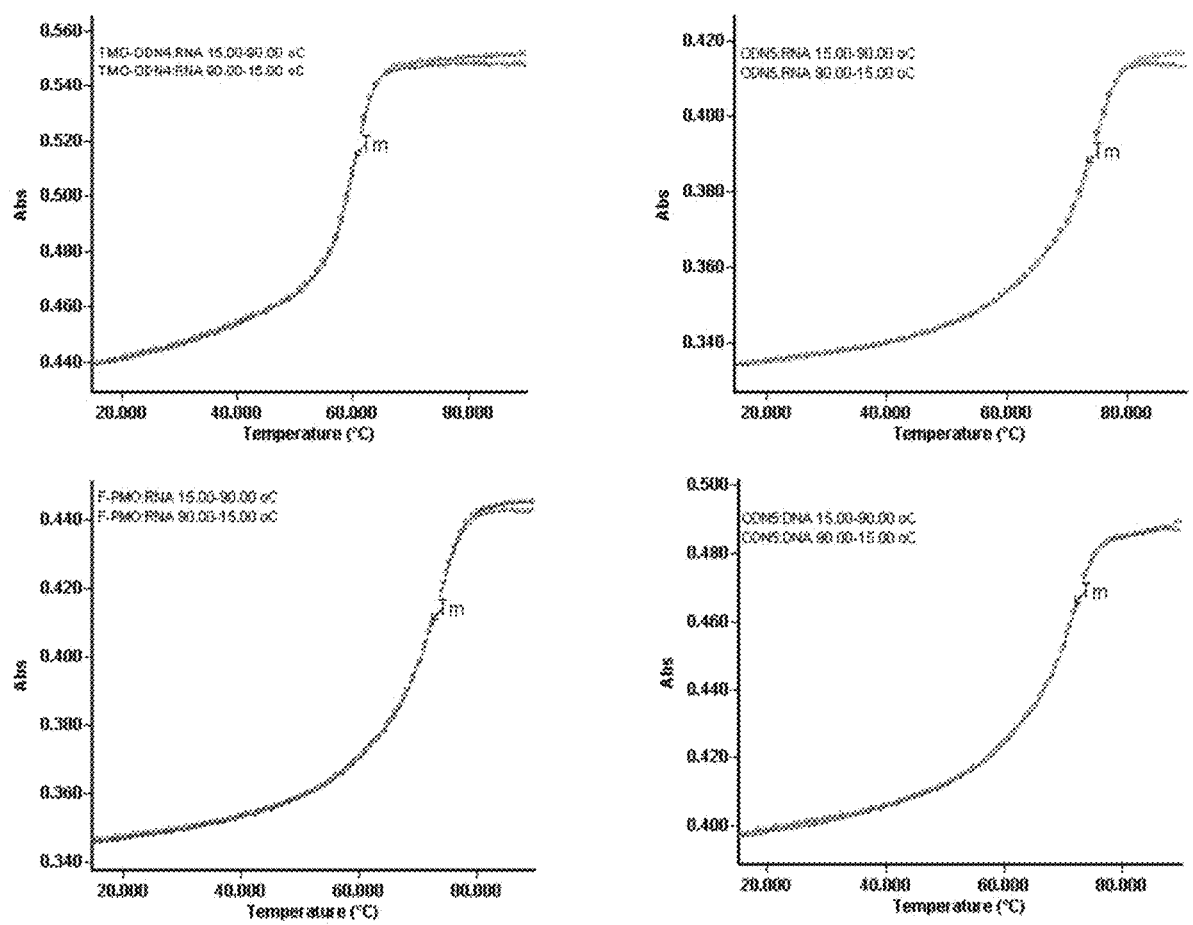
Figure 44B:
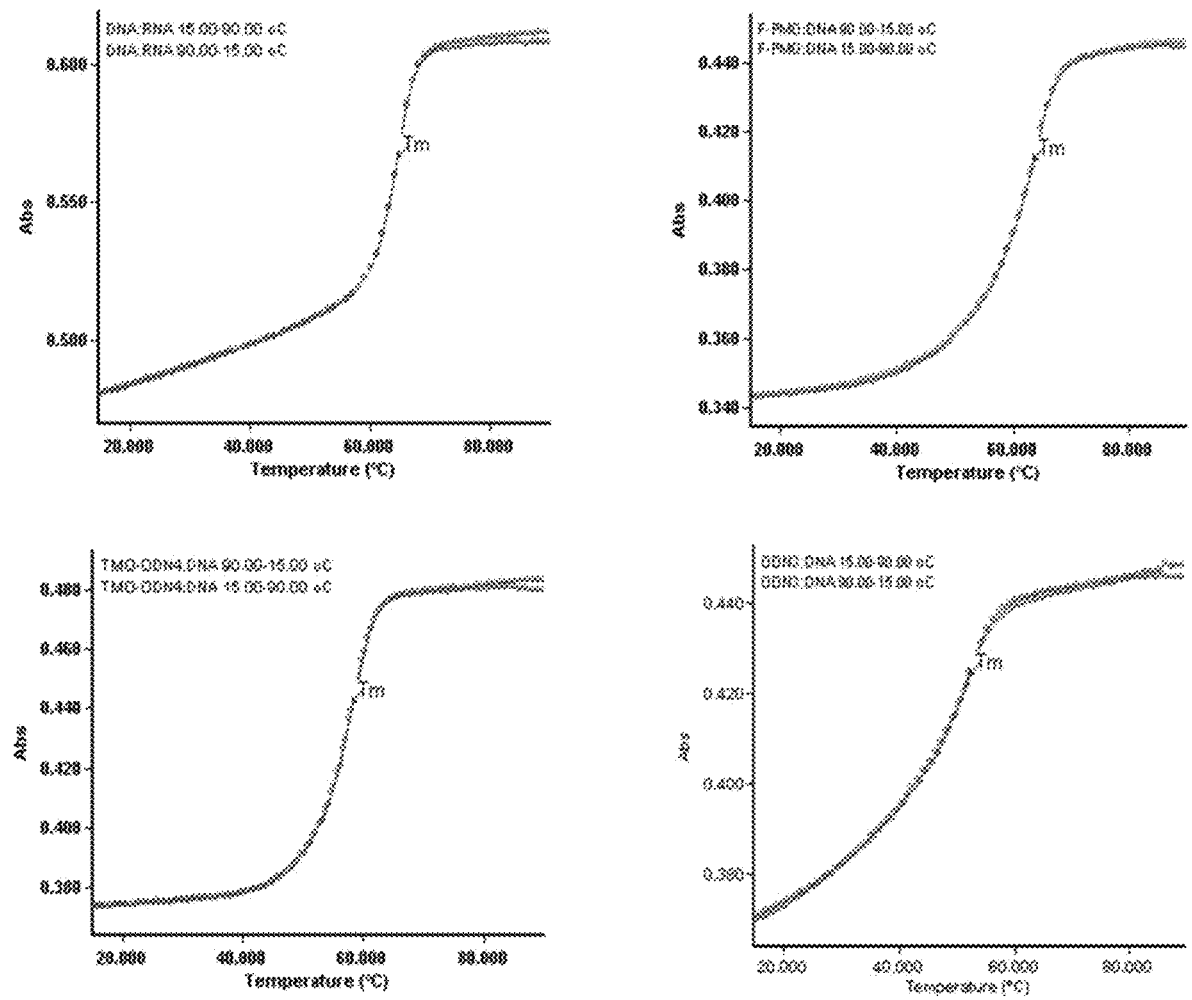
Figure 44C:
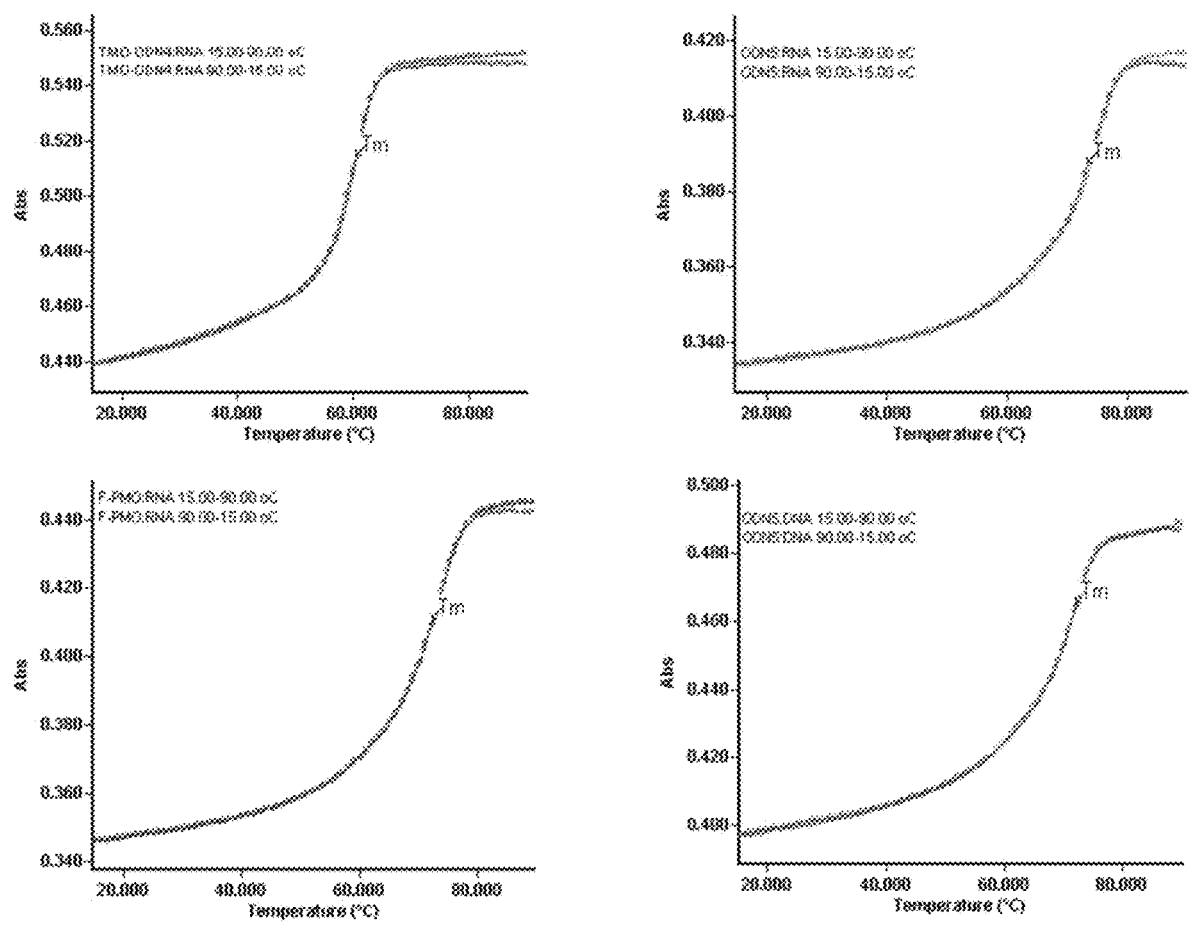
Figure 44D:
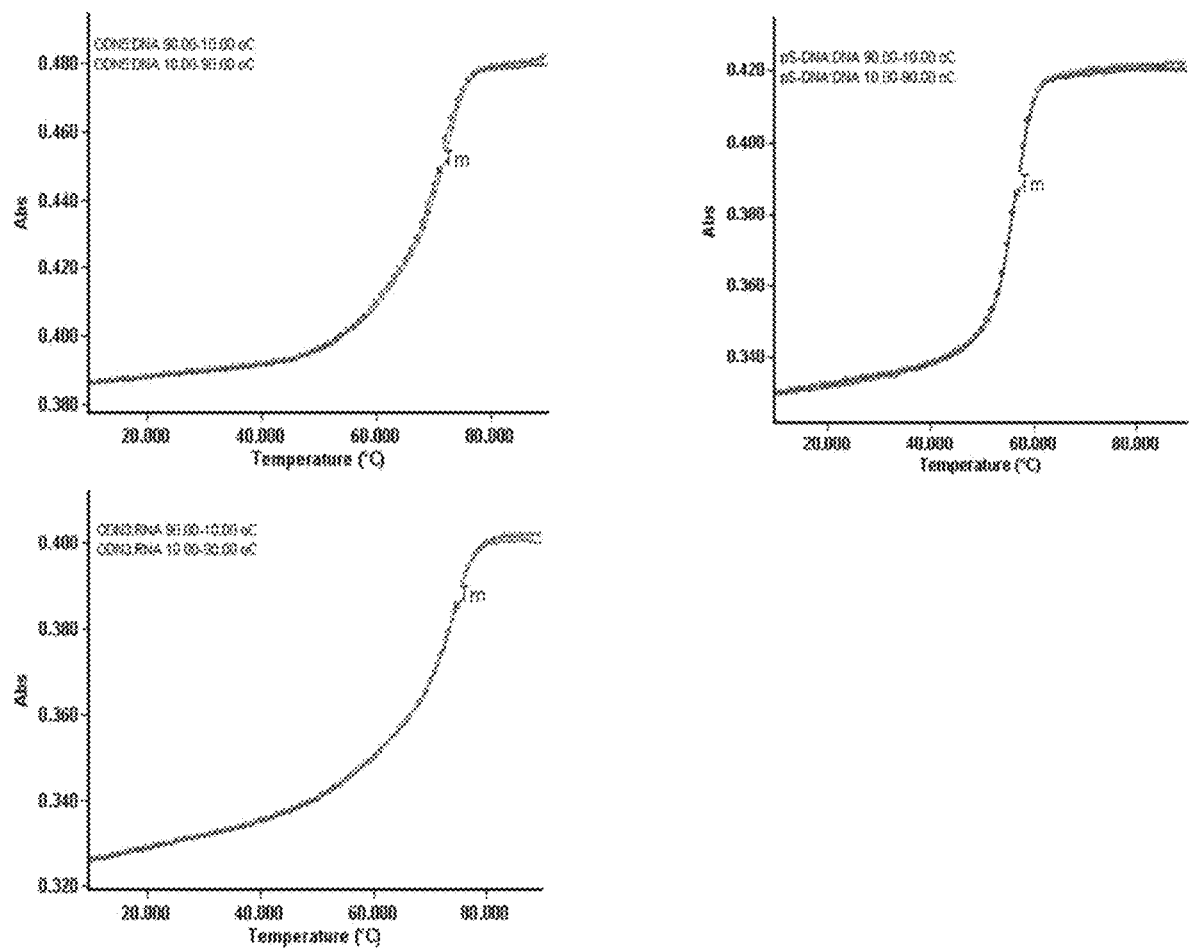
Figure 44E:
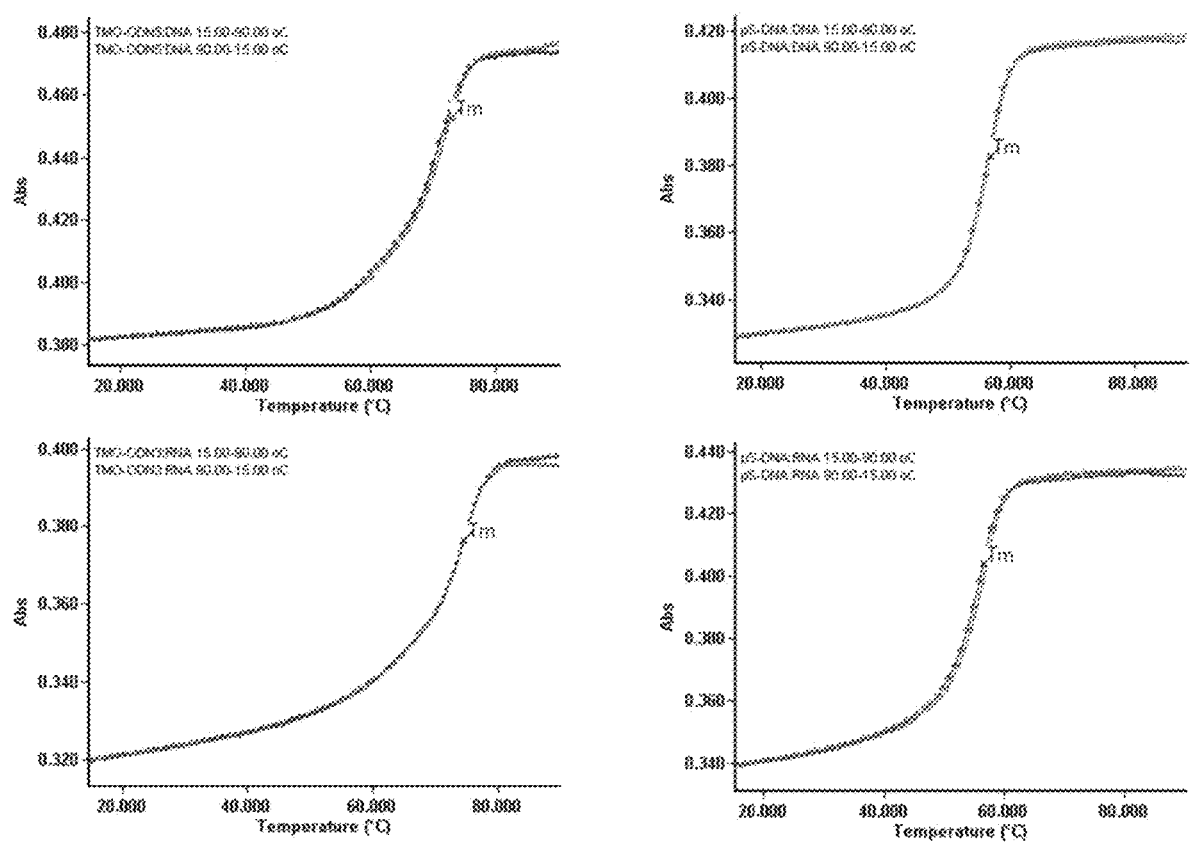
Figure 44F:
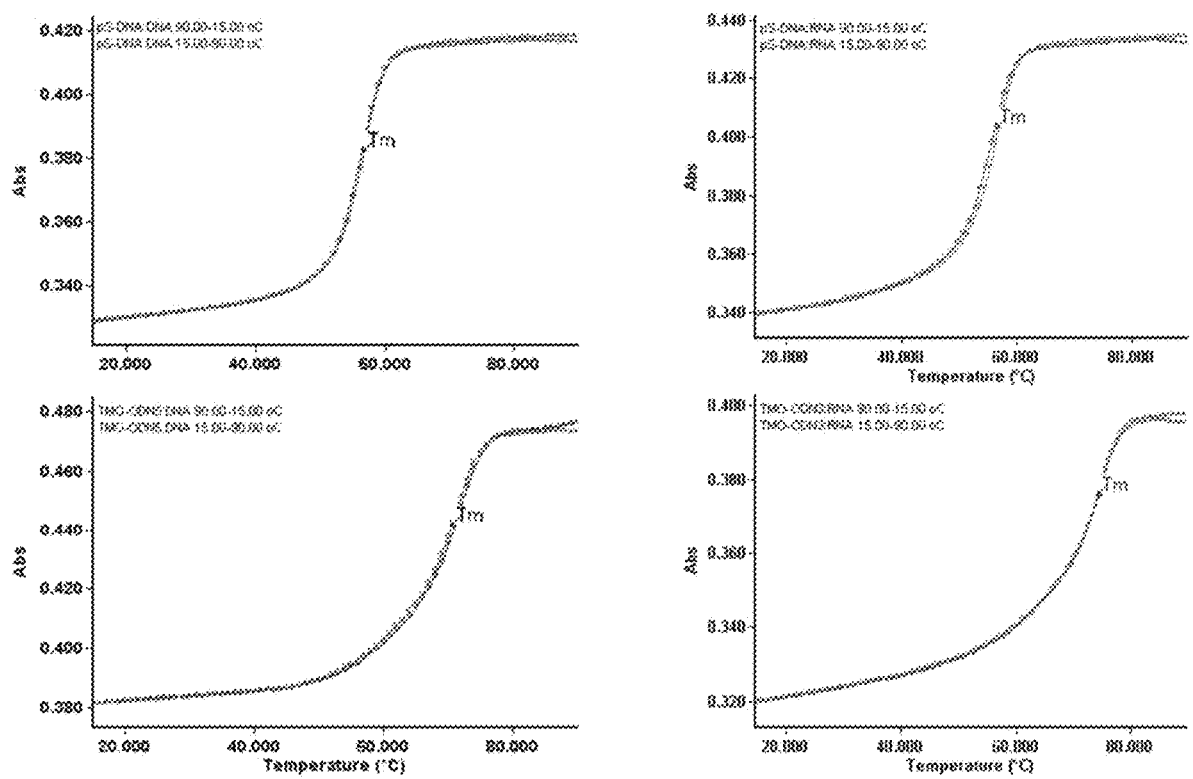

FIG. 43 shows analytical RP-HPLC profile obtained during svPDE reaction of ODN 12 at t=7 h.

FIG. 44A-F shows UV thermal denaturation data.

Figure 45:
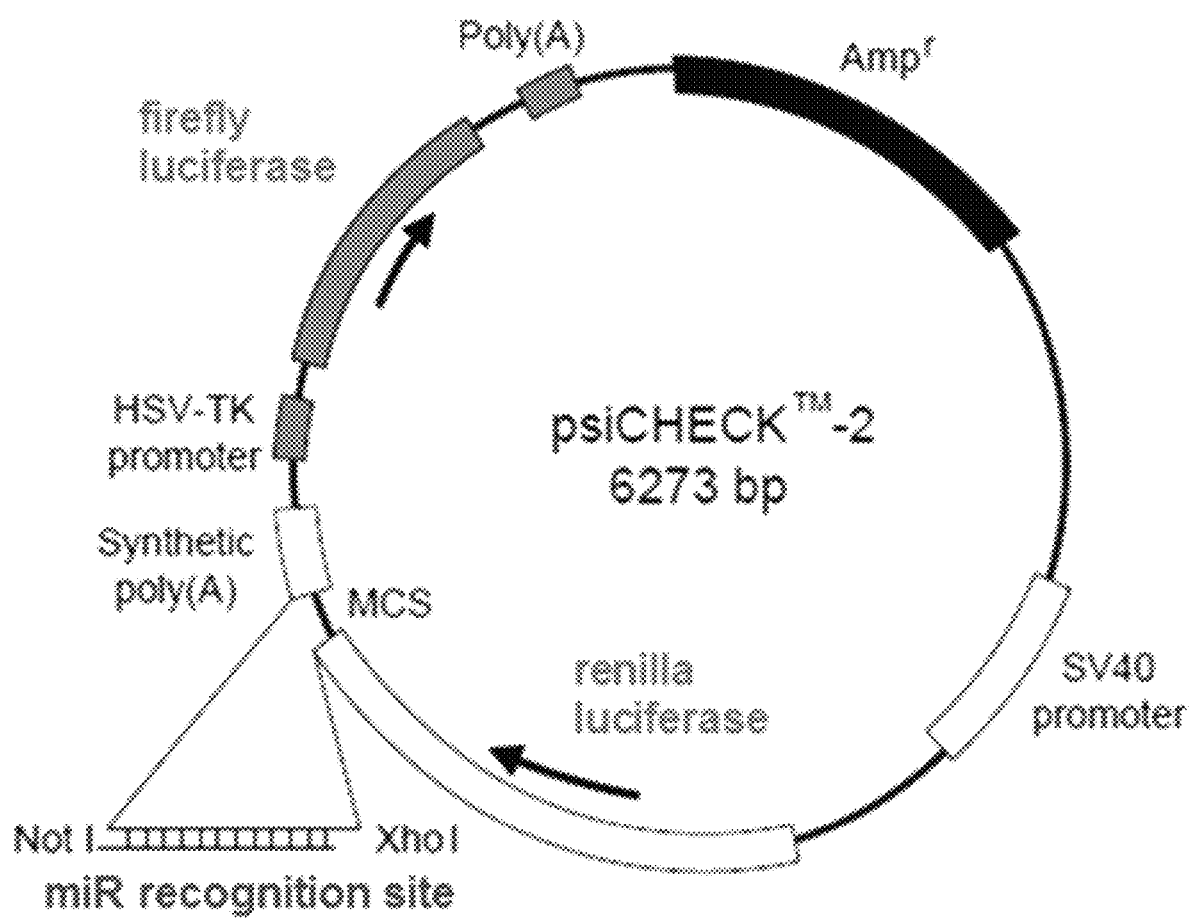

FIG. 45 show a Vector map for plasmid. The HeLa-15b cell line was a kind gift from miRagen Therapeutics Inc.

DETAILED DESCRIPTION OF THE INVENTION

Various diseases or disorders caused by the expression of truncated proteins can be treated by targeted exon skipping, such as hemophilia B, cystic fibrosis, and spinal muscular atrophy among others. For example, such diseases or disorders may be treated by targeted exon skipping during the splicing process in a human subject. For example, one or more antisense nucleotides, and preferably an antisense oligonucleotide of 8 to 50 nucleotides in length, comprising at least 1 thiomorpholino nucleotide, and further comprising at least 8 to 10 consecutive nucleotides complementary to a target region in an exon of a target gene, wherein the antisense oligonucleotide specifically hybridizes to the target region inducing exon skipping. In some embodiment, an antisense nucleotide having at least one thiomorpholino nucleotides as generally described herein may be used to generate targeted exon skipping during the splicing process in a human subject for one orm roe of the following disease conditions: 1.) Protein Tyrosine Phosphatase Gene (PTPN1); 2.) Facioscapulo Humeral Muscular Dystrophy; 3.) Hereditary Spastic Paraparesis; 4.) COL7A1; 5.) Marfan Syndrome; 6.) Nieman Pick Syndrome; 7.) Duchenne Muscular Dystrophy; 8.) Spinal MuscularAtrophy; 9.) Familial Dysautonomia; 10.) Batten Disease; 11.) SLC6A1-Epileptic Encephalopathy, among others known in the art. Indeed, the use of thiomorpholino antisense compounds for inducing exon skipping to treats such disease may be preferred over current therapeutic options for the reasons discussed below.

In one preferred embodiment, this disclosure provides improved methods for treating muscular dystrophy, such as Duchenne muscular dystrophy (DMD), by administering antisense oligonucleotide compounds that are specifically designed to induce exon skipping in the human dystrophin gene. Dystrophin plays a vital role in muscle function, and various muscle-related diseases are characterized by mutated forms of this gene. Hence, in certain embodiments, the improved methods described herein may be used to induce exon skipping in mutated forms of the human dystrophin gene, such as the mutated dystrophin genes found in DMD.

Due to aberrant mRNA splicing events caused by mutations, mutated human dystrophin genes either express defective dystrophin protein or express no measurable dystrophin at all, a condition that leads to various forms of muscular dystrophy. To remedy this condition, the antisense compounds of this disclosure hybridize to selected regions of a pre-processed RNA of a mutated human dystrophin gene, and induce exon skipping and differential splicing in that otherwise aberrantly spliced dystrophin mRNA, thereby allowing muscle cells to produce an mRNA transcript that encodes a functional dystrophin protein. In certain embodiments, the resulting dystrophin protein is not necessarily the "wild-type" form of dystrophin, but is rather a truncated, yet functional or semi-functional, form of dystrophin.

By increasing the levels of functional dystrophin protein in muscle cells, these methods are useful in the prophylaxis and treatment of muscular dystrophy, especially those forms of muscular dystrophy, such as DMD, that are characterized by the expression of defective dystrophin proteins due to aberrant mRNA splicing. The methods described herein further provide improved treatment options for patients with muscular dystrophy and offer significant and practical advantages over alternate methods of treating relevant forms of muscular dystrophy. For example, the improved methods of this disclosure relate to the administration of a thiomorpholino antisense compound for inducing exon skipping in the human dystrophin gene that may require lower doses and/or less frequent dosing regimens than prior approaches.

Thus, the invention relates to improved methods for treating muscular dystrophy, such as DMD, by inducing exon skipping in a patient. In these methods, exon skipping is induced by administering an effective amount of a composition which includes a thiomorpholino oligomer (TMO), which selectively binds to a target sequence in an exon of dystrophin pre-mRNA. In these methods of treating DMD an effective amount of an administered composition may comprise one of several amounts e.g. 2 mg/kg, about 5 mg/kg, about 10 mg/kg, or a dosage in the range of 15 mg/kg to 50 mg/kg, which includes an antisense thiomorpholino as described herein, administered over a period of time sufficient to treat the disease.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

The terms "complementary" and "complementarity" refer to polynucleotides (i.e., a sequence of nucleotides) related by base-pairing rules. For example, the sequence "T-G-A (5'-3')," is complementary to the sequence "T-C-A (5'-3')." Complementarity may be "partial," in which only some of the nucleic acids' bases are matched according to base pairing rules. Or, there may be "complete" or "total" complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5' and/or 3' terminus.

The terms "cell penetrating peptide" and "CPP" are used interchangeably and refer to cationic cell penetrating peptides, also called "transport peptides," "carrier peptides," or "peptide transduction domains." The peptides, as shown herein, have the capability of inducing cell penetration within 100% of cells of a given cell culture population and allow macromolecular translocation within multiple tissues in vivo upon systemic administration. A preferred CPP embodiment is an arginine-rich peptide as described further below.

The terms "antisense oligomer" and "antisense compound" and "antisense oligonucleotide" are used interchangeably and refer to a sequence of cyclic nucleotides, each bearing a base-pairing moiety, linked by internucleotide linkages that allow the base-pairing moieties to hybridize to a target sequence in a nucleic acid (typically an RNA) by Watson-Crick base pairing, to form a nucleic acid:oligomer heteroduplex within the target sequence. The cyclic subunits are based on ribose or another pentose sugar or, in a preferred embodiment, a thiomorpholino group (see description of morpholino oligomers below). The oligomer may have exact or near sequence complementarity to the target sequence; variations in sequence near the termini of an oligomer are generally preferable to variations in the interior.

In these methods, the antisense oligomer can be designed to block or inhibit translation of mRNA or to inhibit natural pre-mRNA splice processing and may be said to be "directed to" or "targeted against" a target sequence with which it hybridizes. The target sequence is typically a region including an AUG start codon of an mRNA, a Translation Suppressing Oligomer, or splice site of a pre-processed mRNA, a Splice Suppressing Oligomer (SSO). The target sequence for a splice site may include an mRNA sequence having its 5' end 1 to about 25 base pairs downstream of a normal splice acceptor junction in a preprocessed mRNA. A preferred target sequence is any region of a preprocessed mRNA that includes a splice site or is contained entirely within an exon coding sequence or spans a splice acceptor or donor site. An oligomer is more generally said to be "targeted against" a biologically relevant target, such as a protein, virus, or bacteria, when it is targeted against the nucleic acid of the target in the manner described above.

The terms "morpholino oligomer" or "thiomorpholino oligomer" or "TMO" refer to an oligonucleotide analog composed of morpholino subunit structures (including thiomorpholinos), where (i) the structures are linked together by phosphorothioate-containing linkages, one to three atoms long, preferably two atoms long, that may be uncharged or cationic, joining the morpholino nitrogen of one subunit to a 5' exocyclic carbon of an adjacent subunit, and (ii) each morpholino ring bears a purine or pyrimidine base-pairing moiety effective to bind, by base-specific hydrogen bonding, to a base in a polynucleotide. See, for example, the structures depicted in FIGS. 1A, 1B, and 1C. Variations can be made to this linkage as long as they do not interfere with binding or activity. The 5' oxygen may be substituted with amino or lower alkyl substituted amino. The pendant nitrogen attached to phosphorus may be unsubstituted, monosubstituted, or disubstituted with (optionally substituted) lower alkyl. The purine or pyrimidine base pairing moiety is typically adenine, cytosine, guanine, uracil, thymine or inosine. The synthesis, structures, and binding characteristics of morpholino oligomers are detailed in co-pending PCT patent Application No. PCT/US17/51839, filed Sep. 15, 2017, which is incorporated herein by reference in its entirety.

An "amino acid subunit" or "amino acid residue" can refer to an alpha-amino acid residue (—CO—CHR—NH—) or a beta- or other amino acid residue (e.g. —CO—$(CH_2)_n$CHR—NH—), wherein R is a side chain (which may include hydrogen) and n is 1 to 6, preferably 1 to 4.

The term "naturally occurring amino acid" refers to an amino acid present in proteins found in nature. The term "non-natural amino acids" refers to those amino acids not present in proteins found in nature; examples include beta-alanine (beta-Ala), 6-aminohexanoic acid (Ahx) and 6-aminopentanoic acid.

An "exon" refers to a defined section of nucleic acid that encodes a protein, or a nucleic acid sequence that is represented in the mature form of an RNA molecule after either portions of a pre-processed (or precursor) RNA have been removed by splicing. The mature RNA molecule can be a messenger RNA (mRNA) or a functional form of a non-coding RNA, such as rRNA or tRNA. The human dystrophin gene has 79 exons.

An "intron" refers to a nucleic acid region (within a gene) that is not translated into a protein. An intron is a non-coding section that is transcribed into a precursor mRNA (pre-mRNA), and subsequently removed by splicing during formation of the mature RNA.

An "effective amount" or "therapeutically effective amount" refers to an amount of therapeutic compound, such as an antisense oligonucleotide, administered to a human subject, either as a single dose or as part of a series of doses, which is effective to produce a desired therapeutic effect. For an antisense oligonucleotide, this effect is typically brought about by inhibiting translation or natural splice-processing of a selected target sequence. An effective amount may be variable such as 5 mg/kg of a composition comprising a thiomorpholino antisense oligonucleotide for a period of time to treat the subject. In one embodiment, an effective amount might be 5 mg/kg of a composition comprising an antisense oligonucleotide to increase the number of dystrophin-positive fibers in a subject to at least 20% of normal. In another embodiment, an effective amount may be 5 mg/kg of a composition including an antisense oligonucleotide to stabilize, maintain, or improve walking distance in a patient, relative to a healthy peer. In another aspect, an effective amount may be 5 mg/kg, administered for at least 24 weeks, at least 36 weeks, or at least 48 weeks, to thereby increase the number of dystrophin-positive fibers in a subject to at least 20%, to about 30%, about 40%, about 50%, about 60%, about 70%, about 80%, about 90%, or to about 95% of normal, and stabilize or improve walking distance in the patient relative to a healthy peer.

"Exon skipping" refers generally to the process by which an entire exon, or a portion thereof, is removed from a given pre-processed RNA, and is thereby excluded from being present in the mature RNA, such as the mature mRNA that is translated into a protein. Hence, the portion of the protein that is otherwise encoded by the skipped exon is not present in the expressed form of the protein, typically creating an altered, though still functional, form of the protein. In certain embodiments, the exon being skipped is an aberrant exon from the human dystrophin gene, which may contain a mutation or other alteration in its sequence that otherwise causes aberrant splicing. In certain embodiments, the exon being skipped is any one or more of exons 1-79 of the human dystrophin gene, such as 3-8, 10-16, 19-40, 42-47, and 50-55, though exons 24, 44, 45, 46, 47, 48, 49, 50, 51, 52, 53, 54, 55, 56 and 8 of the human dystrophin gene are preferred.

"Dystrophin" is a rod-shaped cytoplasmic protein, and a vital part of the protein complex that connects the cytoskeleton of a muscle fiber to the surrounding extracellular matrix through the cell membrane. Dystrophin contains multiple functional domains. For instance, dystrophin contains an actin binding domain at about amino acids 14-240 and a central rod domain at about amino acids 253-3040. This large central domain is formed by 24 spectrin-like triple-helical elements of about 109 amino acids, which have homology to alpha-actinin and spectrin. The repeats are typically interrupted by four proline-rich non-repeat segments, also referred to as hinge regions. Repeats 15 and 16 are separated by an 18 amino acid stretch that appears to provide a major site for proteolytic cleavage of dystrophin. The sequence identity between most repeats ranges from 10-25%. One repeat contains three alpha-helices: 1, 2, and 3. Alpha-helices 1 and 3 are each formed by 7 helix turns, interacting as a coiled-coil through a hydrophobic interface. Alpha-helix 2 has a more complex structure and is formed by segments of four and three helix turns, separated by a Glycine or Proline residue. Each repeat is encoded by two exons, typically interrupted by an intron between amino acids 47 and 48 in the first part of alpha-helix 2. The other intron is found at different positions in the repeat, usually scattered over helix-3. Dystrophin also contains a cysteine-rich domain at about amino acids 3080-3360), including a cysteine-rich segment (i.e., 15 cysteines in 280 amino acids) showing homology to the C-terminal domain of the slime mold (Dictyostelium discoideum) alpha-actinin. The carboxy-terminal domain is at about amino acids 3361-3685.

The amino-terminus of dystrophin binds to F-actin and the carboxy-terminus binds to the dystrophin-associated protein complex (DAPC) at the sarcolemma. The DAPC includes the dystroglycans, sarcoglycans, integrins and caveolin, and mutations in any of these components cause autosomally-inherited muscular dystrophies. The DAPC is destabilized when dystrophin is absent, which results in diminished levels of the member proteins, and in turn leads to progressive fiber damage and membrane leakage. In various forms of muscular dystrophy, such as Duchenne's muscular dystrophy (DMD) and Becker's muscular dystrophy (BMD), muscle cells produce an altered and functionally defective form of dystrophin, or no dystrophin at all, mainly due to mutations in the gene sequence that lead to incorrect splicing. The predominant expression of the defective dystrophin protein, or the complete lack of dystrophin or a dystrophin-like protein, leads to rapid progression of muscle degeneration, as noted above. In this regard, a "defective" dystrophin protein may be characterized by the forms of dystrophin that are produced in certain subjects with DMD or BMD, as known in the art, or by the absence of detectable dystrophin.

As used herein, the terms "function" and "functional" and the like refer to a biological, enzymatic, or therapeutic function. A "functional" dystrophin protein refers generally to a dystrophin protein having sufficient biological activity to reduce the progressive degradation of muscle tissue that is otherwise characteristic of muscular dystrophy, typically as compared to the altered or "defective" form of dystrophin protein that is present in certain subjects with DMD or BMD. In certain embodiments, a functional dystrophin protein may have about 10%, 20%, 30%, 40%, 50%, 60%, 70%, 80%, 90%, or 100% (including all integers in between) of the in vitro or in vivo biological activity of wild-type dystrophin, as measured according to routine techniques in the art. As one example, dystrophin-related activity in muscle cultures in vitro can be measured according to myotube size, myofibril organization (or disorganization), contractile activity, and spontaneous clustering of acetylcholine receptors (see, e.g., Brown et al., Journal of Cell Science. 112:209-16, 1999). Animal models are also valuable resources for studying the pathogenesis of disease and provide a means to test dystrophin-related activity. Two of the most widely used animal models for DMD research are the mdx mouse and the golden retriever muscular dystrophy (GRMD) dog, both of which are dystrophin negative (see, e.g., Collins & Morgan, Int J Exp Pathol 84: 165-172, 2003). These and other animal models can be used to measure the functional activity of various dystrophin proteins. Included are truncated forms of dystrophin, such as those forms that are produced by certain of the exon-skipping antisense compounds of the present invention.

The term "restoration" of dystrophin synthesis or production refers generally to the production of a dystrophin protein including truncated forms of dystrophin in a patient with muscular dystrophy following treatment with an antisense oligonucleotide as described herein. In some embodiments, treatment results in an increase in novel dystrophin production in a patient by 1%, 5%, 10%, 20%, 30%, 40%, 50%, 60%, 70%, 80%, 90% or 100% (including all integers in between). In some embodiments, treatment increases the number of dystrophin-positive fibers to at least 20%, about 30%, about 40%, about 50%, about 60%, about 70%, about 80%, about 90% or about 95% to 100% of normal in the subject. In other embodiments, treatment increases the number of dystrophin-positive fibers to about 20% to about 60%, or about 30% to about 50% of normal in the subject. The percent of dystrophin-positive fibers in a patient following treatment can be determined by a muscle biopsy using known techniques. For example, a muscle biopsy may be taken from a suitable muscle, such as the biceps brachii muscle in a patient.

Analysis of the percentage of positive dystrophin fibers may be performed pre-treatment and/or post-treatment or at time points throughout the course of treatment. For example, a post-treatment biopsy is taken from the contralateral muscle from the pre-treatment biopsy. Pre- and post-treatment dystrophin expression studies may be performed using any suitable assay for dystrophin. Immunohistochemical detection is performed on tissue sections from the muscle biopsy using an antibody that is a marker for dystrophin, such as a monoclonal or a polyclonal antibody. For example, the MANDYS106 antibody can be used which is a highly sensitive marker for dystrophin. Any suitable secondary antibody may be used.

The percent dystrophin-positive fibers may be calculated by dividing the number of positive fibers by the total fibers counted. Normal muscle samples have 100% dystrophin-positive fibers. Therefore, the percent dystrophin-positive fibers can be expressed as a percentage of normal. To control for the presence of trace levels of dystrophin in the pretreatment muscle as well as revertant fibers a baseline can be set using sections of pre-treatment muscles from each patient when counting dystrophin-positive fibers in post-treatment muscles. This may be used as a threshold for counting dystrophin-positive fibers in sections of post-treatment muscle in that patient. Antibody-stained tissue sections can also be used for dystrophin quantification using Bioquant image analysis software (Bioquant Image Analysis Corporation, Nashville, Tenn.). The total dystrophin fluorescence signal intensity can be reported as a percentage of normal. In addition, Western blot analysis with monoclonal or polyclonal anti-dystrophin antibodies can be used to determine the percentage of dystrophin positive fibers. For example, the anti-dystrophin antibody NCL-Dysl from Novacastra may be used. The percentage of dystrophin-positive fibers can also be analyzed by determining the expression of the components of the sarcoglycan complex (beta, gamma) and/or neuronal NOS.

By "isolated" is meant material that is substantially or essentially free from components that normally accompany it in its native state. For example, an "isolated polynucleotide," as used herein, may refer to a polynucleotide that has been purified or removed from the sequences that flank it in a naturally-occurring state, e.g., a DNA fragment that has been removed from the sequences that are normally adjacent to the fragment.

As used herein, "sufficient length" refers to an antisense oligonucleotide that is complementary to at least 8, more typically 8-30, contiguous nucleobases in a target dystrophin pre-mRNA. In some embodiments, an antisense oligonucleotide of sufficient length includes at least 8, 9, 10, 11, 12, 13, 14, or 15 contiguous nucleobases in the target dystrophin pre-mRNA. In other embodiments, an antisense of sufficient length includes at least 16, 17, 18, 19, 20, 21, 22, 23, 24, or 25 contiguous nucleobases in the target dystrophin pre-mRNA. An antisense oligonucleotide of sufficient length has at least a minimal number of nucleotides to be capable of specifically hybridizing to any one or more of exons 1-79 of the dystrophin gene. Preferably, the antisense oligonucleotide of the invention has a minimal number of nucleotides to be capable of specifically hybridizing to any one or more of exons 24, 44, 45, 46, 47, 48, 49, 50, 51, 52, 53, 54, 55, 56 or 8 of the human dystrophin gene. Preferably an oligonucleotide of sufficient length is from about 8 to about 50 nucleotides in length, including oligonucleotides of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40 or more nucleotides. Thus, an oligonucleotide of sufficient length may be from 10 to about 30 nucleotides in length, or from 15 to about 25 nucleotides in length, or from 20 to 30, or 20 to 50, nucleotides in length, or from 25 to 28 nucleotides in length.

By "enhance" or "enhancing," or "increase" or "increasing," or "stimulate" or "stimulating," refers generally to the ability of one or more antisense compounds or compositions of this disclosure to produce or cause a greater physiological response (i.e., downstream effects) in a cell or a subject, as compared to the response caused by either no antisense compound or a control compound. A measurable physiological response may include increased expression of a functional form of a dystrophin protein, or increased dystrophin-related biological activity in muscle tissue, among other responses apparent from the understanding in the art and the description herein. Increased muscle function can also be measured, including increases or improvements in muscle function by about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100%. The percentage of muscle fibers that express a functional dystrophin can also be measured, including increased dystrophin expression in about 1%, 2%, %, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of muscle fibers. For instance, it has been shown that around 40% of muscle function improvement can occur if 25-30% of fibers express dystrophin (see, e.g., DelloRusso et al, Proc Natl Acad Sci USA 99: 12979-12984, 2002). An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1), e.g., 1.5, 1.6, 1.7, 1.8, etc.) the amount produced by no antisense compound (the absence of an agent) or a control compound.

The term "reduce" or "inhibit" may relate generally to the ability of one or more antisense compounds of the invention to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of muscular dystrophy, or reductions in the expression of defective forms of dystrophin, such as the altered forms of dystrophin that are expressed in individuals with muscular dystrophy, such as DMD or BMD. A "decrease" in a response may be statistically significant as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

Also included are vector delivery systems that are capable of expressing the oligomeric, dystrophin-targeting sequences of the present invention, such as vectors that express a polynucleotide sequence comprising any one or more of the sequences shown in Tables 3 and 4, and variants thereof, as described herein. By "vector" or "nucleic acid construct" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof or be integrated with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition associated with the dystrophin protein, as in certain forms of muscular dystrophy, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

In one embodiment, treatment with an antisense oligonucleotide of the invention increases novel dystrophin production and slows or reduces the loss of ambulation that would be expected without treatment. For example, treatment may stabilize, maintain, improve or increase walking ability (e.g., stabilization of ambulation) in the subject. In some embodiments, treatment maintains or increases a stable walking distance in a patient, as measured by, for example, the 6 Minute Walk Test (6MWT), described by McDonald, et al. (Muscle Nerve, 2010; 42:966-74, herein incorporated by reference). A change in the 6 Minute Walk Distance (6MWD) may be expressed as an absolute value, a percentage change or a change in the %-predicted value. In some embodiments, treatment maintains or improves a stable walking distance in a 6MWT from a 20% deficit in the subject relative to a healthy peer. The performance of a DMD patient in the 6MWT relative to the typical performance of a healthy peer can be determined by calculating a %-predicted value. For example, the %-predicted 6MWD may be calculated using the following equation for males:

$$196.72+(39.81\times age)-(1.36\times age^2)+(132.28\times height\ in\ meters).$$

For females, the %-predicted 6MWD may be calculated using the following equation:

$$188.61+(51.50\times age)-(1.86\times age^2)+(86.10\times height\ in\ meters)$$

(Henricson et al. PLoS Curr., 2012, version 2). In some embodiments, treatment with an antisense oligonucleotide increases the stable walking distance in the patient from baseline to greater than 3, 5, 6, 7, 8, 9, 10, 15, 20, 25, 30 or 50 meters (including all integers in between).

Loss of muscle function in patients with DMD may occur against the background of normal childhood growth and development. Indeed, younger children with DMD may show an increase in distance walked during 6MWT over the course of about 1 year despite progressive muscular impairment. In some embodiments, the 6MWD from patients with DMD is compared to typically developing control subjects and to existing normative data from age and sex matched subjects. In other embodiments, normal growth and development can be accounted for using an age and height based equation fitted to normative data. Such an equation can be used to convert 6MWD to a percent-predicted (%-predicted) value in subjects with DMD. Analysis of %-predicted 6MWD data represents a method to account for normal growth and development, and may show that gains in function at early ages (e.g., less than or equal to age 7) represent stable rather than improving abilities in patients with DMD (Henricson et al. PLoS Curr., 2012, version 2, herein incorporated by reference).

As used herein, a "subject" includes any animal that exhibits a symptom, or is at risk for exhibiting a symptom, which can be treated with an antisense compound of the invention, such as a subject that has or is at risk for having muscular dystrophy, such as DMD or BMD, or any of the symptoms associated with these conditions (e.g., muscle fibre loss). Suitable subjects (patients) include laboratory animals (such as mouse, rat, rabbit, or guinea pig), farm animals, and domestic animals or pets (such as a cat or dog). Non-human primates and, preferably, human patients, are included.

An antisense molecule nomenclature system has been proposed and published to distinguish between the different antisense molecules (see Mann et al., (2002) J Gen Med 4, 644-654). This nomenclature may be especially relevant when testing several slightly different antisense molecules, all directed at the same target region.

Using the nomenclature: H #A/D(x:y), the first letter designates the species (e.g. H: human, M: murine, C: canine). "#" designates target dystrophin exon number. "ND" indicates acceptor or donor splice site at the beginning and end of the exon, respectively. (x y) represents the annealing coordinates where "−" or "+" indicate intronic or exonic sequences respectively. For example, A(−6+18) would indicate the last 6 bases of the intron preceding the target exon and the first 18 bases of the target exon. The closest splice site would be the acceptor so these coordinates would be preceded with an "A". Describing annealing coordinates at the donor splice site could be D(+2-18) where the last 2 exonic bases and the first 18 intronic bases correspond to the annealing site of the antisense molecule. Entirely exonic annealing coordinates that would be represented by A(+65+85), that is the site between the 65th and 85th nucleotide from the start of that exon.

II. Constructing the Antisense Oligonucleotide

Exemplary embodiments of the invention relate to morpholino oligonucleotides having thiomorpholino-containing internucleotide linkages, as illustrated in FIG. 1D. Efficient methods of making such thiomorpholino oligonucleotides, including antisense oligonucleotides, are detailed, for example, in co-owned PCT patent Application No. PCT/US17/51839, filed Sep. 15, 2017, which is expressly incorporated by reference herein.

Important properties of the thiomorpholino-based subunits include: 1) the ability to be linked in a oligomeric form with 2′-deoxyribonucleosides; 2) the ability to support a nucleotide base (e.g. adenine, cytosine, guanine, thymidine, uracil and inosine) such that the polymer formed can hybridize with a complementary-base target nucleic acid, including target RNA, Tm values above about 50° C. in relatively short oligonucleotides (e.g., 8-15 bases); 3) the ability of the oligonucleotide to be actively or passively transported into mammalian cells; and 4) longer half-life (i.e., slower excretion) than PMOs; 6) a charged backbone that increases their ability to complex with currently available transfection agents for rapid in vitro cellular uptake.

Figure 1A:
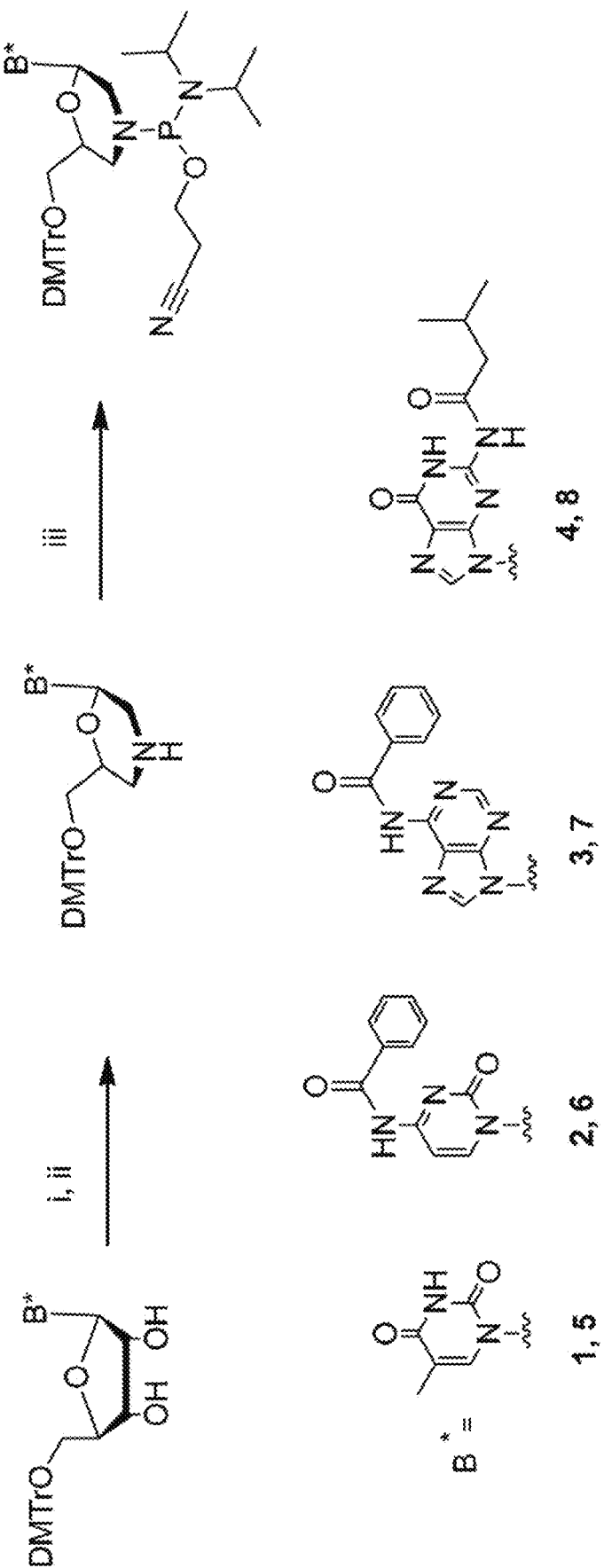
FIG. 1A shows the synthesis scheme used to prepare synthons for the synthesis cycle shown in FIG. 1B. In the synthesis scheme: reagents (i) $NaIO_4$ (1.1 equiv), $(NH_4)_2B_4O_7$ (1.1 equiv), MeOH; (ii) $NaCNBH_3$ (2.0 equiv), AcOH (2.0 equiv), MeOH; (iii) $P(OCH_2CH_2CN)(NiPr_2)_2$ (1.2 equiv), 4,5-dicyanoimidazole (0.5 equiv), and $CH_2Cl_2$. Compound 1, 2, 3, 4 are appropriately protected ribonucleosides; synthons 5, 6, 7, 8 are appropriately protected morpholino phosphoramidites.
Figure 1B:
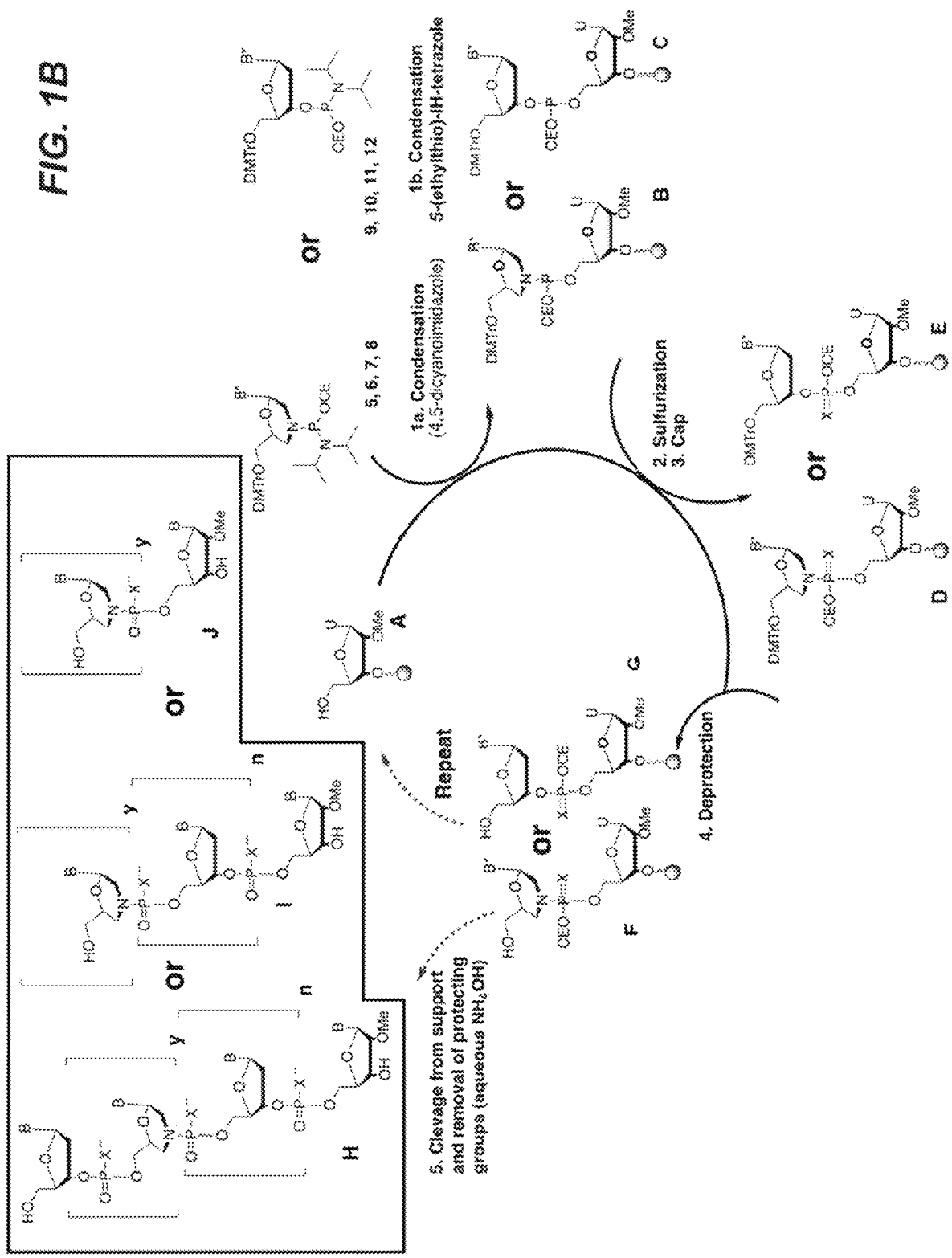
FIG. 1B shows the synthesis cycle used to prepare thiomorpholino oligonucleotides of this disclosure, and exemplary oligonucleotide chains that may be formed using these synthesis procedures (upper left box). X=Sulfur; y and n represent any combination of 2'-deoxynucleotide thiophosphate and thiomorpholino nucleotides. Although synthesis as shown in this figure is initiated with a 2'-methoxyuridine attached to the support, any 2'-deoxynucleoside, morpholino nucleoside, 2'-methoxynucleoside, 2'-methoxyethylnucleoside, or any other nucleoside can be used as the attachment site for synthesis of oligonucleotides.

Exemplary backbone structures for antisense thiomorpholino oligonucleotides of this disclosure include the thiomorpholino subunit types shown in FIGS. 1A and 1B, linked by a phosphorothioate-containing internucleotide linkages.

In certain embodiments, the antisense compounds can be prepared by stepwise solid-phase synthesis, employing methods detailed in PCT patent Application No. PCT/US17/51839, filed Sep. 15, 2017, and below with respect to the synthesis of oligonucleotides having a mixture of uncharged and cationic backbone linkages. In some cases, it may be desirable to add additional chemical moieties to the antisense compound, e.g., to enhance pharmacokinetics or to facilitate capture or detection of the compound. Such a moiety may be covalently attached, according to standard synthetic methods. For example, addition of a moiety to enhance cellular uptake (such as TAT), or an Fc binding immunoglobulin subunit, or a saccharide (such as a disaccharide, such as lactose), or a polyethylene glycol moiety or other hydrophilic polymer, e.g., one having 1-100 monomeric subunits, may be useful in enhancing solubility, increasing cellular uptake, or prolonging serum half-life, and the like.

A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense compound, it is desirable to select chemical compounds of groups that are biocompatible and likely to be tolerated by a subject without undesirable side effects.

Oligomers useful in the antisense applications of this disclosure generally range in length from about 8 to about 50 nucleotide residues, more preferably about 8 to 30 nucleotides, and typically 10-25 bases.

Each thiomorpholino (TMO) ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (e.g., the bases Adenine (A), Guanine (G), Cytosine (C), Thymine (T) or Uracil (U)) or an analog, such as hypoxanthine (the base component of the nucleoside inosine), or 5-methyl cytosine.

As noted above, embodiments include oligomers comprising novel internucleotide linkages, including TMO-X oligomers and those having modified terminal groups. These oligomers may have higher affinity for DNA and RNA than do the corresponding unmodified oligomers and demonstrate improved cell delivery, potency, and/or tissue distribution properties compared to oligomers having other internucleotide linkages. The structural features and properties of the various linkage types and oligomers are described in more detail in the following discussion. The synthesis of these and related oligomers is described in co-owned PCT patent Application No. PCT/US17/51839, filed Sep. 15, 2017, which is incorporated herein by reference in its entirety.

The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense molecule need not be 100% complementary to that of its target sequence to be specifically hybridizable. An antisense molecule is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

While the above method may be used to select antisense molecules capable of deleting any exon from within a protein that is capable of being shortened without affecting its biological function, the exon deletion should not lead to a reading frame shift in the shortened transcribed mRNA. Thus, if in a linear sequence of three exons, the end of the first exon encodes two of three nucleotides in a codon and the next exon is deleted then the third exon in the linear sequence must start with a single nucleotide that completes the nucleotide triplet for a codon. If the third exon does not commence with a single nucleotide there will be a reading frame shift that would lead to the generation of truncated or a non-functional protein.

It will be appreciated that the codon arrangements at the end of exons in structural proteins may not always break at the end of a codon, consequently there may be a need to delete more than one exon from the pre-mRNA to ensure in-frame reading of the mRNA. In such circumstances, a plurality of antisense oligonucleotides may need to be selected by the method of the invention wherein each is directed to a different region responsible for inducing splicing in the exons that are to be deleted.

The length of an antisense molecule may vary so long as it is capable of binding selectively to the intended location within the pre-mRNA molecule. The length of such sequences can be determined in accordance with selection procedures described herein. Generally, the antisense molecule will be from about 10 nucleotides in length up to about 50 nucleotides in length. It will be appreciated however that any length of nucleotides within this range may be used in the method. Preferably, the length of the antisense molecule is between 8-30 nucleotides in length.

The most common method for producing antisense molecules is the methylation of the 2' hydroxyribose position, and the incorporation of a phosphorothioate backbone produces molecules that superficially resemble RNA but that are much more resistant to nuclease degradation.

To avoid degradation of pre-mRNA during duplex formation with the antisense molecules, the antisense molecules used in these methods may be adapted to minimize or prevent cleavage by endogenous RNase H. This property is highly preferred as the treatment of the RNA with the unmethylated oligonucleotides either intracellularly or in crude extracts that contain RNase H leads to degradation of the pre-mRNA-antisense oligonucleotide duplexes. Any form of modified antisense molecules that is capable of by-passing or not inducing such degradation may be used in the present methods. An example of antisense molecules, which when duplexed with RNA, are not cleaved by cellular RNase H is 2'-O-methyl derivatives. 2'-O-methyl-oligoribonucleotides are very stable in a cellular environment and in animal tissues, and their duplexes with RNA have higher Tm values than their ribo- or deoxyribo-counterparts.

While antisense oligonucleotides are a preferred form of the antisense molecules, this disclosure comprehends other oligomeric antisense molecules, including but not limited to oligonucleotide mimetics.

Specific examples of preferred antisense compounds useful in this invention include oligonucleotides containing modified backbones or non-natural inter-nucleoside linkages. As defined in this specification, oligonucleotides having modified backbones include those that retain a phosphorothioate in the backbone and those that do not have a phosphorothioate in the backbone. For the purposes of this specification, and as sometimes referenced in the art, modified oligonucleotides that do not have a phosphorothioate in their inter-nucleoside backbone can also be considered to be oligonucleosides.

Modified oligonucleotides may also contain one or more substituted sugar moieties. Oligonucleotides may also include nucleobase (often referred to in the art simply as "base") modifications or substitutions. Certain nucleo-bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Another modification of the oligonucleotides of this disclosure involves chemically linking to the oligonucleotide one or more moieties or conjugates that enhance the activity, cellular distribution or cellular uptake of the oligonucleotide. Such moieties include but are not limited to lipid moieties such as a saccharide, such as the disaccharide lactose, a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

It is not necessary for all positions in a compound to be uniformly modified, and in fact more than one of the aforementioned modifications may be incorporated in a single compound or even at a single nucleoside within an oligonucleotide. This disclosure also includes antisense compounds that are chimeric compounds. "Chimeric" antisense compounds or "chimeras" are antisense molecules, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified to confer increased resistance to nuclease degradation, increased cellular uptake, and/or an additional region for increased binding affinity for the target nucleic acid.

III. Peptide Transporters

The antisense oligonucleotides of this disclosure may include oligonucleotide moieties conjugated to a CPP, preferably an arginine-rich peptide transport moiety effective to enhance transport of the compound into cells. The transport moiety is preferably attached to a terminus of the oligomer. The peptides have the capability of inducing cell penetration within 30%, 40%, 50%, 60%, 70%, 80%, 90%, or 100% of cells of a given cell culture population, including all integers in between, and allow macromolecular translocation within multiple tissues in vivo upon systemic administration. In one embodiment, the cell-penetrating peptide may be an arginine-rich peptide transporter. In another embodiment, the cell-penetrating peptide may be Penetratin or the TAT peptide. These peptides are well known in the art and are disclosed, for example, in US Patent Publication No. 2010/0016215, incorporated herein by reference in its entirety. A particularly preferred approach to conjugation of peptides to antisense oligonucleotides can be found in PCT publication No. WO2012/150960, which is incorporated herein by reference in its entirety. A preferred embodiment of a peptide conjugated oligonucleotides of this disclosure utilizes glycine as the linker between the CPP and the antisense oligonucleotide. For example, a preferred peptide conjugated PMO consists of R6-G-TMO. These transport moieties have been shown to greatly enhance cell entry of attached oligomers, relative to uptake of the oligomer in the absence of the attached transport moiety. Uptake is preferably enhanced at least ten-fold, and more preferably twenty-fold, relative to the unconjugated compound.

The use of arginine-rich peptide transporters (i.e., cell-penetrating peptides) are particularly useful in the compositions and methods of this disclosure. Certain peptide transporters have been shown to be highly effective at delivery of antisense compounds into primary cells including muscle cells (Marshall, Oda et al. 2007; Jearawiriyapaisarn, Moulton et al. 2008; Wu, Moulton et al. 2008). Furthermore, compared to other known peptide transporters, such as Penetratin and the TAT peptide, the peptide transporters described herein, when conjugated to an antisense TMO, demonstrate an enhanced ability to alter splicing of several gene transcripts (Marshall, Oda et al. 2007).

IV. Formulations and Treatment

This disclosure also provides formulations or compositions suitable for the therapeutic delivery of antisense oligomers to a subject. These compositions may be pharmaceutically acceptable compositions that comprise a therapeutically-effective amount of one or more of the oligomers described herein, formulated together with one or more pharmaceutically acceptable carriers (additives) and/or diluents. While it is possible for an oligomer of this disclosure to be administered alone, it is preferable to administer the compound as a pharmaceutical formulation (composition).

The compositions of this disclosure may be administered alone or in combination with another therapeutic. The additional therapeutic may be administered prior to, concurrent with, or subsequent to the administration of the compositions of the present invention. For example, the compositions may be administered in combination with a steroid and/or an antibiotic. The steroid may be a glucocorticoid or prednisone. Other agents which may be administered include an antagonist of the ryanodine receptor, such as dantrolene, which has been shown to enhance antisense-mediated exon skipping in patient cells and a mouse model of DMD (G. Kendall et al. Sci Tranl Med 4 164ra160 (2012)).

Methods for the delivery of nucleic acid molecules are described, for example, in Akhtar et al., 1992, Trends Cell Bio., 2:139; and Delivery Strategies for Antisense Oligonucleotide Therapeutics, ed. Akhtar; Sullivan et al., PCT WO 94/02595. These and other protocols can be utilized for the delivery of virtually any nucleic acid molecule, including the isolated oligomers of the present invention.

As detailed below, the pharmaceutical compositions of this disclosure may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Examples of materials that can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Additional non-limiting examples of agents suitable for formulation with the antisense oligomers of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues; biodegradable polymers, such as poly (DL-lactide-coglycolide) microspheres for sustained release delivery after implantation (Emerich, D F et al., 1999, Cell Transplant, 8, 47-58) Alkermes, Inc. Cambridge, Mass.; and loaded nanoparticles, such as those made of mesoporus silica, or polybutylcyanoacrylate, which can deliver drugs across the blood brain barrier and can alter neuronal uptake mechanisms (Prog Neuropsychopharmacol Biol Psychiatry, 23, 941-949, 1999).

These compositions may also comprise liposomes or lipoplexes, including surface-modified liposomes/lipoplexes containing saccharides and/or poly(ethylene glycol) lipids (PEG-modified, branched and unbranched or combinations thereof, or long-circulating liposomes or stealth liposomes). Oligomers of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug. Such liposomes/lipoplexes have been shown to accumulate selectively in tumors. The long-circulating liposomes/lipoplexes may enhance the pharmacokinetics and pharmacodynamics of DNA and RNA, particularly compared to conventional cationic liposomes. Long-circulating liposomes are also likely to protect drugs from nuclease degradation to a greater extent compared to cationic liposomes, based on their ability to avoid accumulation in metabolically aggressive MPS tissues such as the liver and spleen.

This disclosure includes oligomer compositions prepared for delivery as described in U.S. Pat. Nos. 6,692,911, 7,163,695 and 7,070,807. Thus, this disclosure provides an oligomer of this disclosure in a composition comprising copolymers of lysine and histidine (HK) (as described in U.S. Pat. Nos. 7,163,695; 7,070,807; and 6,692,911) either alone or in combination with PEG (e.g., branched or unbranched PEG or a mixture of both), in combination with PEG and a targeting moiety or any of the foregoing in combination with a crosslinking agent. This disclosure also provides antisense oligomers in compositions comprising gluconic-acid-modified polyhistidine or gluconylated-polyhistidine/transferrin-polylysine. Amino acids with properties similar to His and Lys may be substituted within the composition.

The oligomers described herein may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the subject oligomers include the conventional nontoxic salts or quaternary ammonium salts of the compounds, e.g., from nontoxic organic or inorganic acids. For example, conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

The oligomers of this disclosure may contain one or more acidic functional groups and, thus, are capable of forming pharmaceutically-acceptable salts with pharmaceutically-acceptable bases. The term "pharmaceutically-acceptable salts" in these instances refer to the relatively non-toxic, inorganic and organic base addition salts of the TMO compounds of this disclosure. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in these compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Useful formulations of this disclosure include those suitable for oral, nasal, topical (including buccal and sublingual), rectal, vaginal, and/or parenteral administration. The formulations may conveniently be presented in unit dosage form and may be prepared by any methods well known in the art of pharmacy. The amount of active ingredient that can be combined with a carrier material to produce a single dosage form will vary depending upon the host being treated, and the mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

A formulation of this disclosure may comprise an excipient selected from cyclodextrins, celluloses, liposomes, micelle forming agents, e.g., bile acids, and polymeric carriers, e.g., polyesters and polyanhydrides; and an oligomer of the present invention, that may render orally bioavailable an oligomer of this disclosure.

Methods of preparing these formulations or compositions include the step of bringing into association an oligomer of this disclosure with the carrier and, optionally, one or more accessory ingredients. In general, the formulations are prepared by uniformly and intimately bringing into association a compound of this disclosure with liquid carriers, or finely divided solid carriers, or both, and then, if necessary, shaping the product.

The formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of this disclosure as an active ingredient. An oligomer of this disclosure may also be administered as a bolus, electuary or paste.

In these solid dosage forms for oral administration (capsules, tablets, pills, dragees, powders, granules, trouches and the like), the active TMO therapeutic ingredient may be mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (e.g., gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in microencapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations or dosage forms for the topical or transdermal administration of an oligomer as provided herein include powders, sprays, ointments, pastes, creams, lotions, gels, solutions, patches and inhalants. The active oligomers may be mixed under sterile conditions with a pharmaceutically-acceptable carrier, and with any preservatives, buffers, or propellants which may be required. The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an oligomer of the present invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an oligomer of this disclosure to the body. Such dosage forms can be made by dissolving or dispersing the oligomer in the proper medium. Absorption enhancers can also be used to increase the flux of the agent across the skin. The rate of such flux can be controlled by either providing a rate controlling membrane or dispersing the agent in a polymer matrix or gel, among other methods known in the art.

Pharmaceutical compositions suitable for parenteral administration may comprise one or more oligomers of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by using coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject oligomers may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by using a liquid suspension of crystalline or amorphous material having poor water solubility, among other methods known in the art. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms may be made by forming microencapsulated matrices of the subject oligomers in biodegradable polymers such as polylactide-polyglycolide. Depending on the ratio of oligomer to polymer, and the nature of the particular polymer employed, the rate of oligomer release can be controlled. Examples of other biodegradable polymers include poly(orthoesters) and poly(anhydrides). Depot injectable formulations may also be prepared by entrapping the drug in liposomes or microemulsions that are compatible with body tissues.

When the oligomers of this disclosure are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

As noted above, the formulations or preparations of this disclosure may be given orally, parenterally, systemically, topically, rectally, or intramuscular administration. They are typically given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Regardless of the route of administration selected, the oligomers of the present invention, which may be used in a suitable hydrated form, and/or the pharmaceutical compositions of the present invention, may be formulated into pharmaceutically-acceptable dosage forms by conventional methods known to those of skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration, without being unacceptably toxic to the patient.

The selected dosage level will depend upon a variety of factors including the activity of the particular oligomer of this disclosure employed, or the ester, salt or amide thereof, the route of administration, the time of administration, the rate of excretion or metabolism of the particular oligomer being employed, the rate and extent of absorption, the duration of the treatment, other drugs, compounds and/or materials used in combination with the particular oligomer employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and gradually increase the dosage until the desired effect is achieved. In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular, intramuscular and subcutaneous doses of the compounds of this invention for a patient, when used for the indicated effects, will range from about 0.0001 to about 100 mg per kilogram of body weight per day.

Preferred doses of the thiomorpholino oligomers of this disclosure are administered generally from about 5-100 mg/kg. In some cases, doses of greater than 100 mg/kg may be necessary. For i.v. administration, preferred doses are from about 0.1 mg to 100 mg/kg. In some embodiments, the thiomorpholino oligomers are administered at doses of about 2 mg/kg, to about 100 mg/kg, including all integers in between.

If desired, the effective daily dose of the active compound may be administered as two, three, four, five, six or more sub-doses administered separately at appropriate intervals throughout the day, optionally, in unit dosage forms. In certain situations, dosing is one administration per day. The dosing frequency is one or more administration per every 2, 3, 4, 5, 6, 7, 8, 9, 10, 11, 12, 13, 14 days, or every 1, 2, 3, 4, 5, 6, 7, 8, 9, 10, 11, 12 weeks, or every 1, 2, 3, 4, 5, 6, 7, 8, 9, 10, 11, 12 months, as needed, to maintain the desired expression of a functional dystrophin protein in the subject.

In some embodiments, the oligomers of this disclosure are administered, generally at regular intervals (e.g., daily, weekly, biweekly, monthly, bimonthly). The oligomers may be administered at regular intervals, e.g., daily; once every two days; once every three days; once every 3 to 7 days; once every 3 to 10 days; once every 7 to 10 days; once every week; once every two weeks; once monthly. For example, the oligomers may be administered once weekly by intravenous infusion. The oligomers may be administered intermittently over a longer period, e.g., for several weeks, months or years. For example, the oligomers may be administered once every: one, two, three, four, five, six, seven, eight, nine, ten, eleven or twelve months. In addition, the oligomers may be administered once every: one, two, three, four or five years. Administration may be followed by, or concurrent with, administration of an antibiotic, steroid or other therapeutic agent. The treatment regimen may be adjusted (dose, frequency, route, etc.) as indicated, based on the results of immunoassays, other biochemical tests and physiological examination of the subject under treatment.

Nucleic acid molecules can be administered to cells by a variety of methods known to those familiar to the art, including, but not restricted to, encapsulation in liposomes or lipoplexes, by iontophoresis, or by incorporation into other vehicles, such as hydrogels, cyclodextrins, biodegradable nanocapsules, and bioadhesive microspheres, as described herein and known in the art. In certain embodiments, microemulsification technology may be utilized to improve bioavailability of lipophilic (water insoluble) pharmaceutical agents. Among other benefits, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize the compound of this disclosure and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Examples of amphiphilic carriers include saturated and monounsaturated polyethylene-glycolyzed fatty acid glycerides, such as those obtained from fully or partially hydrogenated various vegetable oils. Such oils may advantageously consist of tri-, di-, and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palm itic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

The delivery may occur by use of liposomes, lipoplexes, nanocapsules, microparticles, microspheres, lipid particles, vesicles, and the like, for the introduction of the compositions of this disclosure into suitable host cells. In particular, the compositions of this disclosure may be formulated for delivery either encapsulated in a lipid particle, a liposome, a lipoplex, a vesicle, a nanosphere, a nanoparticle, or the like. The formulation and use of such delivery vehicles can be carried out using known and conventional techniques.

Hydrophilic polymers which may be suitable for use in this disclosure include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

A formulation of this disclosure may comprise a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letters alpha, beta, or gamma, respectively. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds. The complexation takes place by Van der Waals interactions and by hydrogen bond formation. The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 micrometers in diameter; large unilamellar vesicles (LUVS) are typically larger than 0.05 micrometers Oligolamellar large vesicles and multilamellar vesicles have multiple, usually concentric, membrane layers and are typically larger than 0.1 micrometers. Liposomes with several nonconcentric membranes, i.e., several smaller vesicles contained within a larger vesicle, are termed multivesicular vesicles. Thus, formulations comprising liposomes containing a thiomorpholino oligomer of this disclosure, where the liposome membrane is formulated to provide a liposome with increased carrying capacity. Alternatively, or additionally, the compound of this disclosure may be contained within, or adsorbed onto, the liposome bilayer of the liposome. An oligomer of this disclosure may be aggregated with a lipid surfactant and carried within the liposome's internal space; in these cases, the liposome membrane is formulated to resist the disruptive effects of the active agent-surfactant aggregate. The lipid bilayer of these liposomes may contain lipids derivatized with a saccharide, including a disaccharide such as lactose, a polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of this disclosure are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPGs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMOs in the micromolar range; higher CMC surfactants may be utilized to prepare micelles entrapped within liposomes of the present invention.

Liposomes according to this disclosure may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993. For example, liposomes of this disclosure may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988). In certain embodiments, reagents such as DharmaFECT™ and Lipofectamine™ may be utilized to introduce polynucleotides or proteins into cells.

The release characteristics of a formulation of this disclosure depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In most cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween™ and Pluronic™. Pore forming agents which add microstructure to the matrices (i.e., water soluble compounds such as inorganic salts and sugars) are added as particulates. The range is typically between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

In addition to the methods provided herein, the oligomers for use according to the invention may be formulated for administration in any convenient way for use in human or veterinary medicine, by analogy with other pharmaceuticals. The antisense oligomers and their corresponding formulations may be administered alone or in combination with other therapeutic strategies in the treatment of muscular dystrophy, such as myoblast transplantation, stem cell therapies, administration of aminoglycoside antibiotics, proteasome inhibitors, and up-regulation therapies (e.g., upregulation of utrophin, an autosomal paralogue of dystrophin).

EXAMPLES

Example 1: Design and Synthesis of Thiomorpholino Antisense Oligonucleotides (AOs)

All chemicals were purchased from Sigma-Aldrich unless otherwise noted. Standard reagents used in automated DNA synthesis as well as 5'-dimethoxytrityl-2'-deoxyribo 3'-[(Cyanoethyl)-(N,N-diisopropylamino)]-phosphoramidites (9, 10, 11 or 12) were purchased from Glen Research. Nucleosides and 2-cyanoethyl-N,N,N',N'-tetraisopropyl-phosphorodiamidate were purchased from ChemGenes Corporation. Deuterated solvents were purchased from Cambridge Isotopes.

NMR experiments were carried out on a Bruker Avance-III 400 (1H=400.13 MHz). Chemical shifts are given in ppm with positive shifts downfield. All 1H and 13C chemical shifts were referenced relative to internal residual protons from a lock solvent. 31P Chemical shifts are referenced to 0.0 ppm in the 1H NMR spectrum according to the standard IUPAC method.

The 5' dimethoxytrityl protected nucleosides were dissolved in methanol followed by addition of 1.2 equivalents of sodium periodate and ammonium biborate tetrahydrate (1.2 equivalents). The mixture was stirred at room temperature for three hours when TLC indicates complete consumption of the starting material. The reaction mixture was filtered through a pad of celite and were added activated powdered 4 A° molecular sieves (0.4 g/mmol) followed by addition of 2.0 equivalents of sodium cyanoborohydride and glacial acetic acid (2.0 equivalents). This reaction mixture was then stirred for another 4-5 h when the intermediate diol was completely reduced. Reaction mixtures were filtered through a pad of celite and evaporated to dryness. The residue was dissolved in chloroform and washed with saturated $NaHCO_3$ and brine. The organic layer was collected, dried over $Na_2SO_4$ and removed under reduced pressure. Products were purified by flash chromatography on a silica gel column. In all cases the silica gel slurry was prepared with the starting eluant mixture containing an additional 5% triethylamine. After pouring the slurry, the column was washed with two column volumes of the starting solvent mixture containing no triethylamine. Compounds 1, 2, 3, and 4 were eluted using a gradient of chloroform to 19:1 chloroform-methanol. All the yields described in the following sections represent those obtained over two steps starting from the 5'-Dimethoxytrityl-N-protected nucleosides.

Synthesis of phosphorodiamidate monomers for thiomorpholino synthesis: The general procedure for the synthesis of the monomers (compounds 5, 6, 7 or 8) is depicted in the synthesis scheme of FIG. 1A. Briefly, 5'-O-DMT-protected morpholino nucleosides (1, 2, 3 or 4) were dried overnight in vacuum, and dissolved in anhydrous $CH_2Cl_2$ followed by addition of 1.2 equivalents of 2-cyanoethyl-N,N,N',N'-tetraisopropyl-phosphorodiamidate under argon. After adding 0.5 equivalent of 4,5-dicyano imidazole the reaction was allowed to stir for 30 minutes under argon atmosphere at room temperature when TLC indicates complete conversion of starting material. The reaction mixture was evaporated to dryness. As described above, the silica gel slurry was prepared with the starting eluant mixture containing an additional 5% triethylamine. After pouring the slurry, the column was washed with two column volumes of the starting solvent mixture containing no triethylamine. Compounds 5, 6, 7 and 8 were purified using 50% ethylacetate-hexane.

5'-dimethoxytrityl-morpholinothymidine-3'-N-cyanoethyl-N,Ndiisopropyl phosphorodiamidate (5): Yield: 76%. $^{31}P$ NMR ($CD_3CN$) δ: 127.90, 127.89. $^1H$ NMR ($CD_2Cl_2$, 400 MHz) δ: 9.51 (1H, bs), 7.50-7.47 (2H, m), 7.38-7.25 (8H, m), 6.89-6.86 (4H, m), 5.78-5.75 (0.5H, dd), 5.65-5.62 (0.5H, dd), 4.08-4.02 (1H, m), 3.99-3.86 (3H, m), 3.82 (6H, s), 3.65-3.52 (2H, m), 3.48-3.34 (1H, m), 3.31-3.27 (1H, m), 3.13-3.09 (1H, m), 2.75-2.68 (2H, m), 2.53-2.47 (2H, m), 1.96 (3H, m), 1.25-1.18 (12H, m). $^{13}C$ NMR ($CD_2Cl_2$) δ: 164.02, 163.96, 158.66, 150.13, 144.95, 135.92, 135.90, 135.79, 135.68, 135.52, 129.99, 128.07, 127.77, 126.77, 117.89, 117.74, 113.05, 110.48, 110.39, 86.05, 80.54, 80.49, 80.20, 77.36, 77.21, 64.37, 60.09, 59.84, 55.20, 49.05, 48.83, 47.58, 47.06, 46.83, 45.87, 45.78, 43.91, 43.74, 24.36, 24.29, 24.22, 24.20, 20.77, 20.33, 20.66, 12.29. ESI-MS (m/z): 727.4047 $(M+H)^+$.

$N^2$-benzoyl-5'-dimethoxytrityl-morpholinocytidine-3'-N-cyanoethyl-N,N-diisopropyl phosphorodiamidate (6): Yield: 60%. $^{31}P$ NMR ($CD_3CN$) δ: 127.35, 127.25. $^1H$ NMR ($CD_2Cl_2$, 400 MHz) δ: 7.99-7.96 (3H, m), 7.67-7.64 (1H, m), 7.56-7.49 (5H, m), 7.39-7.26 (7H, m), 6.89-6.87 (4H, m), 5.83-5.67 (1H, m), 4.11-4.07 (1H, m), 4.09-3.87 (2H, m), 3.83 (6H, s), 3.81-3.77 (1H, m), 3.65-3.48 (3H, m), 3.37-3.25 (2H, m), 3.19-3.15 (1H, m), 2.78-2.75 (1H, m), 2.72-2.68 (1H, m), 2.56-2.53 (1H, m), 2.39-2.33 (1H, m), 1.25-1.18 (12H, m). $^{13}C$ NMR ($CD_2Cl_2$) δ: 162.22, 158.65, 144.94, 135.92, 135.78, 133.01, 130.05, 130.00, 128.89, 128.06, 127.80, 127.64, 126.79, 117.91, 117.77, 113.05, 86.04, 82.17, 81.93, 77.36, 64.40, 60.22, 60.11, 59.87, 49.85, 49.62, 48.22, 48.17, 47.05, 46.81, 45.70, 45.63, 43.94, 43.88, 43.82, 43.77, 24.38, 24.30, 24.24, 24.16, 20.34, 20.30, 20.22. ESI-MS (m/z): 833.3801 (M+H)$^+$.

$N^2$-benzoyl-5'-dimethoxytrityl-morpholinoadenosine-3'-N-cyanoethyl-N,N-diisopropyl phosphorodiamidate (7): Yield: 62%. $^{31}$P NMR (CD$_3$CN) δ: 128.27, 126.42. $^1$H NMR (CD$_2$Cl$_2$, 400 MHz) δ: 9.15 (1H, s), 8.78 (1H, s), 8.25-8.24 (1H, d), 8.03-8.01 (2H, m), 7.67-7.63 (1H, m), 7.58-7.54 (2H, m), 7.51-7.47 (2H, m), 7.38-7.24 (7H, m), 6.04-5.90 (1H, m), 4.18-4.11 (1H, m), 4.09-4.05 (1H, m), 4.00-3.89 (2H, m), 3.86 (1H, bs), 3.83 (6H, s), 3.70-3.54 (3H, m), 3.42-3.31 (2H, m), 3.19-3.15 (1H, m), 2.99-2.89 (1H, m), 2.77-2.74 (1H, m), 2.72-2.62 (2H, m), 1.27-1.21 (12H, m). $^{13}$C NMR (CD$_2$Cl$_2$) δ: 158.64, 152.41, 152.32, 149.56, 144.92, 140.71, 135.86, 135.74, 134.02, 132.60, 130.00, 128.79, 128.04, 127.78, 126.77, 123.19, 123.11, 117.81, 117.74, 113.04, 86.08, 80.81, 80.60, 77.15, 64.27, 60.14, 59.80, 50.27, 50.04, 48.66, 47.29, 47.06, 45.97, 43.92, 43.72, 24.24, 24.19, 20.29. ESI-MS (m/z): 857.3911 (M+H)$^+$.

$N^2$-isobutyryl-5'-dimethoxytrityl-morpholinoguanosine-3'-N-cyanoethyl-N,N-diisopropyl phosphorodiamidate (8): Yield: 33%. $^{31}$P NMR (CD$_3$CN) δ: 129.43, 124.17. $^1$H NMR (CD$_2$Cl$_2$, 400 MHz) δ: 12.02 (1H, s), 7.89-7.86 (1H, m), 7.52-7.47 (2H, m), 7.40-7.27 (7H, m), 6.90-6.86 (4H, m), 5.67-5.66 (1H, m), 4.14-4.09 (1H, m), 4.06-4.02 (1H, m), 4.00-3.85 (2H, m), 3.83 (6H, s), 3.74-3.68 (1H, m), 3.52-3.27 (3H, m), 3.21-3.17 (1H, m), 2.88-2.60 (5H, m), 1.27-1.22 (12H, m), 1.19-1.15 (6H, m). $^{13}$C NMR (CD$_2$Cl$_2$) δ: 179.29, 178.97, 158.67, 147.82, 144.93, 136.17, 135.74, 130.04, 128.04, 127.79, 126.79, 121.16, 121.06, 118.49, 118.07, 113.06, 86.12, 81.61, 81.46, 77.15, 77.03, 76.77, 64.31, 64.24, 60.23, 59.51, 59.27, 50.39, 50.20, 48.20, 47.53, 47.19, 46.67, 46.64, 45.54, 45.48, 43.81, 43.69, 43.53, 43.42, 36.22, 35.97, 24.55, 24.47, 24.43, 24.35, 24.24, 24.17, 24.03, 20.79, 20.71, 20.62, 20.56, 20.48, 18.76, 18.63, 18.58. ESI-ESI-MS (m/z): 839.4019 (M+H)+.

Figure 5:
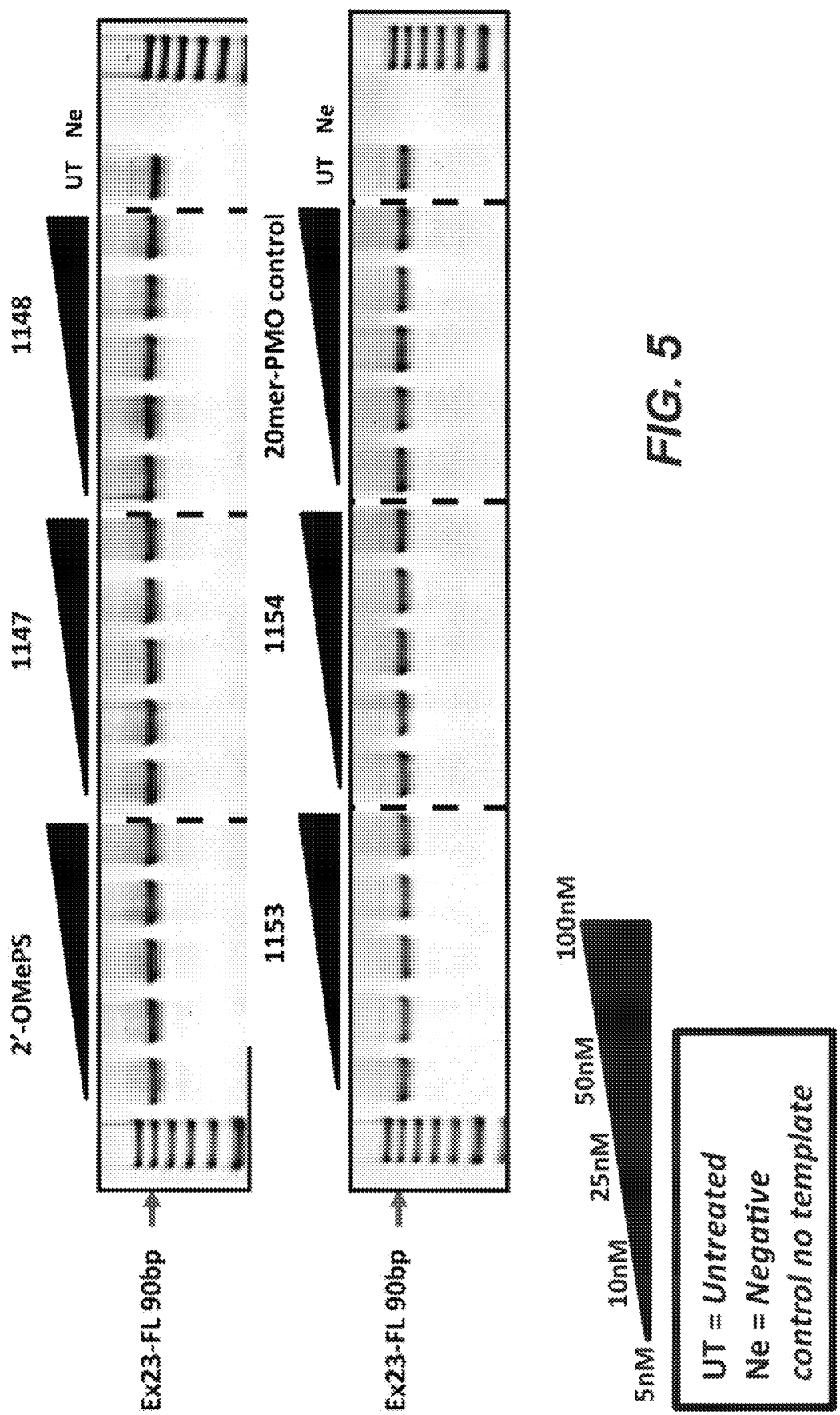
FIG. 5 shows a summary of the results from exon skipping of exon 23 when the transfection was conducted over one day in the absence of either lipofectin or lipofectamine.

Solid Phase Synthesis: The procedure used to synthesize TMO and TMO-DNA chimeras is described in the synthesis scheme depicted in FIG. 1B: Prior to synthesis, the 5'-O-DMTr group on the 2'-OMe-ribouridine linked to a controlled pore glass support was removed with 3% trichloroacetic acid in dichloromethane. It is also possible to use 2'-deoxynucleosides linked to the controlled pore glass. The 5'-unprotected-2'-OMe-ribouridine (A) was then allowed to react (5 minutes) with compounds 5, 6, 7 or 8 in anhydrous acetonitrile containing a 0.12 molar solution of 4,5-dicyanoimidazole (DCI) as shown in FIG. 1B or 5-(ethylthio)-1H-tetrazole. (5-(ethylthio)-1H-tetrazole may also be used as an activator at this step) to generate a dimer having a phosphoramidite-diester-internucleotide linkage (B). This intermediate was converted to (D) by treatment with 3-((N, N-dimethylaminomethylidene)amino)-3H-1,2,4-dithiazole-5-thione (DDTT) for sulfurization and the support was next treated with a solution of acetic anhydride in order to cap any unreacted 5'-hydroxyl groups. For the preparation of thiophosphoramidate morpholino DNA chimeras (TMO/DNA), the synthesis cycle was similar except that 0.12M 5-(ethylthio)-1H-tetrazole was the activator with 5'-O-dimethoxytrityl-2'-deoxyribonucleoside-3'-phosphoramidite synthons (9, 10, 11 or 12) to obtain (C). This phosphite triester was then converted to (E) by oxidation with DDTT to generate phosphorothioate internucleotide linkages. The products of these condensations (E) were then capped with acetic anhydride. Following treatment with 3% trichloroacetic acid in dichloromethane, (F) or (G) were ready for repetitions of the appropriate cycle to generate the TMO or TMO-DNA chimeras.

DMT-ON oligonucleotides were deprotected in ammonium hydroxide (1.0 mL) at 55° C. for 18 hours and purified using RP-HPLC. The DMT moiety was removed with 50% aqueous acetic acid over 5 minutes at room temperature followed by quenching with TEA to pH 7.0, followed by evaporation under reduced pressure. The resulting oligonucleotides were isolated using RP-HPLC.

These TMO and TMO-DNA chimeras were characterized by LCMS.

Automated TMO Synthesis: Syntheses were carried out on an ABI 394 Synthesizer. All syntheses were performed at a 1.0 μmol scale using a 5'-DMTr-2'-OMe-ribouridine joined to a CPG solid support via a succinate linkage. It is also possible to use 2'-deoxynucleosides linked to the controlled pore glass. For the synthesis of thiomorpholino oligonucleotides, the phosphoramidites (5, 6, 7 or 8; 0.1 M) were dissolved in anhydrous CH$_3$CN. The standard 1.0μ mole synthesis cycle was used with an increase in coupling time to 300 s. Following oxidation and capping, detritylations were carried out using a 3% solution of trichloroacetic acid in dichloromethane. A stepwise description of the synthesis cycle is described in Table 1. All syntheses were carried out with DMT ON. Following synthesis, resins were transferred to a 1.5 mL screw cap vial and treated with 1.0 mL NH$_4$OH (37%) for 18 h at 55° C.

TABLE 1

Chemical Steps used to Prepare Thiomorpholino Oligonucleotides.

| Reactions | Wash/Reagents/Solvents | Time (s) |
| --- | --- | --- |
| Detritylation | 3% trichloroaceticacid in dichloromethane | Flow 90 s |
| Condensation | 0.1M phosphordiamidite 5, 6, 7 or 8 (CH$_3$CN) + Activator* (0.12M dicyanoimidazole in CH$_3$CN) (or 0.12M Ethylthiotetrazole in CH$_3$CN) Or | Wait 300 s |
|  | 0.1M phosphoramidite9, 10, 11 or 12 in CH$_3$CN + Activator* (0.25M ethylthiotetrazolein CH$_3$CN) | Wait 180 s |
| Sulfurization | 3-((N,N-dimethylaminomethylidene)amin)3H-1,2,4-dithiazole-5-thione in pyridine, acetonitrile; 3:2 | Flow 15 s, wait 90 s |
| Wash | Anhydrous CH$_3$CN | Flow 10 s |
| Capping | Cap A* (THF/Pyridine/AcO$_2$) + Cap B * (16% 1-methylimidazole in THF)0 | Flow 10 s, wait 5 s |
| Wash | Anhydrous CH$_3$CN | Flow 10 s |
| Wash | Anhydrous CH$_2$Cl$_2$ | Flow 25 s |

The RP-HPLC purification protocol: A linear gradient of 0 to 40% B over 30 min at a flow rate of 1.0 mL/min; buffer A: 50 mM TEAB, pH 8.5; buffer B: acetonitrile, room temperature. Column specifications: XBridge Oligonucleotide BEH C18 Prep Column, 130 Å, 2.5 μm, 10 mm×50 mm. This purification step yields the product as a broad peak due to the presence of multiple chiral phosphorus centers.

LC-MS analyses were carried out on an Agilent 6530 series Q-TOF LC/MS spectrometer. A Waters ACQUITY UPLC BEH C18, 1.7 μm, 2.1×100 nm column was used with a gradient of 0-100% of buffer B in 50 min with a flow rate of 0.2 mL/min (Buffer A was 1:380:10:10.4 mixture of triethylamine:water:methanol:hexafluoro-2-propanol and Buffer B was 1:370:20:10.4 mixture of triethylamine:methanol:water:hexafluoro-2-propanol).

Example 2: Melting Temperature Study of the Antisense Oligonucleotides

Six antisense oligonucleotides (sequences and internucleotide linkages shown in FIGS. 1C and 1D): control 2'-O-MePS, ODNs 1147, 1148, 1153, 1154, and the fully-modified PMO were prepared at 2 μM concentration in melting buffer containing 10 mM NaCl, 0.01 mM EDTA adjusted to pH 7.0 by 10 mM sodium phosphate buffer. The AOs were then mixed with the synthetic complementary RNA sequence (2 μM) at equal volume and denatured at 95° C. for 10 minutes, cooled down to room temperature and loaded onto a 1-mm path-length quartz cuvettes. The melting process was monitored by Shimadzu UV-1800 with the temperature controller over the range of 20-90° C. with ramp rate at 1.0° C./min. Tm values were calculated by the first derivative method. The melting temperatures for studied ODNs and control oligonucleotides were:

| ODN | Melting Temperature (Tm ° C.) |
|---|---|
| 1147 | 51.2 |
| 1148 | 58.7 |
| 1153 | 57.1 |
| 1154 | 61.3 |
| 2'-OMe PS | 62.9 |
| PMO | 71.6 |

Thus, all four ODNs have comparable melting temperature in a range that is useful for antisense studies.

Example 3: In Vitro Transfection of ODNs with Thiomorpholino ODNs

H-2K$^b$-tsA58 mdx myoblasts ("H2K mdx cells") were cultured and differentiated. Briefly, when reaching 60-80% confluence, myoblast cultures were treated with trypsin and seeded on 24 well plates pre-treated with 50 μg/ml poly-D-lysine, followed by 100 μg/ml Matrigel (In Vitro Technologies) at a density of 2×10$^4$ cells/well. Cells were then differentiated into myotubes in Dulbecco's Modified Eagle Medium (DMEM) containing 5% horse serum by incubating at 37° C., 5% CO$_2$, for 24 hours. Antisense oligonucleotides were then complexed with either Lipofectin at the ratio of 2:1 (w:w) (lipofectin:AO) or Lipofectamine 3000 (1.5 uL) and used in a final transfection volume of 500 μl/well in a 24-well plate per the manufacturer's instructions, except that the solution was not removed after 3 hours. The inventors also transfected the AOs naked (without using any transfection agents).

Twenty-four hours after transfection, cells were collected and RNA was extracted using Direct-zol™ RNA MiniPrep Plus with TRI Reagent (Zymo Research) per the manufacturer's instructions. The dystrophin transcripts were then analysed by nested RT-PCR using SuperScript™ III Reverse Transcriptase III and AmpliTaq Gold 360 DNA Polymerase across exons 20-26. PCR products were separated on 2% agarose gels in Tris-acetate-EDTA buffer and the images were captured on a Fusion Fx gel documentation system (Vilber Lourmat).

Quantitation of exon-skipping efficiency was conducted by densitometry analysis of the gel images. Densitometry was performed by Image J2 software using the captured gel images. Background was subtracted from the image using the "subtract background" function of the software and set at 50% (default value). The exon-skipping efficiency was determined by expressing the detected amount of exon-23 skipped RT-PCR product (the exact value of exon-23 skipped band) over the percentage of total dystrophin transcript product (total value of all the bands in each lane). The percentage values were then plotted using a 100% stacked column format in Microsoft Excel.

Figure 2A:
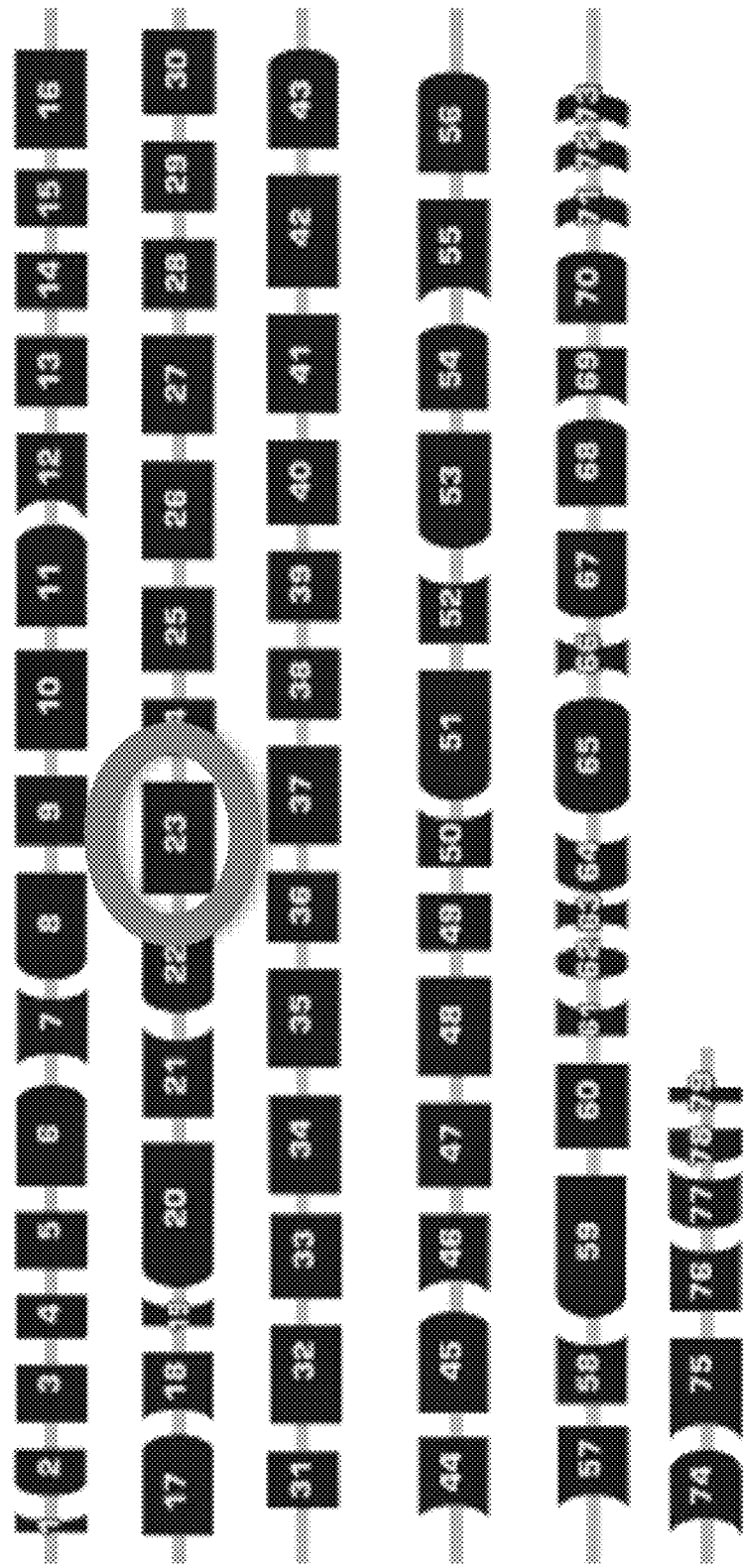
FIGS. 2A-2C show a model of the induction of exon skipping in mouse Duchenne Muscular Dystrophy. (A) depicts a map of the endogenous dystrophin mRNA, including both exons and introns. (B) shows the approach used to induce exon skipping of exon 23, resulting in the production of an active Dystrophin protein. (C) shows the specific ODN sequence (SEQ ID NO: 2) and how it overlaps the exon/intron boundary in dystrophin mRNA exon 23 (SEQ ID NO:1).
Figure 2B:
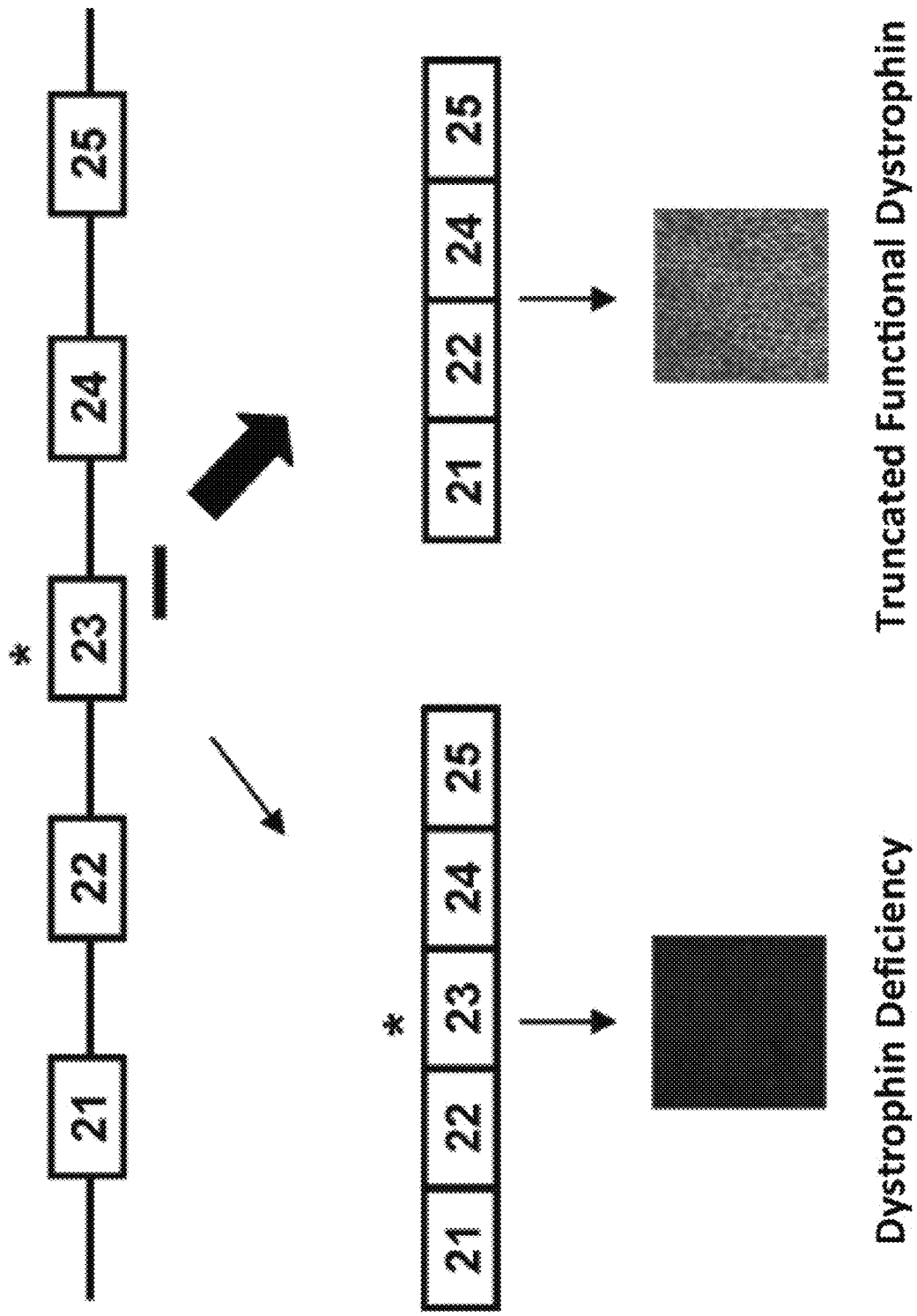
Figure 2C:
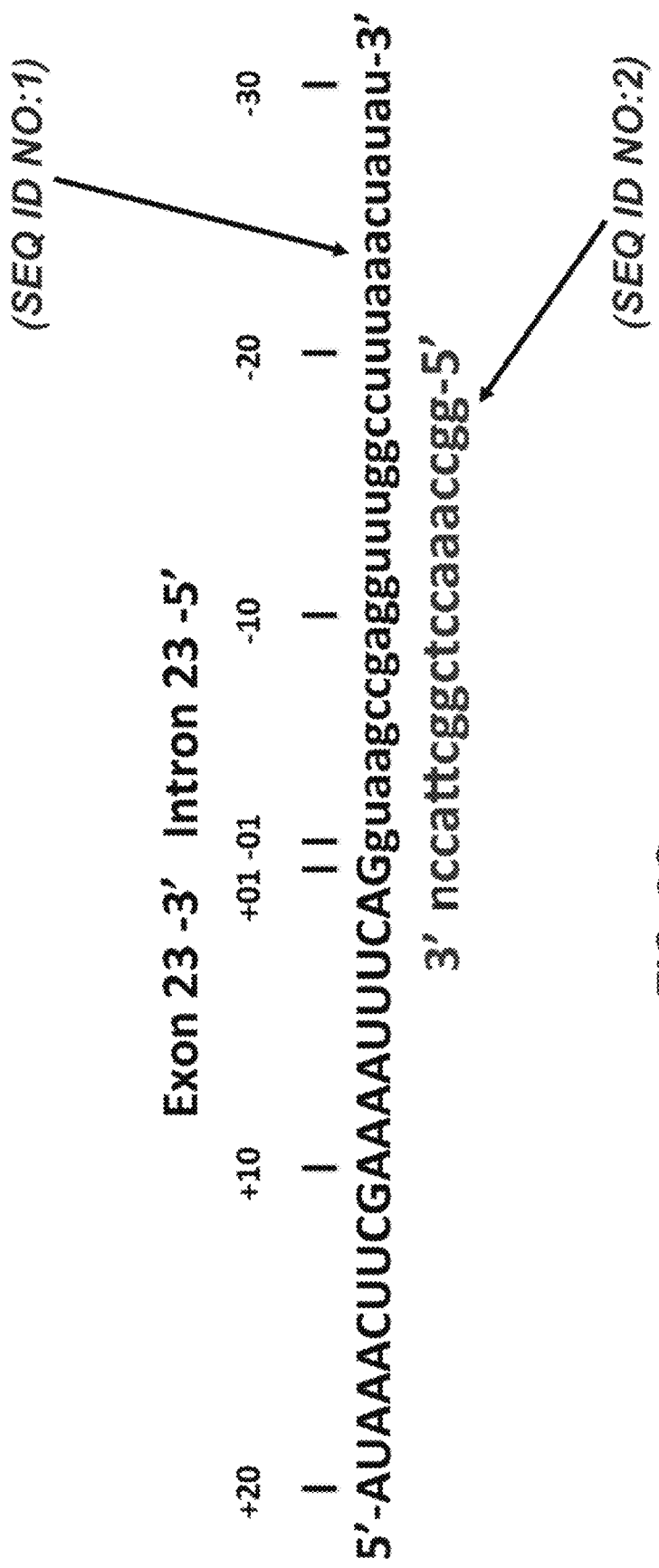

Results with the Duchenne Muscular Dystrophy Exon 23 Mouse Model: FIGS. 2A-2C depict the approach used to study exon skipping in the H2K mdx cells. FIG. 2A displays the endogenous mRNA, including both exons and introns. FIG. 2B outlines the general approach used to induce exon skipping of exon 23 that contains a fatal mutation that causes the production of a nonfunctional Dystrophin protein. The approach involves introducing an oligonucleotide (shown by the solid black line) whose sequence spans the exon/intron junction adjacent to this exon. This oligonucleotide blocks splicing at this junction and therefore the splicing complex skips exon 23 and generates a truncated mature mRNA, which, by translation, produces an active Dystrophin protein. FIG. 2C shows the specific ODN sequence and how it overlaps the exon/intron boundary. ODNs 1147, 1148, 1153, and 1154 all contain the same sequence elements but have variable numbers and locations of thiomorpholino nucleotides as shown in FIGS. 1C and 1D. These ODNs were transfected into the H2K mdx mouse myotubes cell line.

Figure 3:
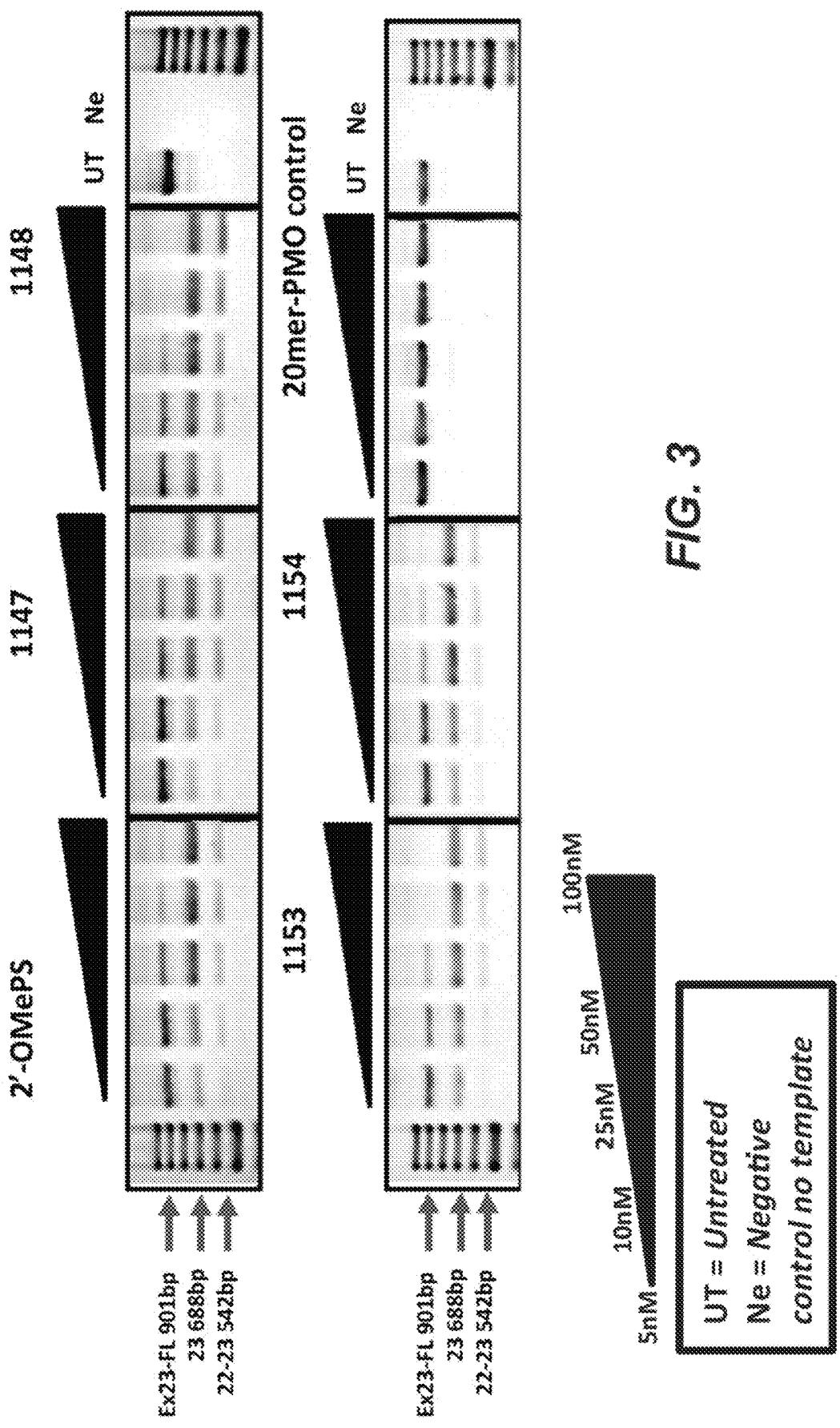
FIG. 3 shows a summary of the results from exon skipping of exon 23 when the transfection was conducted over one day with lipofectin.

When these ODNs are transfected into the mouse cell line with lipofectin (24 hours), exon skipping is observed with all four ODNs (ODNs 1147, 1148, 1153, and 1154) that contain thiomorpholino nucleotides, in a dose-dependent manner (FIG. 3). Lipofectin aids in cell uptake of the ODN and is not biologically active in the exon skipping analysis. ODN 1148 was the most active as can be readily seen at the lowest concentrations studied (5/10 nM). In contrast, the 2'-OMe PS control (the most active ODN studied prior to the inventors' results) is far less active in this assay. Moreover, the PMO oligonucleotide (conditionally approved by the FDA as a treatment for Duchenne Muscular Dystrophy) is inactive in this assay.

Figure 4:
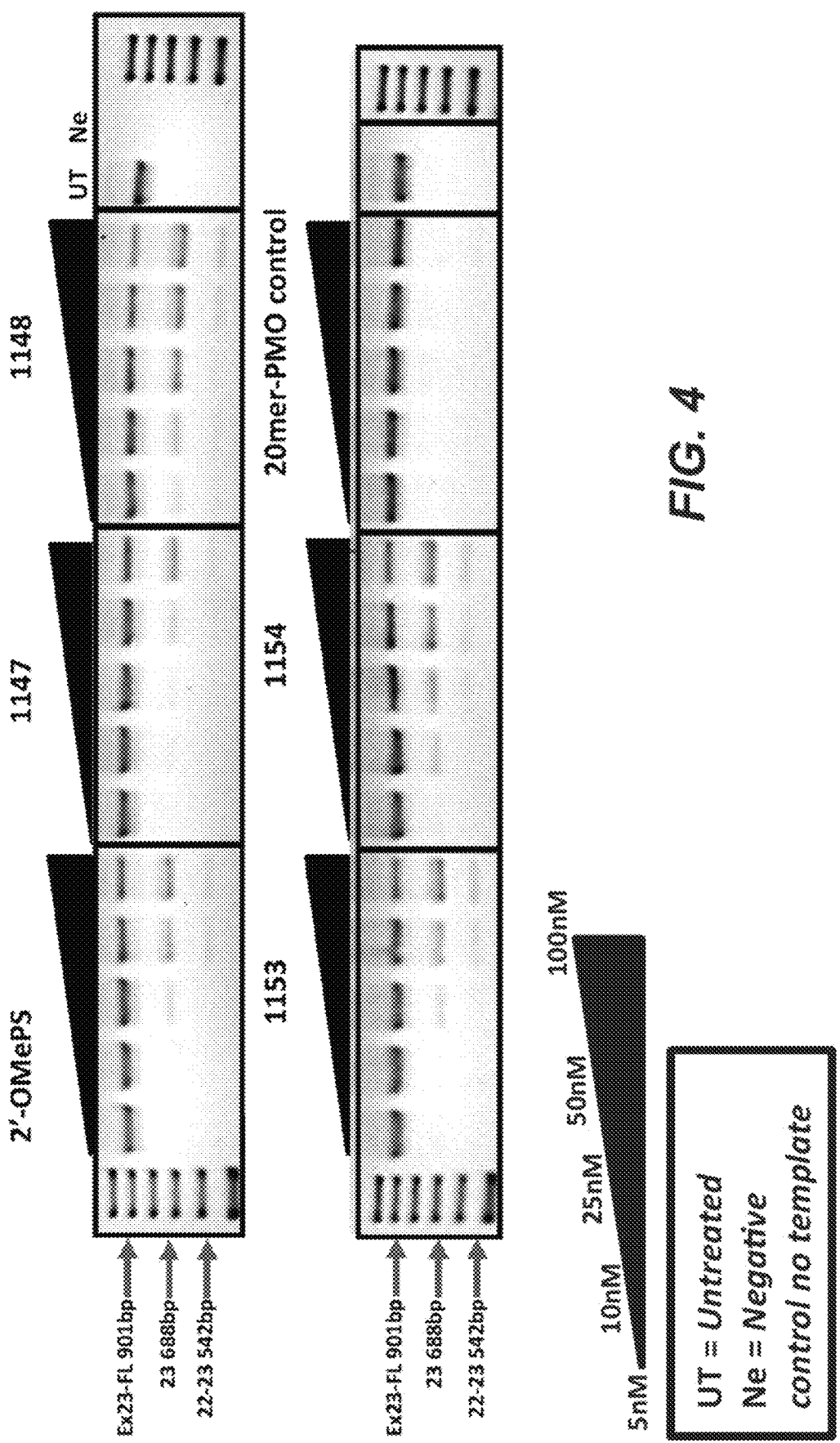
FIG. 4 shows a summary of the results from exon skipping of exon 23 when the transfection was conducted over one day with lipofectamine.
Figure 7:
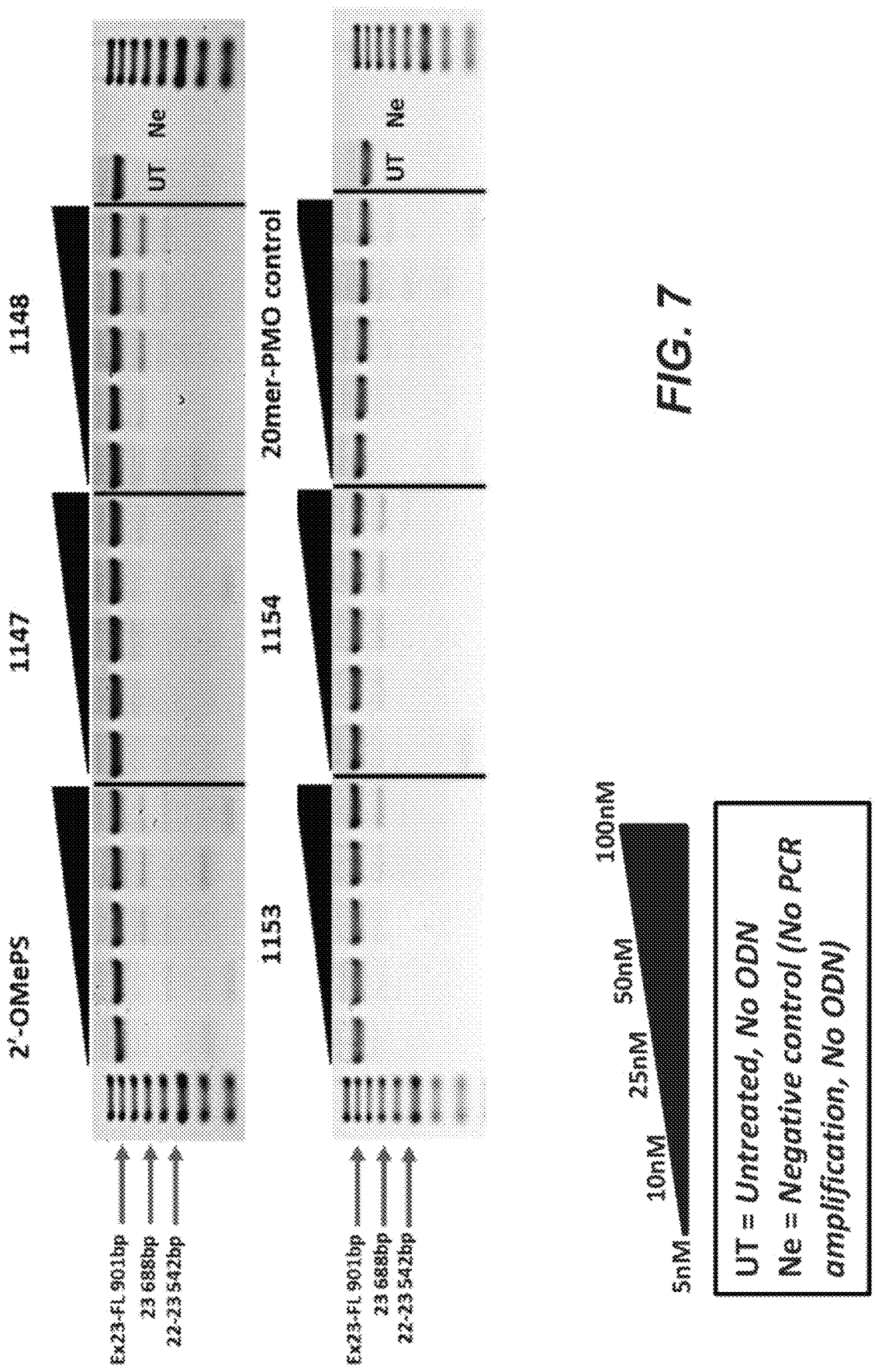
FIG. 7 shows a summary of the results from exon skipping of exon 23 when the transfection was conducted over 5 days in the absence of any lipid.

When ODNs were transfected into the mouse cell line with lipofectamine (24 hours), exon skipping was also observed with all four ODNs (ODNs 1147, 1148, 1153, and 1154) that contain thiomorpholino nucleotides (FIG. 4). ODN 1148 was again the most active as seen at the lowest concentrations studied (5/10 nM). In contrast, the 2'-OMe PS control (the most active ODN studied prior the inventors' results) is far less active in this assay. Moreover, the PMO oligonucleotide is also inactive in this assay. However, using lipofectamine to aid in transfection generates a less active profile for all ODNs tested. This is undoubtedly due to lipofectamine being unable to induce as much cell uptake of ODNs as lipofectin. This conclusion is supported by the results shown in FIG. 3 where cells were transfected in the absence of either lipofectin or lipofectamine (24 hours). Here no exon skipping was observed with any of the ODNs even at the highest concentration studied (100 nM). However, transfection with these same ODNs in the absence of lipid for five days generated exon skipping with ODN 1148 but none of the other ODNs (FIG. 7).

Figure 6:
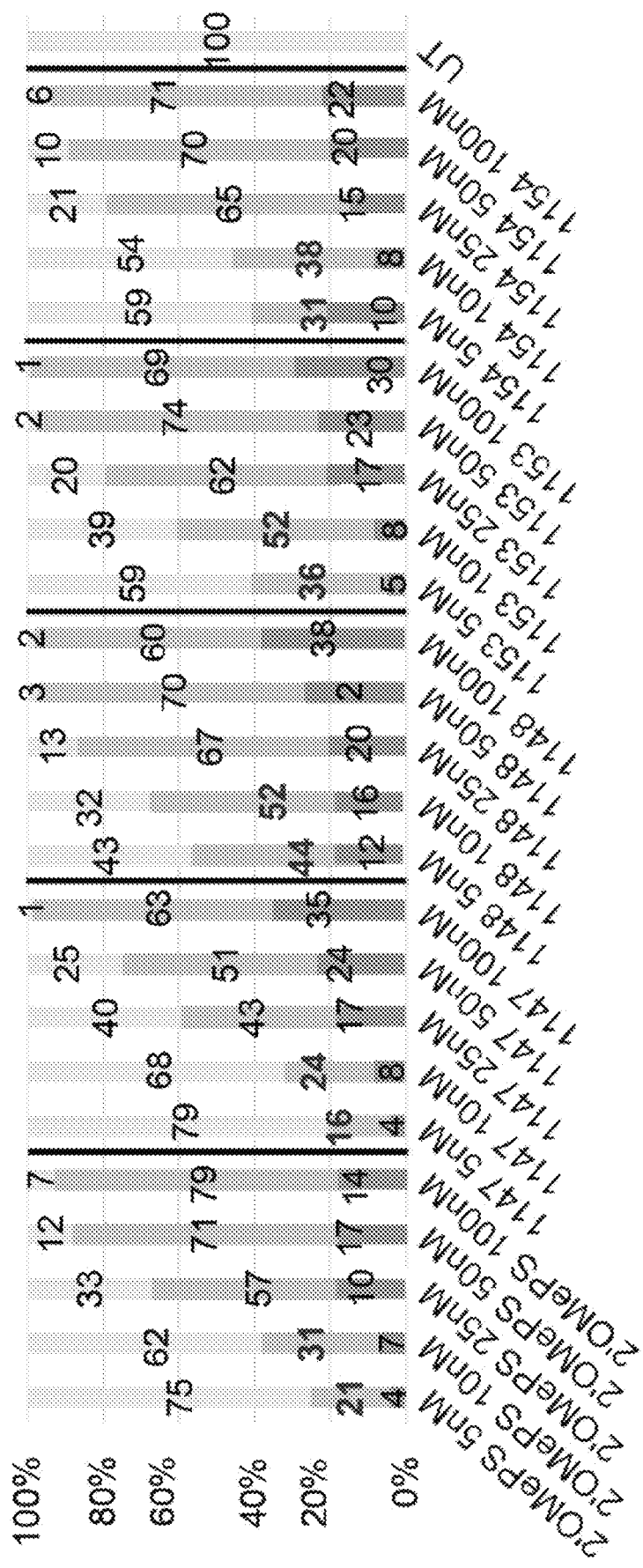
FIG. 6 shows a summary of the results shown in FIGS. 4 and 5 examined using densitometry analysis.
Figure 8:
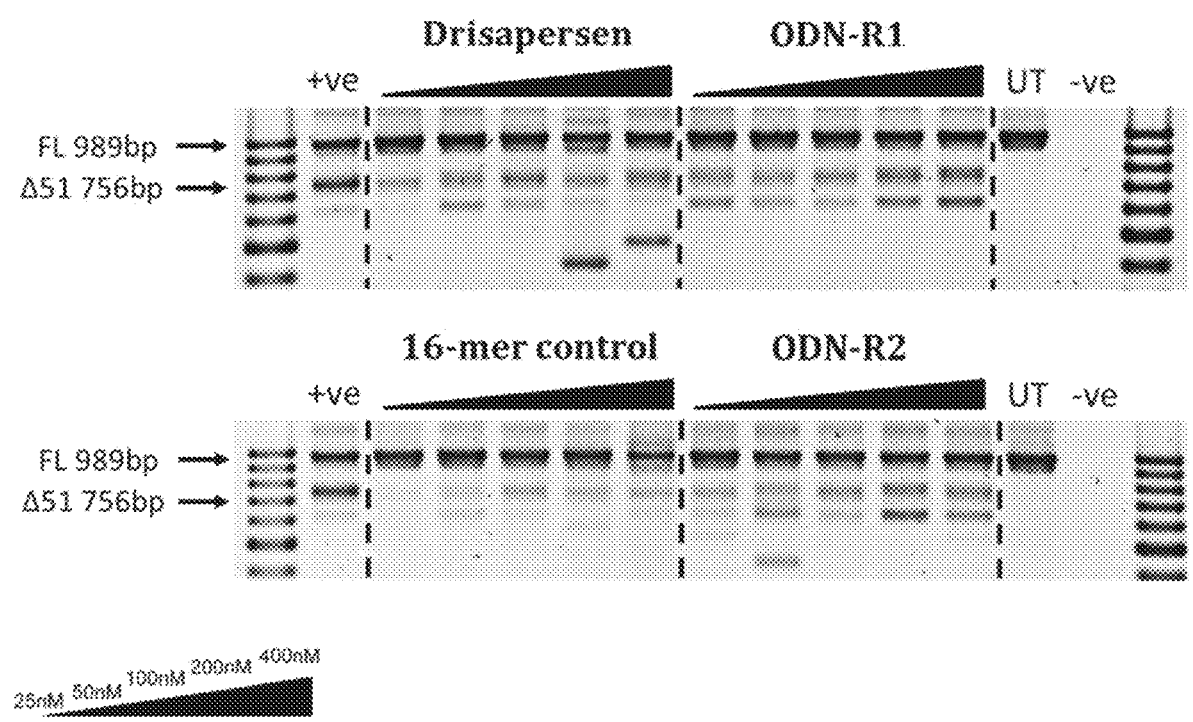
FIG. 8 shows a summary of the results from exon skipping of human exon 51 when transfection was conducted over one day with lipofectamine. The exon skipping efficiency of the ODN-R1 and R2 are more efficient than the 2'-OMePS control (Drisapersen and 16-mer, respectively)

When the results shown in FIG. 3, are submitted to densitometry analysis and the results plotted on a diagram shown in FIG. 6, it is clear that all four of the ODNs having thiomorpholino nucleotides outperformed the controls. This is especially obvious at the lowest concentrations studied (5 and 10 nM). As shown in the densitometry analysis, the thiomorpholino (1148) and thiomorpholino/DNA chimeras (1153 and 1154) induced efficient exon-23 skipping in a dose-dependent manner. Notably, 1148, 1153 and 1154 performed exceptionally well at lower concentrations (5 and 10 nM) which yielded 56 and 68%, 41 and 60%, 41 and 46% of exon-23 skipping products (23 and 22-23), respectively compared to control 2'OMePS ODN (25 and 38%). The PMO control did not induce any skipping. When thiomorpholino oligonucleotides are prepared that are complementary to the exon-intron junction of the human exon 51 Dystrophin gene and exon skipping measured (FIG. 8), exon skipping is also observed.

Example 4: Synthesis and Characterization of Thiomorpholino Oligonucleotides and Chimeras General Procedures for Chemical Synthesis: Commercially available DNA synthesis reagents were purchased from Glen Research (Sterling, Va.). Column chromatography purification of morpholino synthons was carried out using 60 Å standard grade silica gel from Sorbent Technologies (Norcross, Ga.). Thin-layer chromatography was performed on aluminum-backed silica 60 $F_{254}$ plates from Sigma Aldrich. $^1$H and $^{31}$P NMR spectra were recorded at 25° C. using a Bruker Avance-III 400 MHz NMR spectrometer. 5'-O-DMT-protected ribonucleosides of $N^6$-benzoyl adenosine, $N^4$-benzoyl cytidine, $N^2$-isobutyryl guanosine, and uridine were purchased from ChemGenes Corporation (Wilmington, Mass.). 5'-O-DMT-S-methyluridine was purchased from Carbosynth International (UK). All other chemical reagents and solvents were obtained from commercial suppliers and used without further purification.

HPLC Methods: Analytical HPLC injections were carried out using a Discovery® C18 HPLC column, 5 μm particle size, L×I.D. 15 cm×4.6 mm eluting at 1.5 mL/min with a gradient of acetonitrile/50 mM triethylammonium bicarbonate buffer, pH 8.5. Oligonucleotide Purification: Semi-preparative purification of crude DMT-ON oligonucleotides were carried out by ion-pair reverse-phase HPLC using an Agilent 1100 series HPLC instrument using the Agilent Zorbax SB-C18, 5 μm column 9.4 mm i.d.×250 mm on an Agilent 1100 HPLC. The eluent was monitored for absorption at 254 nm. Buffer A (50 mM TEAB in water) and buffer B (100% acetonitrile) were used to generate a gradient from 3% Buffer B to 100% buffer B over 40 minutes at a flow rate of 2 mL/min. The eluent fractions were collected using a Gilson FC204 fraction collector. Pooled fractions were evaporated to dryness in a vacuum evaporator (Thermo Savant) and analyzed by LCMS for purity. DMT-Off ODNs (that were generated by treatment of pure DMT-ON ODNs with 50% aqueous acetic acid for 5 minutes) were also purified using this procedure to obtain pure oligonucleotides for downstream experiments.

Solid-phase Synthesis: All standard phosphoramidites, 5'-fluorescein phosphoramidite, 5'-O-DMT-2'-deoxyribonucleotide-CPG, Universal support III and 5'-O-DMT-2'-OMe-RNA-CPG columns (1.0 μmol synthesis scale) were purchased from Glen Research (Sterling, Va.). All solid-phase syntheses were carried out using an Applied Biosystems Model 394 automated DNA synthesizer.

Chemical synthesis of appropriately protected 2'-deoxynucleoside morpholino phosphoroamidites (Compound 4a-d): Appropriately protected morpholino nucleosides (4a-d) were dried in vacuo overnight. To synthesize the diamidites, 1 equivalent morpholinonucleoside was dissolved in dichloromethane, followed by the addition of 1.2 equivalents of 2-cyanoethyl-N,N,N',N'-tetraisopropylphosphorodiamidite. After adding 0.5 equivalents of 5-Ethylthio-1H-Tetrazole (ETT), the reaction was allowed to stir for 30 minutes at 25° C. The reaction mixture was concentrated in vacuo and the residue was immediately purified by silica gel column chromatography, which was neutralized using a mixture of 1:1 Hexane-Ethylacetate containing anhydrous 3% triethylamine. An isocratic mixture of 1:1 Hexane-Ethylacetate was used to purify all phosphoroamidites.

Compound 4a: 5'-O-(4,4'-Dimethoxytrityl)-3'-O-cyanoethyl-2'-deoxyadenosine morpholino phosphorodiamidate. $^1$H NMR (400 MHz, Acetonitrile-$d_3$) δ 8.69 (s, 1H), 8.32 (dd, J=3.1, 1.3 Hz, 1H), 8.01 (d, J=7.6 Hz, 2H), 7.68-7.60 (m, 1H), 7.55 (dt, J=10.5, 5.3 Hz, 2H), 7.46 (dd, J=7.4, 1.9 Hz, 2H), 7.31 (dd, J=12.4, 8.3 Hz, 6H), 7.27-7.19 (m, 1H), 6.86 (d, J=8.4 Hz, 4H), 5.89 (ddd, J=34.6, 9.8, 2.6 Hz, 1H), 4.14-3.99 (m, 2H), 3.95-3.83 (m, 2H), 3.77 (d, J=1.3 Hz, 6H), 3.74-3.48 (m, 3H), 3.26-3.02 (m, 3H), 2.71-2.55 (m, 2H), 2.25-2.19 (m, 1H), 2.02-1.93 (m, 4H), 1.24-1.17 (m, 12H). $^{13}$C NMR (101 MHz, Acetonitrile-$d_3$) δ 158.68, 145.09, 145.07, 141.55, 135.89, 135.87, 135.84, 135.81, 132.57, 130.00, 129.98, 128.66, 128.15, 127.98, 127.96, 127.84, 126.86, 118.63, 117.35, 113.04, 85.95, 80.30, 80.24, 76.72, 76.56, 64.25, 64.16, 60.15, 60.11, 59.91, 59.88, 54.90, 43.69, 43.60, 43.57, 43.48, 23.90, 23.86, 23.84, 23.81, 23.78, 20.03, 19.95, 13.54. $^{31}$P NMR (162 MHz, Acetonitrile-$d_3$) δ 128.29, 126.47. ESI calcd. for $[C_{47}H_{53}N_8O_6P.Li]^+$ (M+Li)$^+$863.3980, found 863.4318. Yield 67%. (FIG. 9A-C).

Compound 4b: 5'-O-(4,4'-Dimethoxytrityl)-3'-O-cyanoethyl-2'-deoxyguanosine morpholino phosphorodiamidate. $^1$H NMR (400 MHz, Acetonitrile-$d_3$) δ 7.88 (d, J=6.6 Hz, 1H), 7.50-7.42 (m, 2H), 7.36-7.20 (m, 7H), 6.91-6.83 (m, 4H), 5.70-5.49 (m, 1H), 3.97 (dtd, J=10.2, 6.2, 5.7, 2.5 Hz, 1H), 3.90-3.81 (m, 2H), 3.78 (s, 6H), 3.75-3.68 (m, 1H), 3.53 (dt, J=10.1, 6.7 Hz, 2H), 3.25-3.15 (m, 3H), 3.11 (dd, J=9.7, 5.5 Hz, 1H), 2.96 (dd, J=11.9, 1.9 Hz, 1H), 2.77-2.66 (m, 3H), 2.62-2.52 (m, 1H), 2.00 (d, J=3.1 Hz, 1H), 1.28-1.13 (m, 19H). $^{13}$C NMR (101 MHz, Acetonitrile-$d_3$) δ 179.96, 179.93, 158.70, 155.38, 155.36, 148.21, 148.16, 148.14, 148.09, 145.07, 145.04, 136.87, 136.64, 135.88, 135.83, 135.80, 130.01, 129.98, 127.97, 127.95, 127.85, 126.88, 120.66, 120.56, 118.87, 118.70, 113.05, 85.96, 80.33, 80.28, 80.13, 80.03, 76.66, 76.58, 76.56, 64.25, 64.17, 60.04, 59.89, 59.80, 59.66, 57.14, 54.92, 49.52, 49.30, 47.90, 47.85, 47.00, 46.76, 46.00, 45.91, 43.64, 43.52, 43.41, 35.67, 23.96, 23.93, 23.89, 23.85, 23.81, 23.78, 23.70, 20.12, 20.04, 19.96, 18.23. $^{31}$P NMR (162 MHz, Acetonitrile-$d_3$) δ 129.40, 124.19. ESI calcd. for $[C_{44}H_{55}N_8O_7P.Li]^+$ (M+Li)$^+$845.4086, found 845.4440. Yield 59%. (FIG. 10A-C).

Compound 4c: 5'-O-(4,4'-Dimethoxytrityl)-3'-O-cyanoethyl-2'-deoxycytidine morpholino phosphorodiamidate. $^1$H NMR (400 MHz, Acetonitrile-d3) δ 7.98 (ddd, J=8.7, 5.9, 1.2 Hz, 3H), 7.69-7.59 (m, 1H), 7.58-7.43 (m, 5H), 7.39-7.21 (m, 7H), 6.93-6.85 (m, 4H), 5.69 (ddd, J=34.4, 9.4, 2.6 Hz, 1H), 3.98 (dddd, J=21.1, 10.4, 5.2, 2.4 Hz, 1H), 3.91-3.81 (m, 2H), 3.79 (d, J=0.8 Hz, 6H), 3.60 (dddd, J=16.7, 13.6, 10.0, 6.6 Hz, 2H), 3.49-3.40 (m, 1H), 3.29-3.21 (m, 1H), 3.18-3.08 (m, 1H), 2.76-2.67 (m, 2H), 2.59-2.37 (m, 2H), 2.00 (s, 1H), 1.23-1.15 (m, 12H). 13C NMR (101 MHz, Acetonitrile-$d_3$) δ 162.76, 158.70, 145.13, 145.10, 144.82, 135.93, 135.90, 135.87, 133.48, 132.89, 130.02, 130.00, 128.63, 128.13, 128.01, 127.99, 127.87, 126.88, 118.60, 117.36, 113.07, 85.93, 81.78, 81.68, 77.09, 77.04, 76.95, 64.32, 64.24, 60.13, 60.06, 59.99, 59.89, 59.84, 54.92, 49.45, 49.23, 48.15, 48.08, 46.76, 46.54, 45.60, 45.53, 43.64, 43.62, 43.52, 43.50, 23.89, 23.85, 23.83, 23.79, 23.77, 20.19, 20.01, 19.97, 19.93, 19.90. NMR (162 MHz, Acetonitrile-$d_3$) δ 127.38, 127.28. ESI calcd. for $[C_{46}H_{53}N_6O_7P.Li]^+$ $(M+Li)^+$839.3868, found 839.4269. Yield 66%. (FIG. 11A-C).

Compound 4d: 5'-O-(4,4'-Dimethoxytrityl)-3'-O-cyanoethyl-2% deoxythymidine morpholino phosphorodiamidate. $^1$H NMR (400 MHz, Acetonitrile-$d_3$) δ 7.46 (tdd, J=8.8, 2.8, 1.6 Hz, 3H), 7.38-7.35 (m, 1H), 7.33 (ddd, J=5.6, 2.9, 1.3 Hz, 5H), 7.30-7.21 (m, 2H), 6.88 (d, J=8.5 Hz, 4H), 5.62 (ddd, J=32.6, 9.9, 2.7 Hz, 1H), 4.01-3.80 (m, 3H), 3.78 (s, 6H), 3.60 (ddq, J=16.9, 13.8, 6.8 Hz, 2H), 3.48-3.37 (m, 1H), 3.22 (dq, J=9.9, 7.0, 5.0 Hz, 2H), 3.14-3.04 (m, 1H), 2.70 (td, J=6.6, 5.6 Hz, 2H), 2.59-2.44 (m, 2H), 2.03-1.93 (m, 1H), 1.85 (s, 3H), 1.23-1.15 (m, 12H). $^{13}$C NMR (101 MHz, Acetonitrile-$d_3$) δ 163.78, 158.69, 150.15, 150.11, 145.12, 145.10, 136.10, 136.00, 135.95, 135.91, 135.88, 135.85, 130.02, 129.99, 128.01, 127.99, 127.86, 126.88, 118.62, 118.59, 113.06, 110.01, 109.93, 85.92, 80.06, 80.02, 79.91, 76.92, 76.87, 76.83, 64.36, 64.28, 60.12, 60.05, 60.01, 59.88, 59.82, 54.93, 48.53, 48.31, 47.32, 47.24, 46.73, 46.53, 45.63, 45.54, 43.59, 43.48, 23.93, 23.89, 23.84, 23.81, 23.78, 20.21, 20.01, 19.93, 13.56, 11.63, 11.59. $^{31}$P NMR (162 MHz, Acetonitrile-$d_3$) δ 127.92, 127.73. ESI calcd. for $[C_{40}H_{50}N_5O_7P.Li]^+$ $(M+Li)^+$ 750.3602, found 750.3857. Yield 82%. (FIG. 12A-C).

Solid-Phase synthesis of TMO and TMO-chimeras: To synthesize TMO ODNs and its chimeras, the 5'-DMT group of the 2'-deoxyribonucleoside attached to the solid-support (CPG-500 support, Glen Research) was deprotected using deblock reagent (3% trichloroacetic acid in dichloromethane). The resulting 5'-hydroxyl-2'-deoxyribonucleoside was reacted with 6'-DMT-morpholinonucleoside phosphorodiamidate of mA$^{Bz}$, mG$^{iBu}$, mC$^{Bz}$, mT or commercial 2'-OMe phosphoramidites in presence of 0.12 M ETT in anhydrous acetonitrile with a 600 s condensation time. In the case of TMO-DNA pS chimera, a 30 second condensation time was used for coupling commercial 2'-deoxyribonucleotide phosphoramidites. In all cases, the nascent P(III) linkage was converted to thiophosphoramidate (TMO) or phosphorothioate (DNA pS, 2'-OMe pS) by sulfurization using 3-[(Dimethylaminomethylene)amino]-3H-1,2,4-dithiazole-5-thione (DDTT, 360 s). Following sulfurization, conventional capping reagents (Cap A: Tetrahydrofuran/Acetic Anhydride and Cap B: 16% 1-Methylimidazole in Tetrahydrofuran; Glen Research) were used to acetylate any unreacted hydroxyl groups, completing one synthesis cycle. Subsequent deprotection of the DMT protecting group using deblock resulted in dinucleotides that were ready for repetitive cycles to generate ODNs with exclusively TMO linkages or TMO-DNA pS/TMO-2'OMe pS chimeras. Multiple synthesis cycles were repeated until an ODN of desired length and sequence was generated. The 5'-DMT group on the ODN was not deprotected as a last step following solid-phase synthesis to enable DMT-On/Off purification. Upon completion of synthesis, cleavage and deprotection was carried out using 28% aqueous ammonia at 55° C. for 18 h. Following this, the ammonia solution was evaporated, and the residue dissolved in 3% aqueous methanol, filtered (0.2µ filter) to remove residue and analyzed by LCMS.

LCMS analysis of oligonucleotides (FIGS. 13-27): LCMS data was collected on an Agilent 6530 series Q-TOF LCMS spectrometer using Waters ACQUITY UPLC® BEH C18 (Waters Cat #186002352). Buffer A (aqueous phase) consisted of a combination of 2.5 mL triethylamine (TEA) and 26 mL hexafluoro-2-propanol (HFIP) in 97.5% water and 2.5% methanol. Organic mobile phase (buffer B) consisted of 2.5 mL TEA and 26 mL HFIP in 92% methanol and 5% water. The buffer gradient method during the runs used 0-100% of buffer B in 40 min followed by 100% B for 15 minutes at a flow rate of 0.2 mL/min at a set temperature of 25° C.

Nuclease susceptibility of TMO ODNs towards Snake Venom Phosphodiesterase I (FIGS. 28-43): Snake Venom Phosphodiesterase I (*Crotalus adamanteus*) was purchased from Sigma (St. Louis, Mo.). While performing enzymatic hydrolysis experiments, ODN 7, 8 or pSDNA ODN 12 (13.3 µM) was incubated at 37° C. in 200 µL of reaction mixture containing 100 mM Tris-HCl buffer (pH 8.5), 14 mM MgCl$_2$, 72 mM NaCl and Snake Venom phosphodiesterase I enzyme (0.1 or 0.2 U/mL). Aliquots were removed at various time points, heat inactivated and stored in dry ice until analyzed by analytical RP-HPLC.

Thermal Denaturation Studies (FIGS. 44A-F): UV thermal denaturation data were obtained on a Cary 100 Bio UV-VIS spectrophotometer equipped with a 6×6 thermostated multicell holder and Peltier temperature controller. Oligomers and complementary targets were mixed in equimolar ratios (1.0 µM in each strand) in 50 mM Tris-HCl, 50 mM KCl and 1 mM MgCl$_2$ pH 8.3. Samples were heated to 90° C. for 5 min, cooled slowly to 4° C. before Tm measurements. Thermal denaturation curves were acquired at 260 nm at a rate of heating of 0.5° C./min. The datasets were analyzed and processed with Cary WinUV software. Tm values were calculated as the maximum of first-derivative plots of absorbance versus temperature and have an uncertainty of ±1° C.

RNase H1 Experiments: The 5'-fluorescein labeled RNA (5'-F-RNA) was obtained commercially (IDT, Coralville, Iowa). To prepare TMO:RNA duplexes, the 5'-F-RNA ODN was mixed with either the exclusively TMO modified ODN 3, or the gapmer ODN 4 and the reaction mixture was heated to 90° C. and cooled to 4° C. over a period of 2 h. To assay for RNase H1 activity, 50 uL of 200 nM ODN: 5'-F-RNA duplex was added to a 70 uL reaction mixture containing 50 mM Tris-HCl, 75 mM KCl, 3 mM MgCl$_2$, 10 mM DTT and 100 U RNase H1 enzyme and incubated at 37° C. for 1 h. The reaction mixture was denatured by heat inactivation at 65° C. for 20 min and stored frozen at −20° C. until PAGE analysis was carried out. After adding DNA loading dye, samples were loaded on to 14 cm×16 cm×2 mm gels (15% gel, 8.0 M Urea) and PAGE was carried out using a running buffer which contained 89 mM Tris, 89 mM boric acid and 2 mM EDTA sodium buffered at pH ~9.0 (1×TBE). Following gel electrophoresis, the 5'-Fluorescein labeled RNA and its degraded fragments (those that still retained the fluorescein label) were visualized using a transilluminator.

CD Experiments: CD spectra were recorded on an Applied photophysics Chirascan™ Plus spectrometer at 25° C., in 200-350 nm wavelength range in a 0.5 mm pathlength cuvette. Oligonucleotide single strand concentrations were calculated based on the absorbance values measured at 25° C. The samples containing 10 μM/strand solution of each duplex were prepared in 10 mM Tris-HCl, 50 mM KCl, 1 mM $MgCl_2$, pH 8.3 (at 25° C.); denatured for two minutes at 90° C. and slowly cooled to 4° C. before the experiment. The buffer spectrum was subtracted from each duplex spectra prior to data analysis.

Dual-Luciferase Reporter Assays (FIG. 44): The HeLa-15b cell line was a kind gift from miRagen Inc., Boulder, Colo. Cells were cultured in Dulbecco's Modified Eagle's Medium (DMEM) supplemented with 10% fetal bovine serum (FBS) and penicillin-streptomycin (1%) at 37° C. and 5% $CO_2$. The cells were transfected in antibiotic-free, full-serum medium using the desired concentration of TMOs complexed with Oligofectamine™ transfection reagent. The cells were harvested at 48 h and 72 h time points and further analyzed using the Dual-Luciferase Reporter (DLR) Assay System (Promega). In the DLR Assay, the activities of firefly luciferase and Renilla luciferase are measured sequentially in each well. As a first step, the signal from the firefly luciferase reporter is measured by adding freshly prepared Luciferase Assay Reagent to generate a luminescent signal. After quantifying the firefly luminescence, this reaction is quenched and Renilla luciferase signal is generated simultaneously by adding Stop & Glo Reagent to the same sample. The resultant Renilla luciferase signal is quantified using a luminometer.

These results demonstrate that the thiomorpholino-containing oligonucleotides can be used to induce exon skipping in Dystrophin mRNA to generate functional Dystrophin protein and also to control microRNA biological activity.

Example 5: In Vitro Transfection of ODNs with Thiomorpholino ODNs into Human Cells Human Exon 51 DMD exon skipping was completed using normal human muscle myotubes. The experimental protocols were the same as those outlined in Example 3. And the results shown in FIG. 8. These results clearly show that the thiomorpholino oligonucleotides are more biologically active than the control 2'-Ome oligonucleotide (Drisapersen).

The various features and processes described above may be used independently of one another or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed is:

1. A method of treating muscular dystrophy in a human subject comprising administering a composition comprising an antisense oligonucleotide of 8 to 50 nucleotides in length, comprising at least 1 thiomorpholino nucleotide (TMO), which comprises a morpholino subunit, wherein the morpholino nitrogen of the morpholino subunit is linked by a thiophosphate-containing internucleotide linkage to a 5' exocyclic carbon of an adjacent nucleotide, or the 6'-exocyclic carbon of an adjacent morpholino subunit, or a TMO/DNA chimera, wherein and at least one nucleotide base comprises a base other than uracil, and wherein said TMO further includes at least 8 to 10 consecutive nucleotides complementary to a target region in an exon of the human dystrophin gene, wherein the antisense oligonucleotide specifically hybridizes to the target region inducing exon skipping, thereby treating muscular dystrophy in the subject.

2. The method of claim 1, wherein treatment increases the number of dystrophin-positive fibers to at least 20%, 30%, 40%, 50%, 60%, 70%, 80%, 90% or 95% of normal in the subject.

3. The method of claim 2, wherein the number of dystrophin-positive fibers is increased to between 20-60% of normal in the human subject.

4. The method of claim 1, wherein the muscular dystrophy is Duchenne muscular dystrophy, or Becker's muscular dystrophy.

5. The method of claim 1, wherein the antisense oligonucleotide comprises morpholino subunits linked by thiophosphate-containing internucleotide linkages joining a morpholino nitrogen of one residue to a 5' exocyclic carbon of an adjacent nucleotide or the 6'-exocyclic carbon of an adjacent morpholino nucleotide.

6. The method of claim 1, wherein the antisense oligonucleotide comprises at least 8 morpholino subunits linked by thiomorpholino-containing internucleotide linkages joining a morpholino nitrogen of one residue to the exocyclic carbon of an adjacent residue.

7. The method of claim 1, wherein the antisense oligonucleotide comprises thiomorpholino subunits and at least one of phosphorodiamidate and thiophosphate internucleotide linkages.

8. The method of claim 1, wherein the antisense oligonucleotide is chemically linked to one or more moieties or conjugates that enhance the activity, cellular distribution, or cellular uptake of the antisense oligonucleotide.

9. The method of claim 8, wherein the antisense oligonucleotide is conjugated to an arginine-rich peptide.

10. The method of claim 1, wherein the antisense oligonucleotide is 15 to 20 nucleotides in length.

11. The method of claim 1, wherein the antisense oligonucleotide is 20 to 30 nucleotides in length.

12. The method of claim 1, wherein the exon in the human dystrophin gene is selected from the group consisting of exon 23, exon 51, exon 50, exon 53, exon 45, exon 46, exon 44, exon 52, exon 55, and exon 8.

13. The method of claim 1, wherein the composition further comprises phosphate-buffered saline.

14. The method of claim 1, wherein the composition is administered by systemic administration.

15. The method of claim 1, wherein the composition is administered once weekly by infusion.

16. A method of treating a disease or disorder that is caused by the expression of truncated proteins that can be treated by exon skipping of a targeted exon during the splicing process in a human subject comprising administering a composition comprising an antisense oligonucleotide of 8 to 50 nucleotides in length, comprising at least 1 thiomorpholino nucleotide (TMO), which comprises a morpholino subunit, wherein the morpholino nitrogen of the morpholino subunit is linked by a thiophosphate-containing internucleotide linkage to the exocyclic carbon of an adjacent nucleotide, or a TMO/DNA chimera, wherein and at least one nucleotide base comprises a base other than uracil, and wherein said TMO further includes at least 8 to 10 consecutive nucleotides complementary to a target region in an exon of a target gene, wherein the antisense oligonucleotide specifically hybridizes to the target region inducing exon skipping.

* * * * *

SEQUENCE LISTING

```
<160> NUMBER OF SEQ ID NOS: 5

<210> SEQ ID NO 1
<211> LENGTH: 50
<212> TYPE: RNA
<213> ORGANISM: Homo sapiens

<400> SEQUENCE: 1
auaaacuucg aaaauuucag guaagccgag guuuggccuu uaaacuauau            50

<210> SEQ ID NO 2
<211> LENGTH: 20
<212> TYPE: DNA
<213> ORGANISM: Artificial Sequence
```

```
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: n is a, c, g, or t

<400> SEQUENCE: 2
ggccaaacct cggcttaccn                                               20

<210> SEQ ID NO 3
<211> LENGTH: 20
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: n is a, c, g, or u

<400> SEQUENCE: 3
ggccaaaccu cggcuuaccn                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
tcaaggaaga tggcatttct                                               20

<210> SEQ ID NO 5
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 5
aggaagatgg catttc                                                   16
```